(12) United States Patent
Zhang et al.

(10) Patent No.: US 10,934,311 B2
(45) Date of Patent: Mar. 2, 2021

(54) HETEROCYCLIC COMPOUND USED AS FGFR INHIBITOR

(71) Applicant: Hangzhou Innogate Pharma Co., Ltd., Zhejiang (CN)

(72) Inventors: Hancheng Zhang, Zhejiang (CN); Shifeng Liu, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 50 days.

(21) Appl. No.: 16/068,791

(22) PCT Filed: Jan. 9, 2017

(86) PCT No.: PCT/CN2017/070674
§ 371 (c)(1),
(2) Date: Dec. 14, 2018

(87) PCT Pub. No.: WO2017/118438
PCT Pub. Date: Jul. 13, 2017

(65) Prior Publication Data
US 2019/0100531 A1    Apr. 4, 2019

(30) Foreign Application Priority Data

Jan. 8, 2016 (CN) .......................... 201610015536.X

(51) Int. Cl.
*C07D 498/04* (2006.01)
*C07D 413/12* (2006.01)
*C07D 471/08* (2006.01)
*A61P 35/00* (2006.01)

(52) U.S. Cl.
CPC ......... *C07D 498/04* (2013.01); *C07D 413/12* (2013.01); *C07D 471/08* (2013.01); *A61P 35/00* (2018.01)

(58) Field of Classification Search
CPC ... C07D 498/04; C07D 413/12; C07D 471/08
See application file for complete search history.

(56) References Cited

U.S. PATENT DOCUMENTS 8,293,746 B2 * 10/2012 Bold .................... C07D 401/12
514/252.14

FOREIGN PATENT DOCUMENTS

CN     101336237 A    12/2008
WO     2015057938 A1   4/2015

OTHER PUBLICATIONS

Y. Teo et al., 79 British Journal of Pharmacology, 241-243 (2015) (Year: 2015).*
Zámečníkova 9 Expert Opinion on Drug Discovery, 77-92 (2014) (Year: 2014).*
M. Touat et al., 21 Clinical Cancer Research, 2684-2694 (2015) (Year: 2015).*
Hulikal, Deuterium Labeled Compounds in Drug Discovery Process, Abstract (2010).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Int'l Search Report dated Mar. 22, 2017 in Int'l Application No. PCT/CN2017/070674.

* cited by examiner

*Primary Examiner* — Deepak R Rao
(74) *Attorney, Agent, or Firm* — Ice Miller LLP

(57) ABSTRACT

A heterocyclic compound is described, which is an inhibitor of FGFR (fibroblast growth factor receptor). Specifically, it is a compound represented by the following formula (I), including an isomer (enantiomer or diastereomer) which may be present, or a pharmaceutically acceptable salt thereof, prodrugs, deuterated derivatives, hydrates, solvates. The definition of each group in the formula (I) is as described in the specification. The compound of the present invention has FGFR inhibitory activity and can be used for preventing or treating a disease associated with FGFR activity or expression.

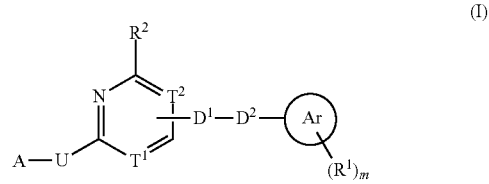

18 Claims, No Drawings

HETEROCYCLIC COMPOUND USED AS FGFR INHIBITOR

CROSS-REFERENCE TO RELATED APPLICATION

This application is a Section 371 of International Application No. PCT/CN2017/070674, filed Jan. 9, 2017, which was published in the Chinese language on Jul. 13, 2017, under International Publication No. WO 2017/118438 A1, which claims priority under 35 U.S.C. § 119(b) to Chinese Application No. 201610015536.X, filed Jan. 8, 2016, the disclosures of which are incorporated herein by reference in their entirety.

TECHNICAL FIELD

The present invention provides a series of novel heterocyclic compounds, their preparation method and their application as FGFR inhibitors in the treatment and prevention of various diseases.

BACKGROUND TECHNIQUE

Cancer, also known as malignant tumor, is one of the diseases with the highest incidence and highest mortality in the world. It is characterized by abnormal proliferation and metastasis of cells, and spreads and metastasizes within a short time or relatively short time after onset. Traditional treatment options include resection (if the ablation conditions are met), radiotherapy, and chemotherapy. The targeted therapy developed in recent years has the advantages of reducing toxicity, negative effects on patients, and improving survival rate. However, drug resistance occurs again within a certain period of time after the use of targeted drugs. The growth and spread of cancer cells will then be extremely rapid. Common cancers are: blood cancer, lung cancer, liver cancer, bladder cancer, rectal cancer, stomach cancer, and so on.

With the deepening of the research on molecular biology of cancer, people's understanding of the molecular mechanisms of tumorigenesis and development, as well as the understanding of different pathogenic targets, has been deepened. In many information transduction and pathways involved in the induction of cancer, protein kinases are a class of biologically active substances that catalyze the transfer of ATP's gamma phosphate group to the residues of many important proteins, phosphorylate them, transmit signals, and then participate in a series of cell activity, cell growth, differentiation, and proliferation. The development of selective protein kinase inhibitors to block or regulate diseases caused by abnormalities in these signaling pathways has been considered as an effective research strategy for the development of antitumor drugs. It has been validated in clinical trials and multiple protein inhibitors have been approved for marketing.

Studies have shown that protein tyrosine kinases (PTKs, tyrosine kinases) are the most common growth factor receptors and are closely related to the occurrence and development of tumors as the most important members involved in cell signaling. The activity of tyrosine kinase is too high, which leads to the activation of its downstream signaling pathways, which leads to cell transformation, proliferation, resistance to apoptosis, promotes cell survival, and ultimately leads to the formation of tumors. Therefore, in recent years, the trend of research and development of anti-cancer drugs has begun to shift from traditional cytotoxic drugs to drugs targeting abnormal signal transduction in cells, and related drugs have been applied to the clinic one after another. Compared with traditional cytotoxic anti-cancer drugs, these molecular-targeted drugs have strong curative effects and less toxicity, and have gradually become a hot spot for the antitumor drug discovery.

Among them, fibroblast growth factor receptors (FGFRs) are an important member of the receptor tyrosine kinase family and mainly include four subtypes of FGFR1, FGFR2, FGFR3, and FGFR4 (reference (1) Turner, N.; Grose, R. *Nature Reviews Cancer* 2010, 10, 116-129. (2) Dieci M. V.; Arnedos M.; Andre F.; Soria J. C. *Cancer Discovery* 2013, 3, 264-279). Due to gene amplification, mutation, fusion or ligand induction, FGFR members are continuously activated, induce tumor cell proliferation, invasion, migration, promote angiogenesis, and promote the development of tumors. FGFRs are highly expressed and abnormally activated in various tumors, such as non-small cell lung cancer, breast cancer, gastric cancer, bladder cancer, endometrial cancer, prostate cancer, cervical cancer, colon cancer, esophageal cancer, keratoblastoma, myeloma, Rhabdomyosarcoma and so on. Studies have shown that FGFR1 amplification accounts for 20% of squamous cell carcinoma of non-small cell lung cancer, and studies on in vitro proliferation, signaling pathways, etc. of FGFR1 amplified lung cancer cell lines show that FGFR selective inhibitors can effectively inhibit the activation of FGFR1 signaling pathway and proliferation (reference: (1) Weiss, J. et al *Sci. Transl. Med.* 2010, 2, 62ra93. (2) Dutt, A. et al *PLoS ONE* 2011, 6, e20351). In breast cancer, amplification of the chromosomal (8p11-12) region of FGFR1 accounts for approximately 10% of ER-positive patients and is associated with high expression of FGFR1 mRNA and poor patient prognosis. The aberrant activation of FGFR2 signaling pathway caused by FGFR2 gene amplification or mutation is mainly associated with gastric cancer, triple negative breast cancer, and endometrial cancer. FGFR2 amplification rate in gastric cancer tissues is 5%-10% (reference: Matsumoto, K. et al *Br. J. Cancer,* 2012, 106, 727-32). Analysis of 313 cases of gastric cancer revealed that FGFR2 amplification was significantly associated with tumor size, local infiltration, lymph node metastasis, and distant metastasis, and that FGFR2 amplification was generally a progressive tumor with poor prognosis. The overall survival rate of patients is relatively low (Jung, E.-J. et al *Hum Pathol.,* 2012, 43, 1559-66.). FGFR2 amplification accounts for 4% of refractory triple-negative breast cancers; endometrial cancer is a common gynecologic genital tumor, and FGFR2 mutations account for approximately 12% of endometrial cancers. In non-invasive bladder cancers, FGFR3 mutations account for 50%-60%, and invasive bladder cancers account for 10%-15% of FGFR3 mutations. The gene rearrangement at the FGFR3 t(4;14) position in multiple myeloma accounts for 15-20%. In addition, many subtypes of FGFR and its ligand FGFs have abnormal expression and activation in liver cancer, such as FGFR2, FGFR3, FGFR4, FGF19, FGF2, FGF5, FGF8, FGF9 and the like. Multiple preclinical and clinical studies have shown the importance of abnormal activation of FGF/FGFR axis in liver cancer (Cheng, A. L.: Shen, Y. C.; Zhu, A. X. *Oncology* 2011, 81, 372-80.). It should not be overlooked that abnormal activation of the FGF/FGFR axis is closely related to resistance to EGFR inhibitors, neovascularization inhibitors, and endocrine therapy. (Nicholas, T.; Richard, G. *Nature Reviews,* 2010, 10, 116-129).

In summary, the development of new FGFR inhibitors will be useful in the treatment of many types of tumors.

SUMMARY OF THE INVENTION

The purpose of the present invention is to provide a novel structure of FGFR inhibitors, as well as their preparation methods and applications.

In a first aspect, a compound of formula (I), including possible isomers (enantiomer or diastereomer), or a pharmaceutically acceptable salt, prodrug or deuterated derivative, hydrate, or solvate thereof is provided:

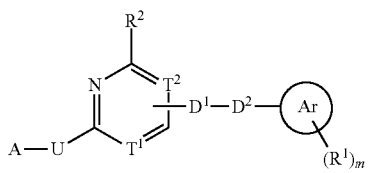

(I)

wherein:
$T^1$ is N or $CR^{13}$;
$T^2$ is N, $CR^{13}$, or C connected to $D^1$;
wherein each $R^{13}$ is independently selected from the group consisting of hydrogen, halogen, $C_{1-4}$ alkyl, CN, $OR^5$, or $NR^5R^6$;
$D^1$ is $NR^3$, O, S, $CHR^4$; wherein $R^3$ is hydrogen, $C_{1-4}$ alkyl, or $(CH_2)_p$—V—$(CH_2)_qN(R^6)C(O)R^5$; $R^4$ is hydrogen or $C_{1-4}$ alkyl;
$D^2$ is $C(O)NR^4$, C(O)O, $CHR^4$, $NR^4$, O, or S;
Ar is aryl or heteroaryl;
each $R^1$ is independently selected from the group consisting of hydrogen, halogen, $C_{1-4}$ alkyl, $C_{2-4}$ alkenyl, $C_{2-4}$ alkynyl, halogenated $C_{1-4}$ alkyl, CN, $OR^5$, $SR^5$, $NO_2$, $NR^5R^6$, $OCOR^5$, $C(O)R^5$, $C(O)OR^5$, $C(O)NR^5R^6$, $N(R^6)C(O)NR^5R^6$, $N(R^6)C(O)R^5$, $S(O)_2NHR^5$, $S(O)_2R^5$, or $NHS(O)_2R^5$;
m is 0, 1, 2, 3, 4 or 5;
$R^2$ is hydrogen, halogen, $C_{1-4}$ alkyl, CN, $OR^5$, or $NR^5R^6$;
U is $NR^7$ or O; wherein $R^7$ is hydrogen or $C_{1-4}$ alkyl;
each p and q is independently 0, 1, 2, 3, or 4;
V is a divalent group, when V is $CHR^5$, $C_{3-8}$ cycloalkyl, 3- to 8-membered heterocyclic, aryl, or heteroaryl, p is 0-4, q is 0-4; when V is CH=CH or C≡C, p is 1-4, q is 1-4; when V is O or $NR^{15}$, p is 2-4, q is 2-4; wherein $R^5$ is hydrogen, $C_{1-4}$ alkyl, $C(O)R^5$, or $S(O)_2R^5$;
each of $R^5$ and $R^6$ is independently hydrogen, $C_{1-8}$ alkyl, $C_{2-8}$ alkenyl, $C_{2-8}$ alkynyl, $C_{3-8}$ cycloalkyl, 3- to 8-membered heterocyclic, aryl, or heteroaryl;
or $R^5$ and $R^6$ together with the nitrogen atom they attached form a 3- to 8-membered cyclic structure (saturated or partially saturated) which optionally containing 0-2 additional heteroatoms selected from N, O or S;
A is formula (II):

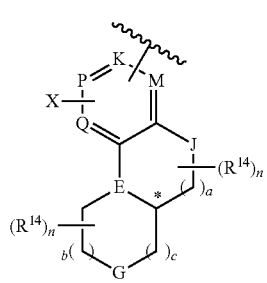

(II)

or A is a group selected from the group consisting of:

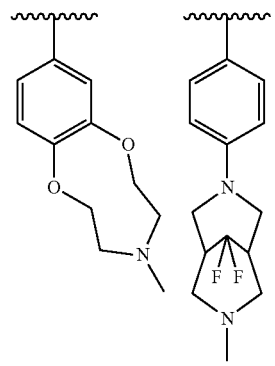

wherein:
"⌇⌇⌇" represents the attaching point of A to U in formula (I);
"*" indicates a chiral center;
each K, M, P and Q is independently N or $CR^8$;
X is hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;
each $R^{14}$ is independently hydrogen, halogen, $C_{1-4}$ alkyl, $C_{2-4}$ alkenyl, $C_{2-4}$ alkynyl, $C_{3-8}$ cycloalkyl, 3- to 8-membered heterocyclic, CN, $OR^5$, $SR^5$, $NR^5R^6$, $C(O)R^5$, $C(O)OR^5$, $C(O)NR^5R^6$, $OC(O)R^5$, $NR^6C(O)R^5$, $S(O)_2R^5$, =O, or =S;
n is 0, 1 or 2;
each a, b, and c is independently 0, 1, 2, or 3;
J is O, S, $CR^9R^{10}$, $NR^{12}$, or C(O);
E is N or $CR^{11}$;
G is $NR^{12}$, O, S, S(O). $S(O)_2$, or $CR^9R^{10}$;
wherein,
each $R^8$ is independently hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;
each $R^9$ or $R^{10}$ is independently hydrogen, halogen, or $C_{1-4}$ alkyl;
$R^{11}$ is hydrogen, $C_{1-4}$ alkyl, or $OR^5$;
$R^{11}$ is hydrogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;
wherein each of the above-mentioned alkyl, alkenyl, alkynyl, cycloalkyl, heterocyclic group, aryl, heteroaryl is optionally and each independently substituted with 1-3 substituents, and the substituents are each independently selected from halogen, $C_{1-4}$ alkyl, $C_{2-4}$ alkenyl, $C_{2-4}$ alkynyl, $C_{3-8}$ cycloalkyl, 3- to 8-membered heterocyclic group, aryl, heteroaryl, CN, $NO_2$, $OR^5$, $SR^5$, $NR^5R^6$, $C(O)R^5$. $C(O)OR^5$, $C(O)NR^5R^6$, $NC(O)NR^5R^6$, $N(R^6)C(O)R^5$, or $S(O)_2R^5$;
unless otherwise specified, the above aryl group is aryl group having 6 to 12 carbon atoms; and the heteroaryl group is 5- to 15-membered heteroaryl group.

In another preferred embodiment, in the compound of formula (I), U is $NR^7$; and/or
$D^1$ is $NR^3$; and/or
$D^2$ is $C(O)NR^4$; and/or
Ar is phenyl; and/or
$T^1$ is $CR^2$; and/or
$T^2$ is N,
wherein $R^2$, $R^3$, $R^4$ and $R^7$ are respectively as described above.

In another preferred embodiment, K, M, P and Q are each independently $CR^8$, wherein each $R^8$ is independently hydrogen, halogen, $C_{1-4}$ alkyl, or $OC_{1-4}$ alkyl.

In another preferred embodiment, J is O, NH, $NCH_3$, $CH_2$, $CF_2$, or C(O); E is N; G is $NR^{12}$, O, S, S(O), $S(O)_2$, or $CR^9R^{10}$, wherein $R^9$ and $R^{10}$ are each independently hydrogen or $C_{1-4}$ alkyl, and $R^{12}$ is hydrogen, $C_{1-4}$ alkyl, $C_{3-8}$ cycloalkyl, $C(O)C_{1-4}$ alkyl, or $S(O)_2C_{1-4}$ alkyl; each a, b and c are each independently 0, 1, or 2.

In another preferred embodiment, U is NH.

In another preferred embodiment, $D^1$ is $NCH_3$, $N(CH_2)_p$—V—$(CH_2)_qN(R^6)C(O)R^5$, or $N(CH_2)ArNHC(O)CH=CH_2$.

In another preferred embodiment, $D^2$ is C(O)NH.

In another preferred embodiment, $T^1$ is CH.

In another preferred embodiment, $R^1$ is each independently selected from the group consisting of hydrogen, halogen, $C_{1-4}$ alkyl, $C_{1-4}$ haloalkyl, CN, $OR^5$, and $C(O)R^5$; In another preferred embodiment, $R^1$ is each independently selected from the group consisting of halogen, and $OR^5$, while the $R^5$ is defined as above.

In another preferred embodiment, $R^2$ is hydrogen, halogen, $C_{1-4}$ alkyl, CN, $NR^5R^6$ or $OR^5$.

It should be understood by one skilled in the art that, when K, M, P and Q are each independently $CR^8$, then X is $R^5$.

It should be understood by one skilled in the art that, the selection of each of the above groups in the formula (II) should form a chemically stable tricyclic structure (e.g., an aryl-tricyclic structure).

It should be understood by those skilled in the art that, in the compounds of the general formula of the present invention, the selection of each group is based on the fact that each selected group combination can form a stable chemical structure, such as $D^1$ and $D^2$ selected in the formula (I). The combination can form a chemically stable functional group; the selected combination of V, p, and q can form a chemically stable functional group.

In another preferred embodiment, A is formula (II):

(II)

wherein:
each of K, M, P, and Q is independently N or $CR^8$; wherein, when any one of K, M, P, or Q is $CR^8$, the $R^8$ is X; and when any one of K, M, P, or Q is connected to U, it is C, i.e., $R^8$ does not exist;

X is hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;
while the remaining groups are defined as above.

In another preferred embodiment, P or K in formula (II) is C which is attached to U.

In another preferred embodiment, $R^{14}$ is $R^{17}$ or $R^{18}$, and formula (II) is:

wherein:
$R^{17}$ is hydrogen, halogen, $C_{1-4}$ alkyl, $C_{3-8}$ cycloalkyl, $OR^5$, $NR^5R^6$, $C(O)R^5$, $C(O)OR^5$, $C(O)NR^5R^6$, $OC(O)R^5$, $NR^6C(O)R^5$, $S(O)_2R^5$ or =O;

$R^{18}$ is hydrogen, halogen, $C_{1-4}$ alkyl, $OR^5$ or =O.

In another preferred embodiment, the compound (I) is of Formula (III):

(III)

while the groups are defined as above.

In another preferred embodiment, J is O, $CR^9R^{10}$, $NR^{12}$, or C(O);

E is N or $CR^{11}$;

G is $NR^{11}$ or O;

each $R^9$ or $R^{10}$ is independently hydrogen, halogen, or $C_{1-4}$ alkyl;

$R^{11}$ is hydrogen or $C_{1-4}$ alkyl;

$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^D$, $C(O)OR^5$, $C(O)NR^5R^6$, or $S(O)_2R^5$.

In another preferred embodiment, the compound (I) is of Formula (VI):

(VI)

A is a group selected from the group consisting of:

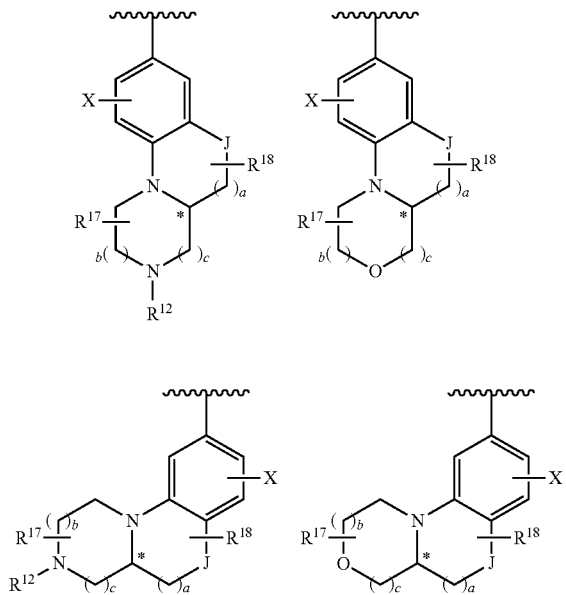

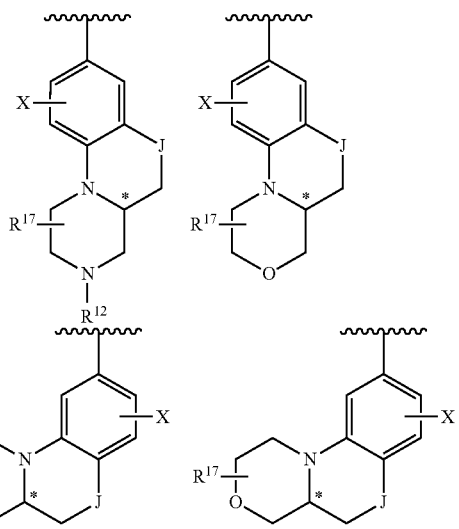

wherein:

"~~~" represents the attaching point of A to U in formula (I);

"*" indicates a chiral center;

X is hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;

each of a, b and c is independently 1 or 2;

J is O, $CR^9R^{10}$, $NR^{12}$, or C(O);

wherein, each $R^9$ or $R^{10}$ is independently hydrogen, halogen, or $C_{1-4}$ alkyl;

$R^{12}$ is hydrogen, $C_{1-4}$ alkyl. $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;

$R^5$ and $R^6$ are respectively defined as in claim 1;

$R^{17}$ is hydrogen, $C_{1-4}$ alkyl, or =O;

$R^{18}$ is hydrogen, $C_{1-4}$ alkyl, or =O;

$R^1$, m, $R^2$, $R^3$, and U are respectively defined as in claim 1.

In another preferred embodiment, a, b and c are each independently 1;

X is hydrogen, halogen, or $N(R^6)C(O)R$;

$R^{17}$ is hydrogen or =O;

$R^{18}$ is hydrogen;

J is O;

while the remaining groups are defined as above.

In another preferred embodiment, $R^1$, $R^2$, $T^1$, $T^2$, $D^1$, $D^2$, U, A, and Ar respectively corresponds to the respective compounds of the formula I prepared in the examples.

In another preferred embodiment, the A is selected from the group consisting of:

wherein:

"~~~" represents the attaching point of A to U in formula (II);

"*" indicates a chiral center;

X is hydrogen, halogen, $C_{1-4}$ alkyl, $NO_2$, $NR^5R^6$, or $N(R^6)C(O)R^5$;

J is O, $CR^9R^{10}$, $NR^{12}$, or C(O); wherein each $R^9$ or $R^{10}$ is independently hydrogen, fluoro, or $C_{1-4}$ alkyl;

$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;

$R^{17}$ is hydrogen, $C_{1-4}$ alkyl, or =O;

while the remaining groups are defined as above.

In another preferred embodiment, J is O;

In another preferred embodiment, J is $CR^9R^{10}$; wherein $R^9$ and $R^{10}$ are each independently hydrogen, fluoro, or $C_{1-4}$ alkyl;

In another preferred embodiment, J is C(O).

In another preferred embodiment, $R^{12}$ is $C_{1-4}$ alkyl, $C_{3-8}$ cycloalkyl, $C(O)R^5$, or $S(O)_2R^5$, preferably methyl.

In another preferred embodiment, m is 4, and the $R^1$ is substituted on ortho and meta.

In another preferred embodiment, each $R^1$ is independently halogen or methoxy.

In another preferred embodiment, the A is a group selected from the group consisting of:

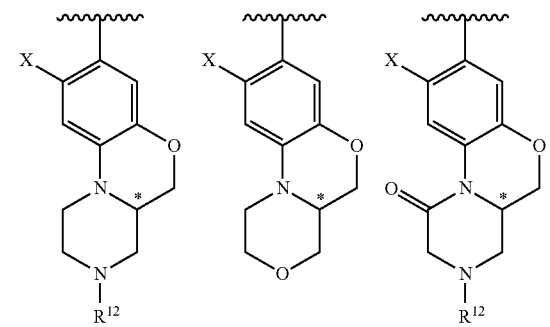

-continued

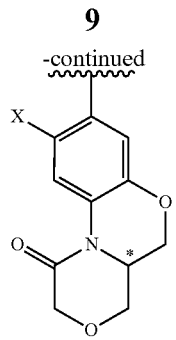

wherein:

" $\sim$ " represents the attaching point of A to U in formula (II);

"*" indicates a chiral center;

X is hydrogen, halogen, $C_{1-4}$ alkyl, $NO_2$, $NR^5R^6$, or $N(R^6)C(O)R^3$;

$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;

while the other groups are defined as in claim 1.

In another preferred embodiment, U is $NR^7$, wherein $R^7$ is hydrogen or $C_{1-4}$ alkyl; and/or $R^2$ is hydrogen or $C_{1-4}$ alkyl; and/or $R^3$ is hydrogen, $C_{1-4}$ alkyl, or $(CH_2)_p$—V—$(CH_2)_q N(R^6) C(O)R^5$; wherein V is $CHR^5$, $C_{3-8}$ cycloalkyl, 3- to 8-membered heterocyclic group, aryl, or heteroaryl; each p and q are each independently 0, 1, or 2; and/or each $R^1$ is each independently selected from the group consisting of hydrogen, halogen, $C_{1-4}$ alkyl, $C_{1-4}$ haloalkyl, CN, $OR^5$, $NR^5R^6$, or $N(R^6)C(O)R^5$;

m is 0, 1, 2, 3, 4 or 5;

while the remaining groups are defined as above.

In another preferred embodiment, U is NH; and/or $R^2$ is hydrogen; and/or $R^3$ is $C_{1-4}$ alkyl, or $(CH_2)_p$—V—$(CH_2)_q N(R^6) C(O)R^5$; wherein V is phenyl; p is 0, 1, 2 or 3; q is 0; and/or each $R^1$ is independently selected from the group consisting of hydrogen, halogen, $C_{1-4}$ alkyl, $C_{1-4}$ haloalkyl, CN, $C_{1-4}$ alkoxy;

m is 0, 1, 2, 3, or 4;

while the remaining groups are defined as above.

In another preferred embodiment, the compound (1) is of formula (V):

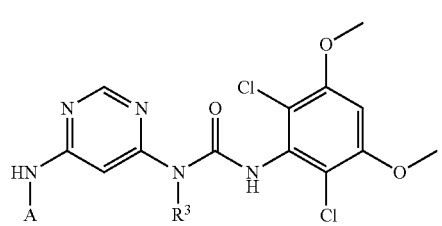

A is a group selected from the group consisting of:

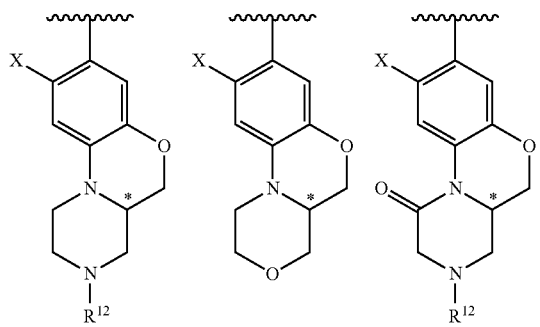

wherein,

" $\sim$ " represents the attach point of A to the rest of the molecule in formula (V);

X is hydrogen or $NHC(O)CH=CH_2$;

$R^{12}$ is hydrogen, $C_{1-4}$ alkyl, $C_{3-8}$ cycloalkyl, $C(O)C_{1-4}$ alkyl, or $S(O)_2C_{1-4}$ alkyl;

$R^3$ is methyl or formula (VI)

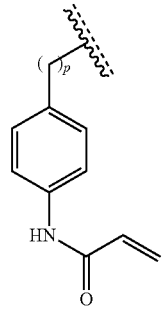

p = 0, 1, 2, 3 wherein " $\sim$ " represents the attaching point of $R^3$ to the nitrogen atom in formula (V);

with the proviso that when X is $NHC(O)CH=CH_2$, $R^3$ is not formula (VI); when $R^3$ is formula (VI), X is not $NHC(O)CH=CH_2$.

In another preferred embodiment, the compound (I) is of Formula (V):

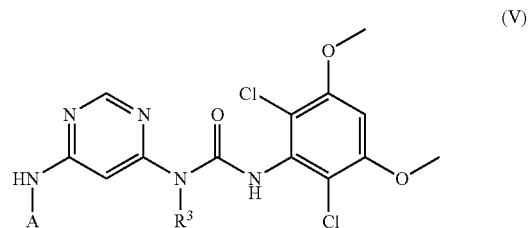

A is a group selected from the group consisting of:
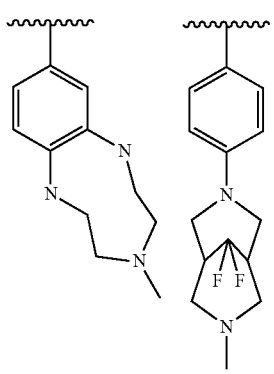
R³ is methyl or formula (VI)
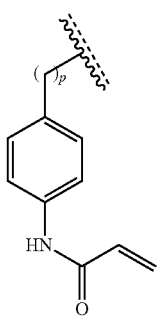
(VI)
p = 0, 1, 2, 3
wherein " " represents the attach point of R³ to the nitrogen atom in formula (V).
In another preferred embodiment, the compound is selected from the following group:
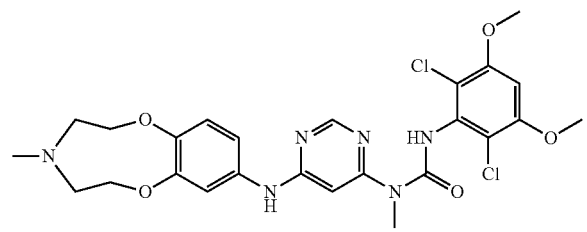
1
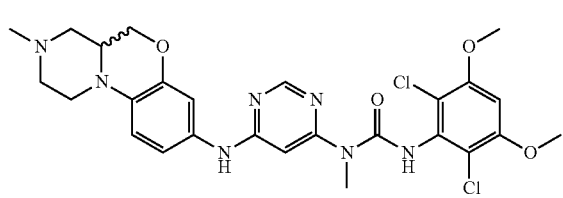
2
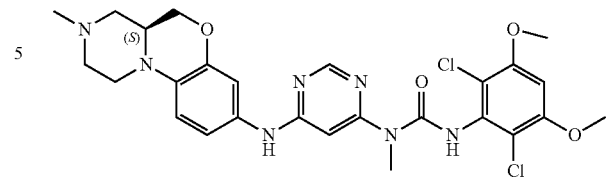
2S
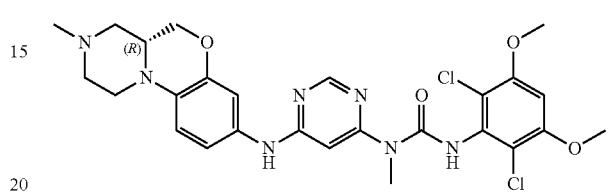
2R
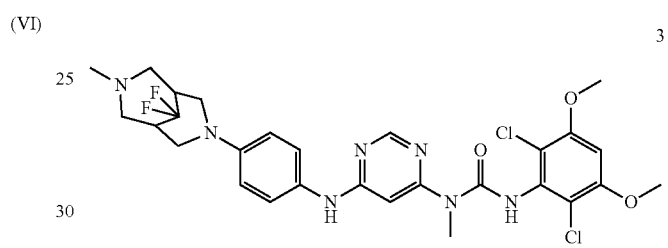
3
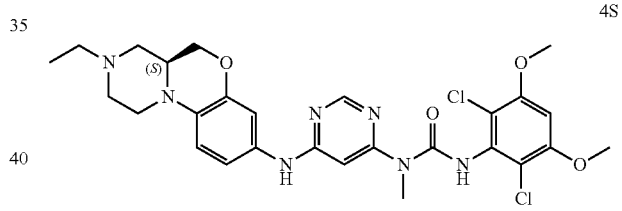
4S
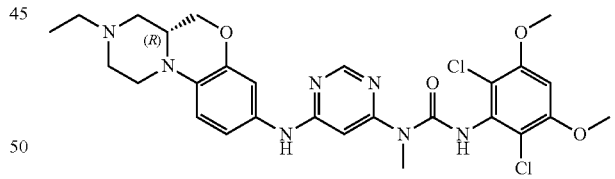
4R
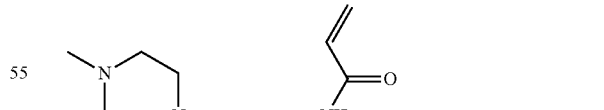
5S
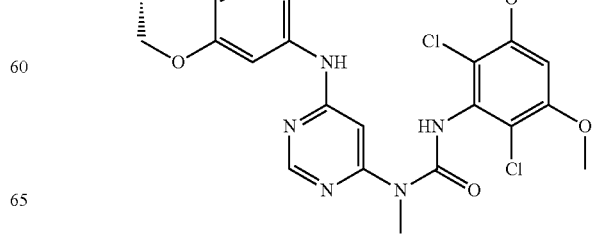

-continued
5R
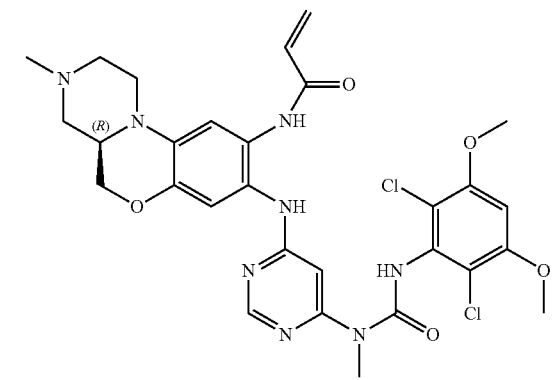
6S
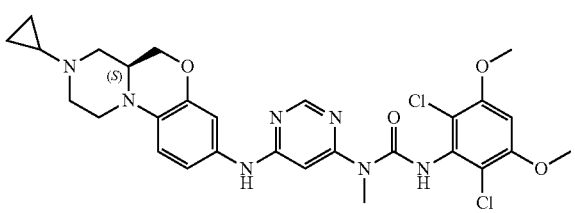
6R
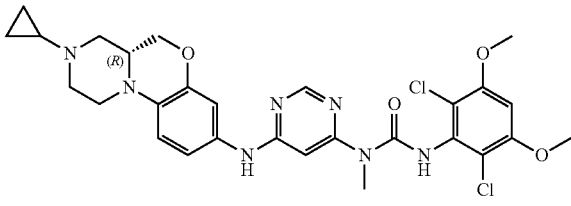
7S
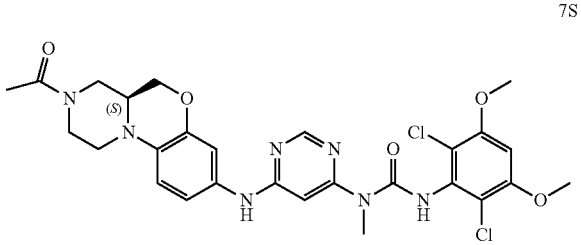
7R
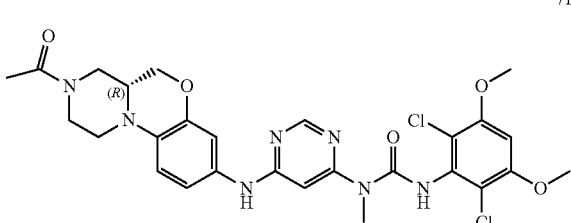
8S
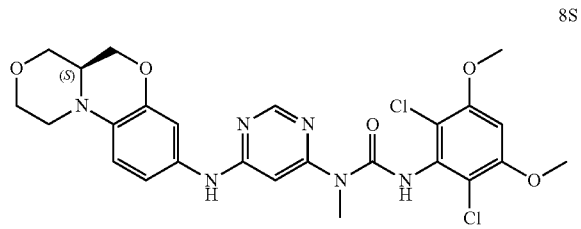
-continued
8R
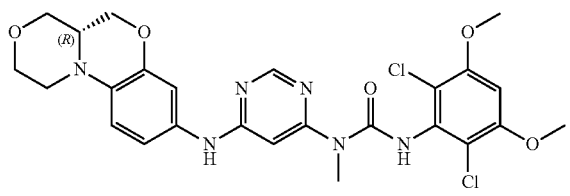
9S
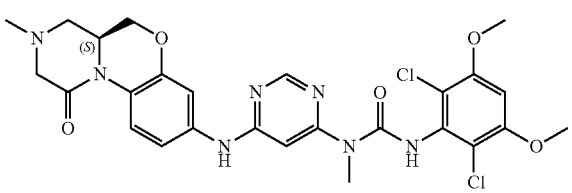
9R
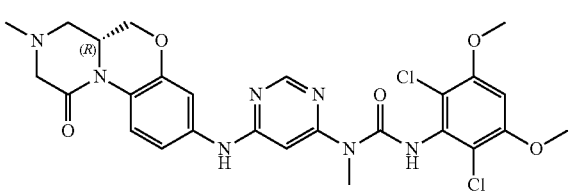
10S
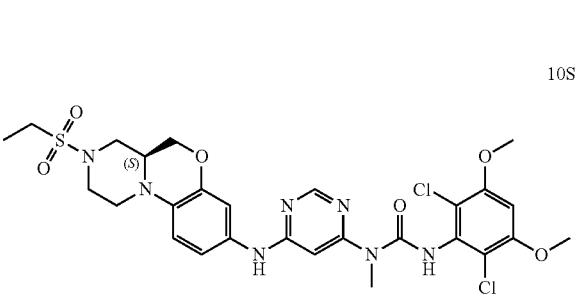
10R
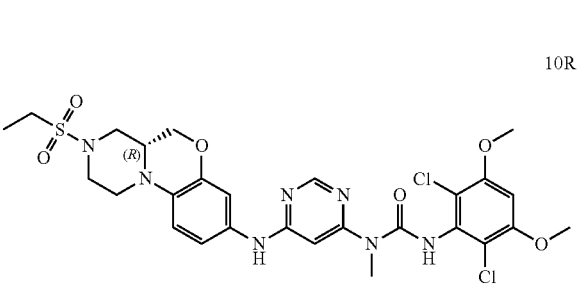
11S
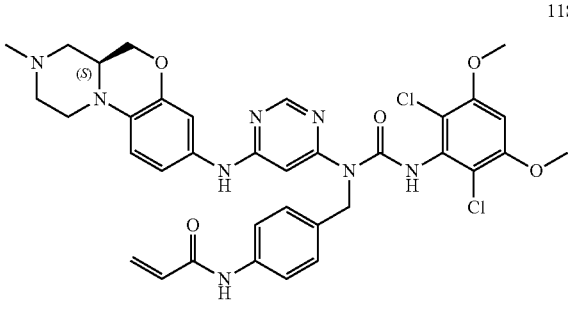

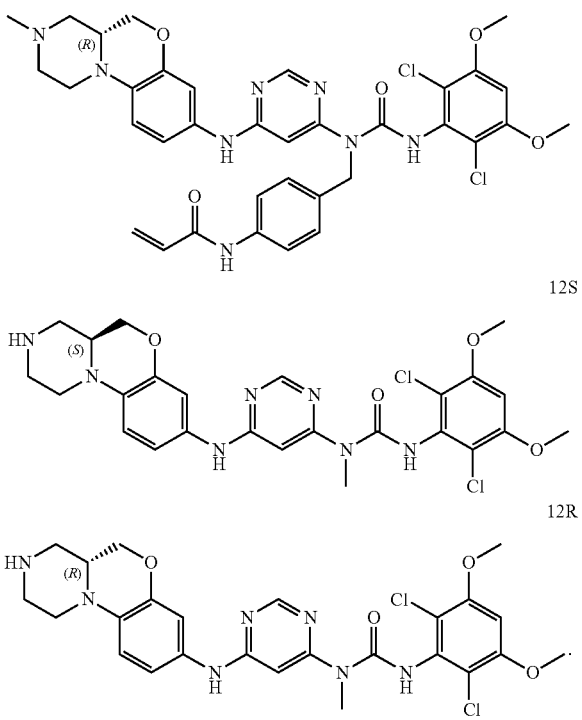

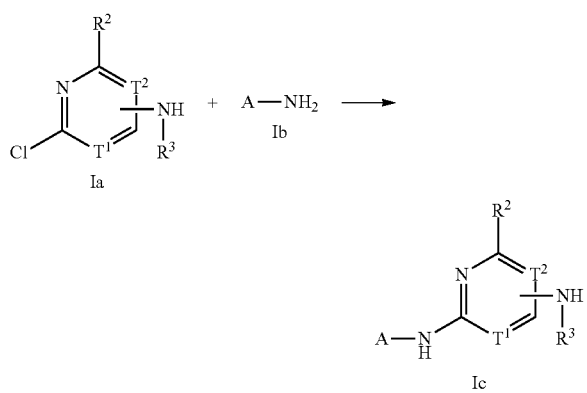

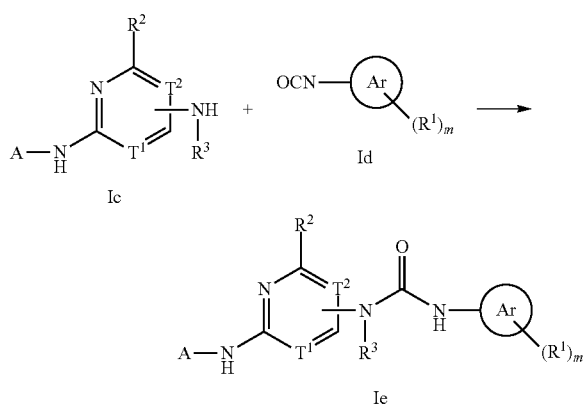

In the second aspect of the present invention, a use of the compound of the first aspect of the present invention is provided, wherein in:

(a) the preparation of medicine for treating diseases associated with FGFR activity or expression;
(b) the preparation of FGFR kinase targeting inhibitor; and/or
(c) in vitro non-therapeutic inhibition of FGFR activity.

In another preferred embodiment, the disease is selected from the group consisting of tumor, bone-related diseases, T cell-mediated inflammations, and autoimmune diseases.

In another preferred embodiment, the tumor is selected from the group consisting of lung cancer, bladder cancer, breast cancer, gastric cancer, liver cancer, salivary gland sarcoma, ovarian cancer, prostate cancer, cervical cancer, epithelial cell carcinoma, multiple myeloma, pancreatic cancer, Lymphoma, chronic myelogenous leukemia, lymphocytic leukemia, cutaneous T-cell lymphoma, etc.

In the third aspect of the present invention, a pharmaceutical composition is provided, wherein comprising: (i) therapeutically effective amount of formula (I) compound, or the pharmaceutically acceptable salt thereof, and (ii) pharmaceutically acceptable carrier.

At the same time, the compounds of formula (I) of the present invention may also be combined with other protein kinase inhibitor drugs, including those already marketed and drugs being tested in clinical trials, for the treatment of various cancers and tumors. The protein kinases mentioned herein include EGFR, FAK, SYK, FLT-3, Axl, CDK, JAK, etc., but are not limited to the above.

In the fourth aspect of the present invention, a method of inhibiting FGFR activity is provided, wherein comprising steps: administering an inhibitory effective amount of compound of any of the first aspect of the present invention or a pharmaceutically acceptable salt thereof to an inhibition subject, or administering an inhibitory effective amount of pharmaceutical composition of the third aspect of the present invention to an inhibition subject.

In another preferred embodiment, the inhibition is selective inhibition of FGFR.

In another preferred embodiment, the inhibition is FGFR inhibition.

In another preferred embodiment, the FGFR is selected from one or more of the group consisting of FGFR1, FGFR2, FGFR3, and FGFR4:

In another preferred embodiment, the inhibition of FGFR activity is in vitro non-therapeutic inhibition.

In the fifth aspect of the present invention, a method for the preparation of compound of the first aspect of the present invention is provided, wherein comprises the following steps:

(1) in an inert solvent, reacting compound 1a with compound 1b, so as to provide compound 1c;

(2) in an inert solvent, reacting compound 1c with compound 1d, so as to provide the target compound 1e; wherein the groups are defined as in the first aspect of the present invention.

It should be understood that in the present invention, the technical features specifically described above and below (such as the Examples) can be combined with each other, thereby constituting a new or preferred technical solution, which needs not be specified.

DETAILED DESCRIPTION

The inventors have long studied intensively and unexpectedly discovered a class of cyclic compounds having FGFR inhibitory activity and can therefore be used for the preparation of pharmaceutical compositions for the treatment of diseases associated with FGFR activity or expression levels. Based on the above findings, the inventors completed the present invention.

Definitions

Except where noted, "or" mentioned herein has the same meaning as "and/or" (meaning "or" and "and").

Except where noted, all chiral carbon atoms (chiral centers) of the compounds in the present invention may optionally be in the R configuration or the S configuration, or a mixture of the R configuration and the S configuration.

As used herein, the term "alkyl" when used alone or as part of another substituent refers to a straight (ie, unbranched) or branched saturated hydrocarbon group containing only carbon atoms, or a combination of straight and branched chains. When an alkyl group is preceded by a carbon-number modifier (eg, $C_{1-10}$), it means that the alkyl group contains 1 to 10 carbon atoms. For example, $C_{1-8}$ alkyl refers to an alkyl group containing 1-8 carbon atoms, including methyl, ethyl, propyl, isopropyl, butyl, isobutyl, sec-butyl, tert-butyl, or the similar groups.

As used herein, the term "alkenyl", alone or as part of another group, refers to a straight or branched chain, carbon chain group having at least one carbon-carbon double bond. Alkenyl groups may be substituted or unsubstituted. When an alkenyl group is preceded by a carbon-number modifier (such as $C_2$-8), it means that the alkenyl group contains 2-8 carbon atoms. For example, $C_{2-8}$ alkenyl refers to an alkenyl group containing 2 to 8 carbon atoms, including ethenyl, propenyl, 1,2-butenyl, 2,3-butenyl, butadienyl, or the similar groups.

As used herein, the term "alkynyl", by itself or as part of another substituent, refers to an aliphatic hydrocarbon group having at least one carbon-carbon triple bond. The said alkynyl group can be linear or branched, or a combination thereof. When an alkynyl group is preceded by a carbon-number modifier (such as $C_{2-8}$ alkynyl), it means that the alkynyl group contains 2-8 carbon atoms. For example, the term "$C_{2-8}$ alkynyl" refers to an alkenyl group containing 2 to 8 carbon atoms, including ethynyl, propynyl, isopropynyl, butynyl, isobutynyl, sec-butynyl, tert-butynyl, or similar groups.

As used herein, the term "cycloalkyl", when used alone or as part of another substituent refers to a saturated or partially saturated unit ring, bicyclic or polycyclic (fused, bridged, or spiro) ring system. When a cycloalkyl group is preceded by a carbon-number modifier (such as $C_{3-10}$), it means that the cycloalkyl group contains 3-10 carbon atoms. In some preferred embodiments, the term "$C_{3-8}$ cycloalkyl" refers to a saturated or partially saturated monocyclic or bicyclic alkyl group having 3 to 8 carbon atoms, including cyclopropyl, cyclobutyl, cyclopentyl, cycloheptyl, or similar groups. A "spiro cycloalkyl" refers to a bicyclic or polycyclic group sharing a single carbon atom (called a spiro atom) between single rings, which may contain one or more double bonds, but none of which has a completely conjugated n electron system. A "fused cycloalkyl" group refers to an all-carbon bicyclic or polycyclic group of a pair of carbon atoms adjacent to each other in the system that shares an adjacent pair of carbon atoms, wherein one or more rings may contain one or more double bonds. The key, but not a ring, has a completely conjugated π electron system. A "bridged cycloalkyl" refers to an all-carbon polycyclic group in which two rings share two carbon atoms that are not directly linked, and these may contain one or more double bonds, but none of the rings have a completely conjugated π electron The atoms contained in the cycloalkyl group are all carbon atoms. The following are some examples of cycloalkyl groups, and the present invention is not limited to the cycloalkyl groups described below.

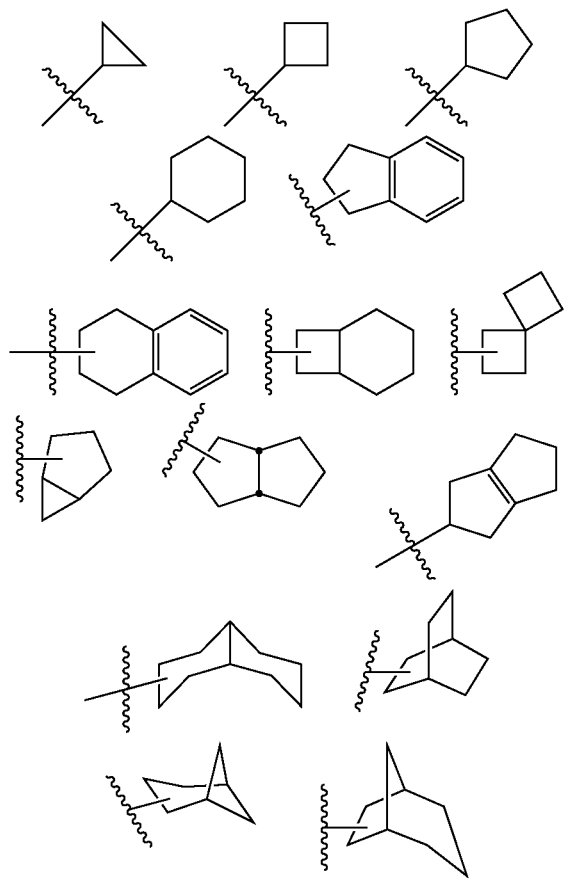

Unless stated to the contrary, the following terms used in the specification and claims have the following meanings. "Aryl" refers to an all-carbon monocyclic or fused polycyclic (i.e., rings that share adjacent pairs of carbon atoms) groups having a conjugated n electron, such as phenyl and naphthyl. The aryl ring may be fused to other cyclic groups (including saturated and unsaturated rings) but may not contain heteroatoms such as nitrogen, oxygen, or sulfur, and the point at which the precursors are attached must be on the carbon atom on the ring bearing the conjugated it-electron system. Aryl groups can be substituted or unsubstituted. The following are some examples of aryl groups, and the present invention is not limited to the aryl groups described below.

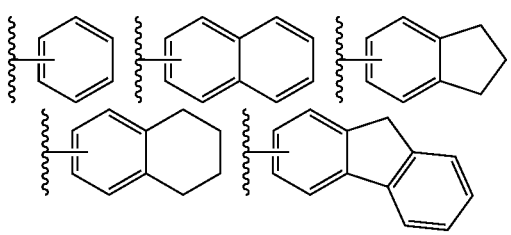

"Heteroaryl" refers to a heteroaromatic group containing one to more heteroatoms. The heteroatoms referred to here include oxygen, sulfur and nitrogen. For example, furyl, thienyl, pyridyl, pyrazolyl, pyrrolyl, N-alkylpyrrolyl, pyrimidinyl, pyrazinyl, imidazolyl, tetrazolyl, and the similar groups. The heteroaryl ring can be fused to an aryl, heterocyclyl, or cycloalkyl ring, wherein the ring attached to the parent structure is a heteroaryl ring. Heteroaryl groups can be optionally substituted or unsubstituted. The following are some examples of heteroaryl groups, and the present invention is not limited to the following heteroaryl groups. Among them, the last three heteroaryls are tricyclic heteroaryls, which are the focus of the present invention.

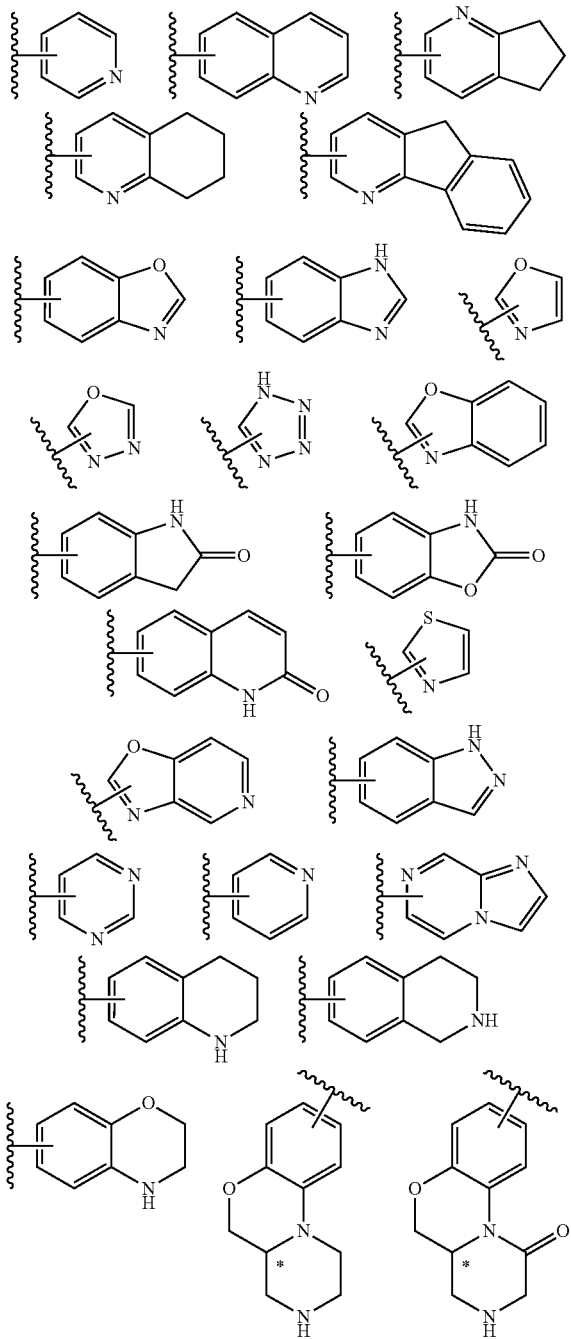

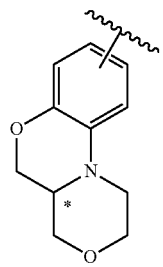

"Heterocyclyl" refers to a saturated or partially unsaturated monocyclic or polycyclic cyclic hydrocarbon substituent wherein one or more ring atoms are selected from nitrogen, oxygen, or sulfur and the remaining ring atoms are carbon. Non-limiting examples of monocyclic heterocyclyls include pyrrolidinyl, piperidinyl, piperazinyl, morpholinyl, thiomorpholinyl, homopiperazinyl. Polycyclic heterocyclyl refers to heterocyclic groups including spirocyclic, fused and bridged ring systems. "Spirocyclic heterocyclyl" refers to a polycyclic heterocyclic group sharing one atom (a spiro atom) between each ring in the system and the other rings in the system, wherein one or more ring atoms are selected from nitrogen, oxygen, or sulfur, and the remaining ring atoms are carbon. A "fused ring heterocyclyl" refers to a polycyclic heterocyclic group of a pair of atoms that is shared by each ring in the system with the other rings in the system, one or more rings may contain one or more double bonds, but no a single ring has a fully conjugated n electron system and one or more of the ring atoms is selected from nitrogen, oxygen, or sulfur, and the remaining ring atoms are carbon. A "bridged heterocyclyl" refers to a polycyclic heterocyclic group in which two rings share two atoms that are not directly linked, these may contain one or more double bonds, but none of the rings have a completely conjugated n electron system. And one or more of the ring atoms are selected from nitrogen, oxygen or sulfur, and the remaining ring atoms are carbon. If there are both saturated and aromatic rings in the heterocyclic group (for example, the saturated and aromatic rings are fused together), the point of attachment to the parent must be on the saturated ring. Note: When the point of attachment to the parent is on the aromatic ring, it is called a heteroaryl group and is not called a heterocyclic group. The following are some examples of heterocyclic groups, and the present invention is not limited to the following heterocyclic groups.

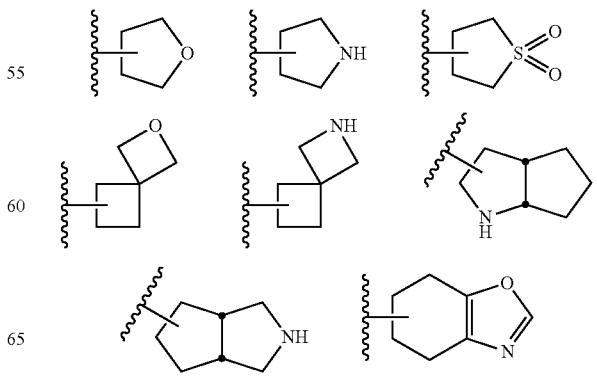

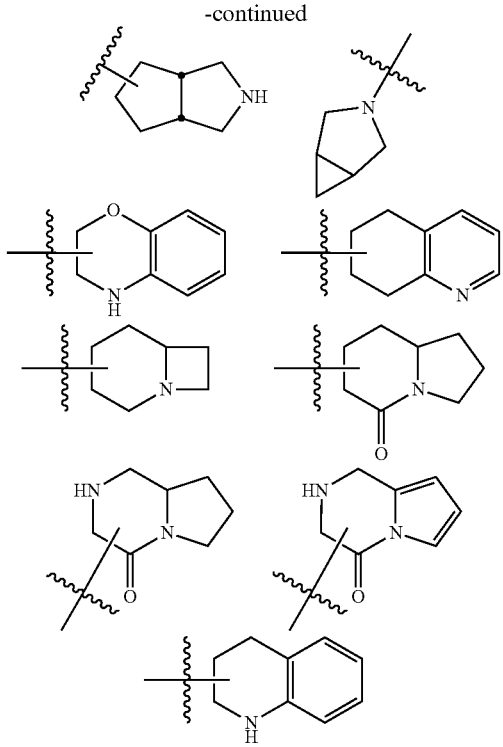

As used herein, the term "alkoxy" or "alkyloxy" refers to an alkyl group (eg, —O-alkyl) attached through an oxygen atom, wherein alkyl is as described above. Examples of specific alkoxy groups are, but not limited to, methoxy, ethoxy, propoxy, isopropoxy, butoxy, isobutoxy, sec-butoxy, tert-butoxy, or similar groups. Alkoxy groups may be substituted with one or more substituents such as halogen, amino, cyano, or hydroxy. Alkoxy groups can be straight or branched. When an alkoxy group is preceded by a carbon-number modifier (e.g., $C_{1-8}$), it means that the cycloalkyl group has 1-8 carbon atoms.

As used herein, the term "alkoxycarbonyl" refers to a straight-chain or branched alkyl-oxycarbonyl moiety (alkoxy-C=O). Alkoxy groups can have 1-8 carbon atoms. When an alkoxycarbonyl group is preceded by a carbon-number modifier (e.g., $C_{1-8}$), it means that the alkyl portion of the alkoxycarbonyl group contains 1-8 carbon atoms. For example, $C_{1-8}$ alkoxycarbonyl means a group having a $C_{1-8}$ alkoxy-C=O— structure, such as methoxycarbonyl, ethoxycarbonyl, tert-butoxycarbonyl, or the similar groups.

As used herein, the term "halogen" refers to F, Cl, Br, and I, either alone or as part of another substituent.

As used herein, the term "substituted" (with or without "arbitrary" modifications) means that one or more hydrogen atoms on a particular group are replaced with a particular substituent.

Specific substituents are the substituents correspondingly described in the foregoing, or the substituents appearing in the respective examples. Unless otherwise specified, an optionally substituted group may have one substituent selected from a particular group at any substitutable position of the group, which may be the same or different at each position. A cyclic substituent, such as a heterocyclic group, may be attached to another ring, such as a cycloalkyl group, to form a spirobicyclic ring system, ie, both rings have one common carbon atom. It will be understood by those skilled in the art that combinations of substituents contemplated by the present invention are those that are stable or chemically achievable.

Examples of such substituents include, but are not limited to, $C_{1-8}$ alkyl, $C_{2-8}$ alkenyl, $C_{2-8}$ alkynyl, $C_{3-8}$ cycloalkyl, 3- to 12-membered heterocyclic, aryl, heteroaryl, halogen, hydroxyl, carboxyl (—COOH), $C_{1-8}$ aldehyde, $C_{2-10}$ acyl, $C_{2-10}$ ester, amino.

For convenience and in line with conventional understanding, the term "arbitrary substitution" or "optional substitution" applies only to sites that can be substituted with substituents, and does not include those that are not chemically achievable. As used herein, unless otherwise indicated, the term "pharmaceutically acceptable salt" refers to a salt that is suitable for contact with the tissue of a subject (eg, a human) without producing untoward side effects. In some embodiments, pharmaceutically acceptable salts of a certain compound of the invention include salts (e.g., potassium, sodium, magnesium, calcium salts) of the compounds of the invention having acidic groups or have basic salts of the compounds of the invention of the group (e.g. sulfate, hydrochloride, phosphate, nitrate, carbonate)

General Synthesis of Compounds

The compound of the present invention represented by Formula I can be prepared by the following method, but the conditions of the method, such as reactants, solvents, bases, amount of the compound used, reaction temperature, time required for the reaction, and the like are not limited to the following. The compounds of the present invention can also be conveniently prepared by combining various synthesis methods described in this specification or known in the art, and such combinations can be easily performed by those skilled in the art to which the present invention pertains.

In the preparation method of the present invention, each reaction is usually carried out in an inert solvent at a reaction temperature of −78° C. to 150° C. (preferably 20 to 120° C.). The reaction time in each step is usually 0.5 to 48 h, preferably 2 to 12 h.

Scheme A describes the general synthesis of Compound A8:

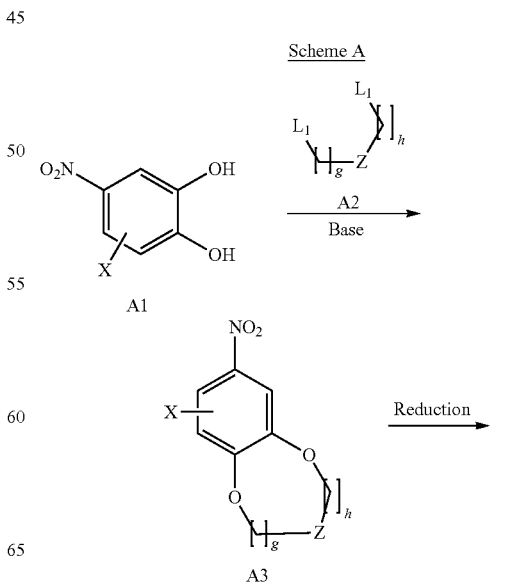

-continued
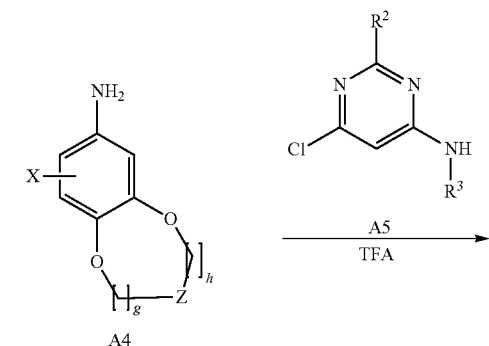
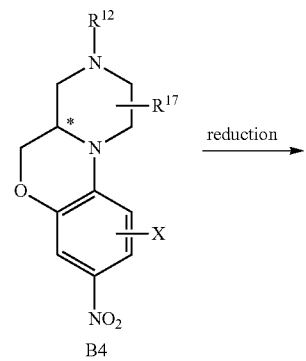
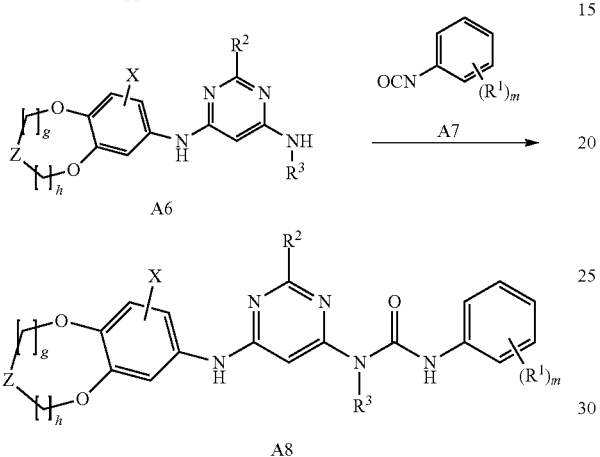
Z is O, N—R$^{12}$
L$^1$ is Leaving group
g is 2, 3, or 4
h is 2, 3, or 4
Scheme B describes the general synthesis of Compound B7:
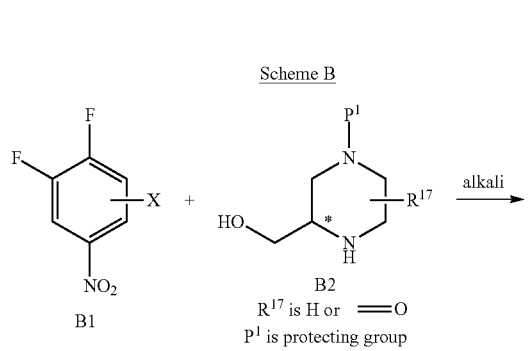
R$^{17}$ is H or =O
P$^1$ is protecting group
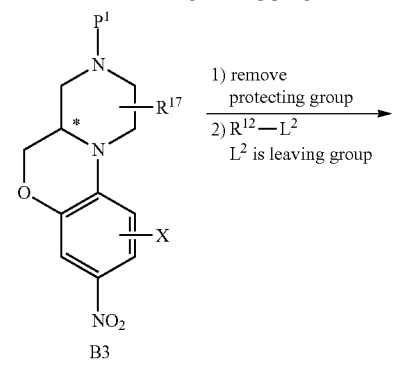
-continued
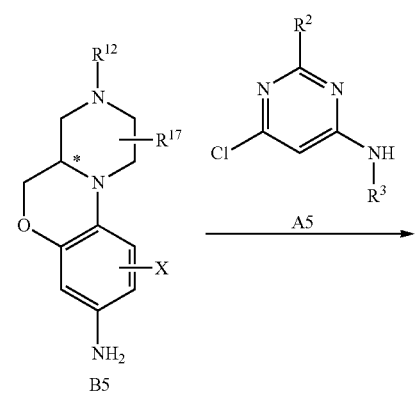
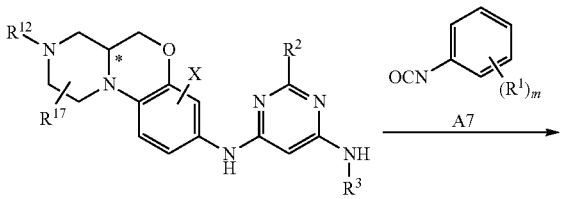
Scheme C describes the general synthesis of Compound C9:
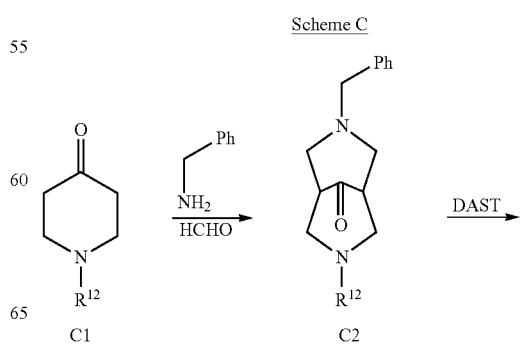

-continued
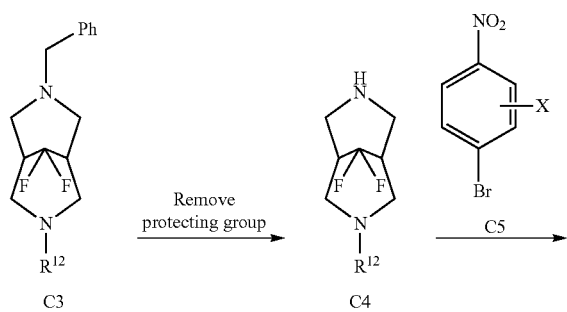
Scheme D describes the general synthesis of Compound D9:
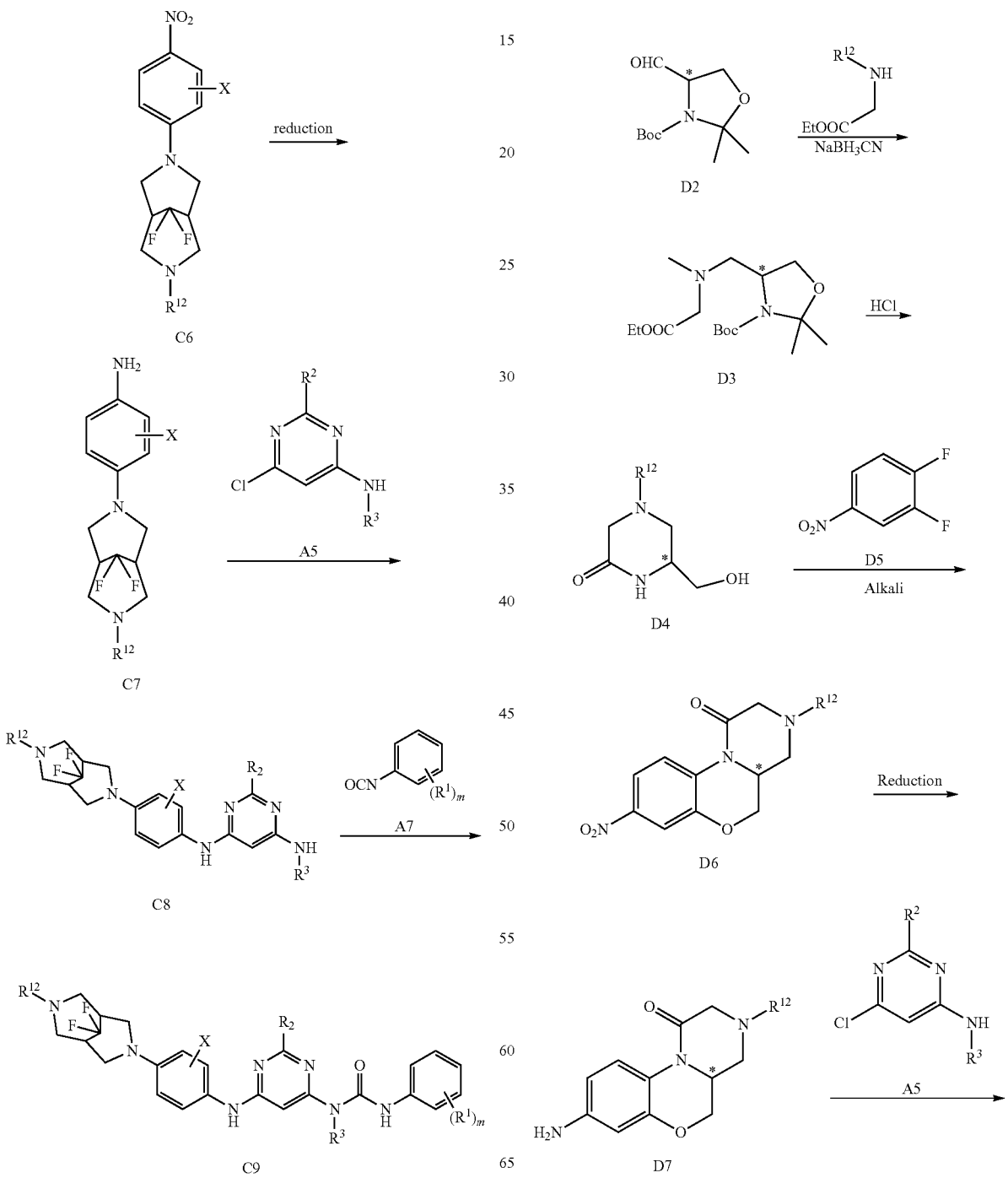

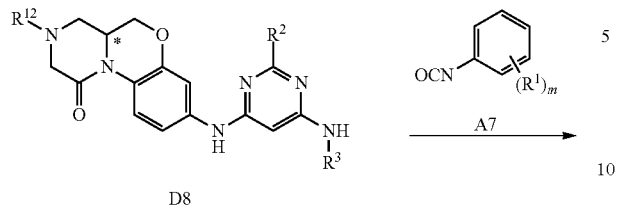
D8
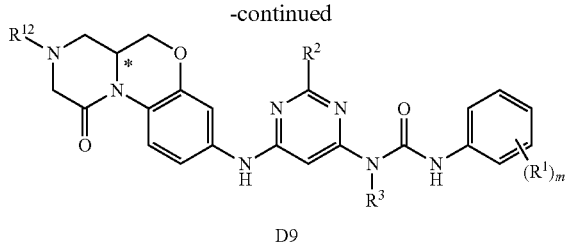
D9
Scheme F describes the general synthesis of Compound F8:
Scheme F
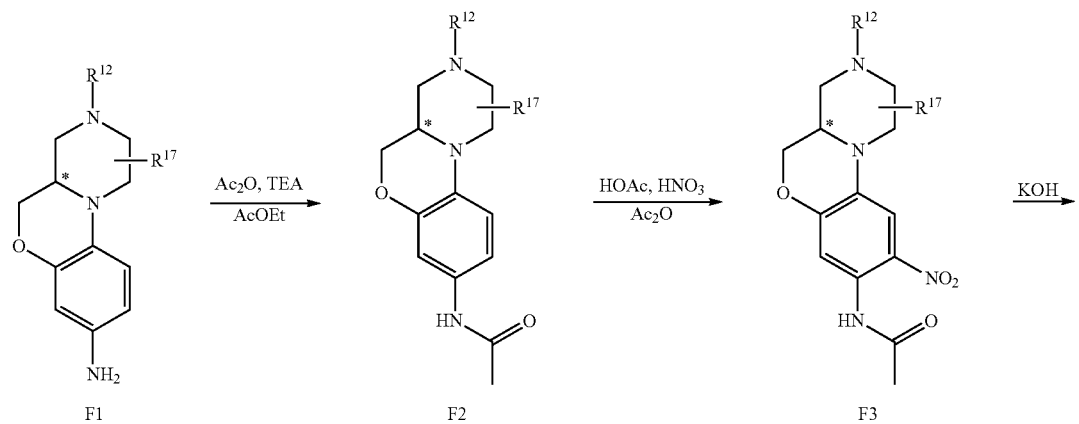
$R^{17}$ is H or =O
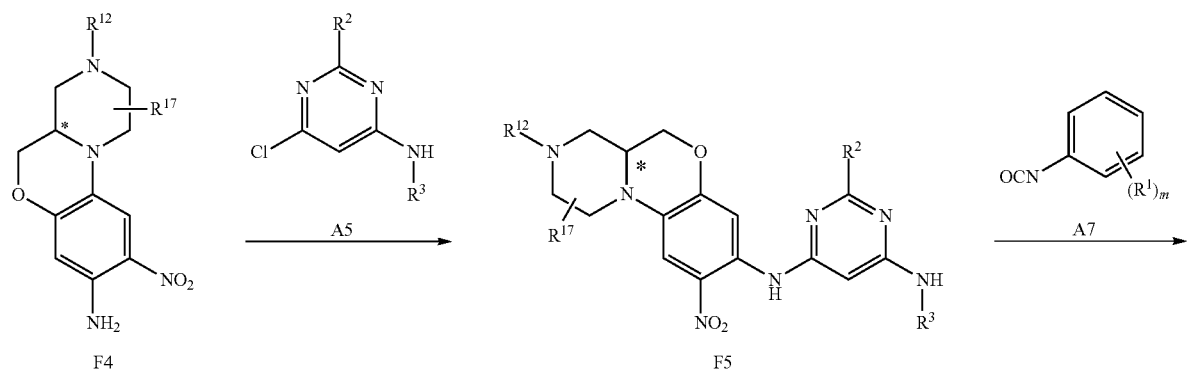
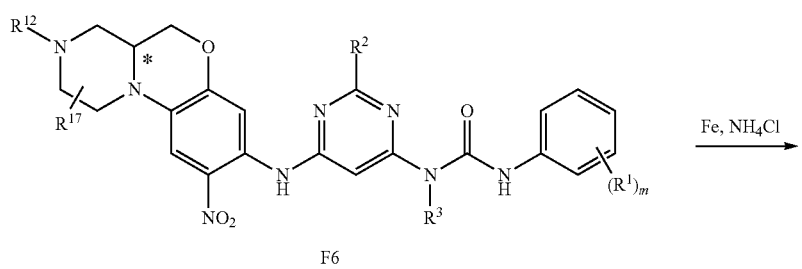

-continued
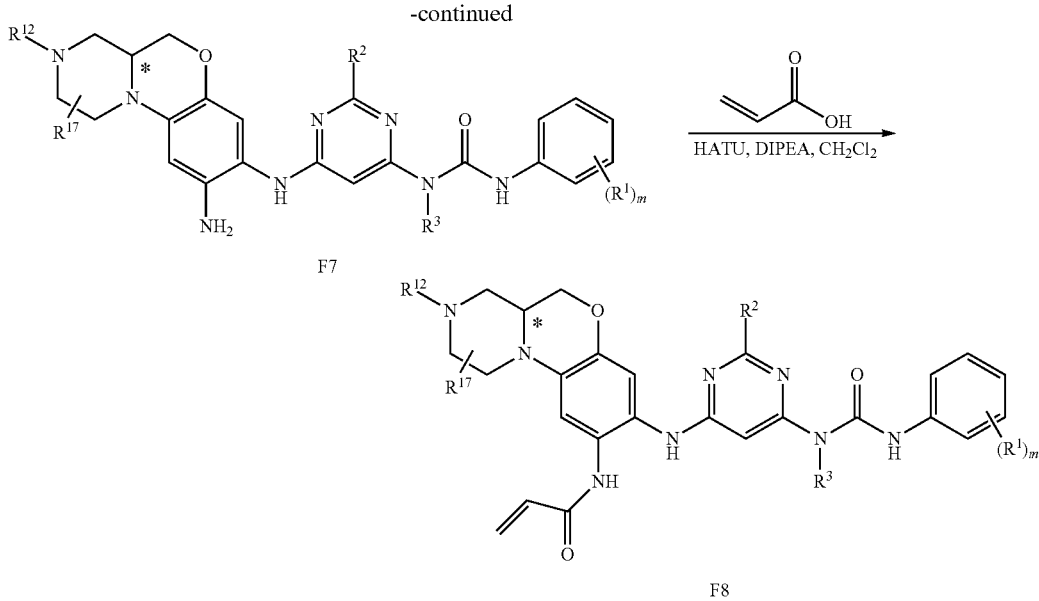
Scheme G describes the general synthesis of Compound G5:
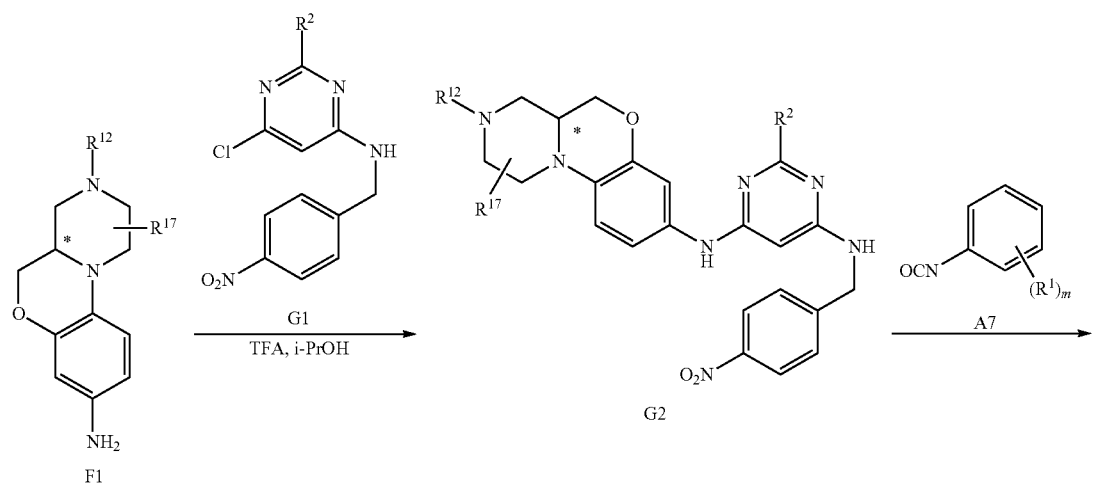
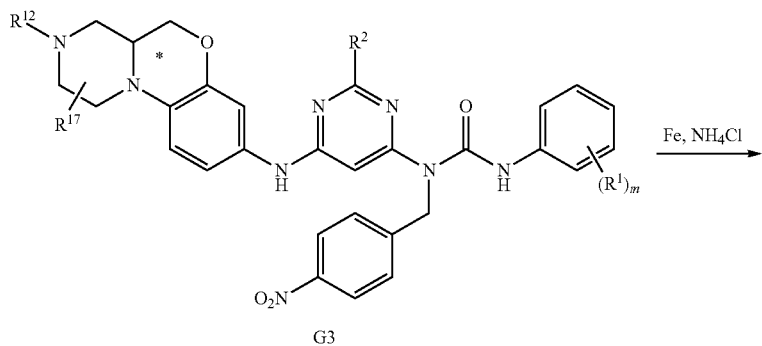

-continued

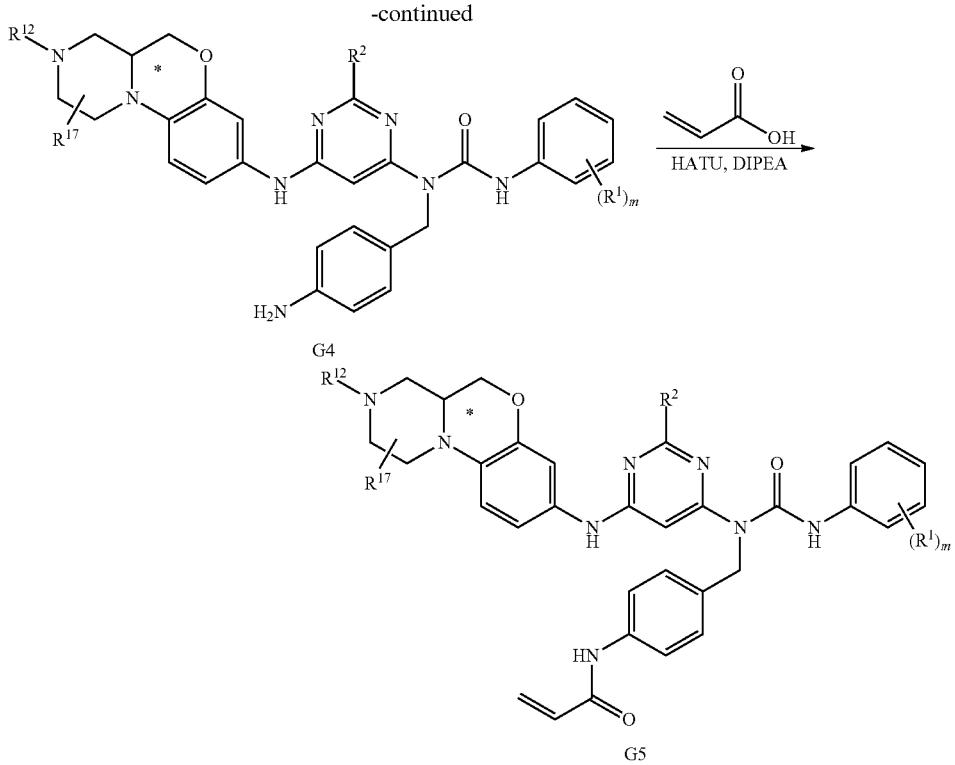

G4

G5

Pharmaceutically Acceptable Salts, Solvates, Stereoisomers, Tautomers

As used herein, the term "pharmaceutically acceptable salts" refers to salts of the compounds of the present invention with pharmaceutically acceptable inorganic and organic acids. Preferred inorganic acids include, but are not limited to, hydrochloric acid, hydrogen, and the like. Bromate, phosphoric acid, nitric acid, sulfuric acid; Preferred organic acids include, but are not limited to: formic acid, acetic acid, propionic acid, succinic acid, naphthalenedisulfonic acid (1,5), hypoaciatic acid, oxalic acid, tartaric acid, lactic acid, salicylic acid, benzoic acid, pentyl Acids, diethyl acetic acid, malonic acid, succinic acid, fumaric acid, pimelic acid, adipic acid, maleic acid, malic acid, sulfamic acid, phenylproprionic acid, gluconic acid, ascorbic acid, niacin, Isonicotinic acid, methanesulfonic acid, p-toluenesulfonic acid, citric acid, and amino acids.

As used herein, the term "pharmaceutically acceptable solvate" refers to a solvate of a compound of the present invention with a pharmaceutically acceptable solvent, wherein the pharmaceutically acceptable solvent includes (but is not limited to): water, ethanol, methanol, isopropyl alcohol, tetrahydrofuran, dichloromethane.

As used herein, the term "pharmaceutically acceptable stereoisomer" means that the chiral carbon atoms involved in the compounds of the present invention may be of the R configuration, the S configuration, or a combination thereof.

Pharmaceutical Composition and Application Method

Since the compound of the present invention has an excellent FGFR inhibitory activity, the compound of the present invention and its various crystal forms, pharmaceutically acceptable inorganic or organic salts, hydrates or solvates, and the compound containing the present invention are the main active ingredients. The pharmaceutical composition can be used to treat, prevent, and alleviate diseases associated with FGFR activity or expression levels. According to the prior art, the compounds of the present invention can be used to treat (but not limited to) the following diseases: various cancers, such as lung cancer, bladder cancer, breast cancer, stomach cancer, liver cancer, salivary gland sarcoma, ovarian cancer, prostate cancer, cervical cancer, Epithelial cell carcinoma, multiple myeloma, pancreatic cancer, lymphoma, chronic myeloid leukemia, lymphocytic leukemia, cutaneous T-cell lymphoma, etc.; Diseases related to bones, such as osteogenesis imperfecta, cartilage dysplasia, dwarfism, Crouzon syndrome, etc.; T-cell regulated inflammation and autoimmune diseases such as rheumatoid arthritis, collagen II arthritis, multiple sclerosis, systemic lupus erythematosus, psoriasis, juvenile-type diabetes, Sjogren's syndrome, thyroid disease, sarcoidosis inflammatory bowel disease, celiac disease, etc. The pharmaceutical composition of the present invention comprises a compound of the present invention or its pharmacologically acceptable salt thereof and a pharmacologically acceptable excipient or carrier within a safe and effective amount. The "safe and effective amount" refers to the amount of compound sufficient to significantly improve the condition without causing serious side effects. In general, the pharmaceutical compositions contain 1-2000 mg of the compound/agent of the present invention, more preferably, 5-200 mg of the compound/agent of the present invention. Preferably, the "one dose" is a capsule or tablet.

"Pharmaceutically acceptable carrier" means one or more compatible solid or liquid fillers or gel materials that are suitable for human use and must have sufficient purity and low enough toxicity. By "compatibility" it is meant herein that the components of the composition are capable of intermixing with the compounds of the present invention and between them without significantly reducing the efficacy of the compound. Examples of pharmaceutically acceptable carriers are cellulose and its derivatives (such as sodium carboxymethylcellulose, sodium ethylcellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyhydric alcohols (such as propylene glycol, glycerin, mannitol, sorbitol, etc.), emulsifiers (such as Tween®), and Wetting agents (such as sodium lauryl sulfate), colorants, flavoring agents, stabilizers, antioxidants, preservatives, pyrogen-free water, etc.

The mode of administration of the compound or pharmaceutical composition of the present invention is not particularly limited, and representative administration methods include, but are not limited to, oral, intratumoral, rectal, parenteral (intravenous, intramuscular or subcutaneous), and topical administration.

Solid dosage forms for oral administration include capsules, tablets, pills, powders, and granules. In these solid dosage forms, the active compound is admixed with at least one conventional inert excipient (or carrier), such as sodium citrate or dicalcium phosphate, or mixed with the following ingredients: (a) Fillers or compatibilizers such as starch, lactose, sucrose, glucose, mannitol and silicic acid; (b) Binders, for example, hydroxymethylcellulose, alginates, gelatin, polyvinylpyrrolidone, sucrose and acacia; (c) Moisturizers, for example, glycerin; (d) Disintegrating agents, for example, agar, calcium carbonate, potato or tapioca starch, alginic acid, certain complex silicates, and sodium carbonate; (e) Slow solvents, such as paraffin; (f) Absorption accelerators, for example, quaternary amine compounds; (g) Wetting agents such as cetyl alcohol and glycerol monostearate; (h) adsorbents, eg kaolin; and (i) Lubricants, for example, talc, calcium stearate, magnesium stearate, solid polyethylene glycol, sodium lauryl sulfate, or mixtures thereof. In capsules, tablets, and pills, the dosage form may also include a buffering agent.

Solid dosage forms such as tablets, dragees, capsules, pills, and granules can be prepared using coatings and shells, such as enteric coatings and other materials well known in the art. They may contain opacifying agents and the release of the active compound or compound in such compositions may be released in a certain part of the digestive tract in a delayed manner. Examples of embedding compositions that can be used are polymeric substances and waxy substances. If desired, the active compound may also be microencapsulated with one or more of the above excipients.

Liquid dosage forms for oral administration include pharmaceutically acceptable emulsions, solutions, suspensions, syrups or elixirs. In addition to the active compound, liquid dosage forms may contain inert diluents conventionally used in the art, such as water or other solvents, solubilizing agents and emulsifiers, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil, and sesame oil or a mixture of these substances.

In addition to these inert diluents, the compositions may also contain adjuvants such as wetting agents, emulsifying and suspending agents, sweeteners, flavoring agents and perfumes.

In addition to the active compound, the suspension may contain suspending agents such as, for example, ethoxylated isostearyl alcohols, polyoxyethylene sorbitol and sorbitan esters, microcrystalline cellulose, aluminum methoxide and agar or mixtures of these substances, and the like.

Compositions for parenteral injection may comprise physiologically acceptable sterile aqueous or nonaqueous solutions, dispersions, suspensions or emulsions, and sterile powders for reconstitution into sterile injectable solutions or dispersions. Suitable aqueous and nonaqueous vehicles, diluents, solvents or excipients include water, ethanol, polyols and suitable mixtures thereof.

Dosage forms for topical administration of the compounds of this invention include ointments, powders, patches, propellants, and inhalants. The active ingredient is admixed under sterile conditions with a physiologically acceptable carrier and any preservatives, buffers, or propellants that may be required.

The compounds of the present invention may be administered alone or in combination with other pharmaceutically acceptable compounds.

Where a pharmaceutical composition is used, a safe and effective amount of a compound of the invention is suitable for use in a mammal (e.g., a human) in need of treatment, wherein the dose is administered in an amount pharmaceutically efficacious and effective for administration to a human weighing 60 kg, The daily dose is usually 1 to 2000 mg, preferably 5 to 500 mg. Of course, specific doses should also consider factors such as the route of administration and the patient's health status, all of which are within the skills of skilled physicians.

The main advantages of the invention include:

1. Compounds of Formula I are provided.

2. A novel structure of FGFR inhibitor and its preparation and use are provided. The inhibitor can inhibit FGFR activity at very low concentrations.

3. A class of pharmaceutical compositions for the treatment of diseases associated with FGFR activity is provided.

The following further describes the present invention in combination with specific embodiments. It should be understood that these examples are only for illustrating the present invention and are not intended to limit the scope of the present invention. The experimental methods that do not specify the specific conditions in the following examples are generally based on conventional conditions or according to manufacturer's recommended conditions. Unless otherwise indicated, percentages and parts are by weight.

Example 1 Preparation of Compound 1

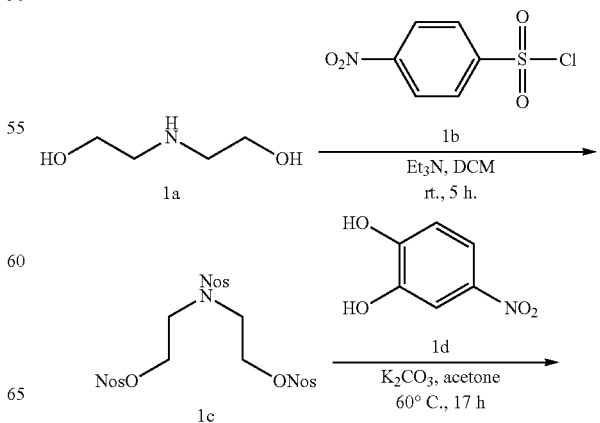

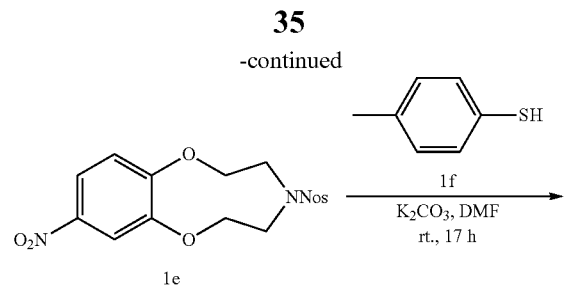

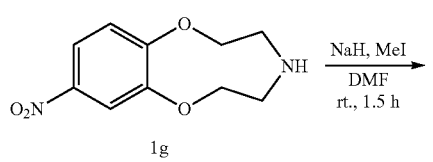

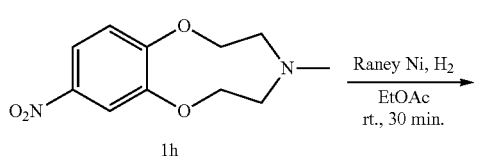

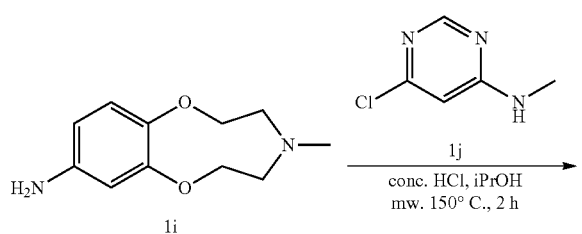

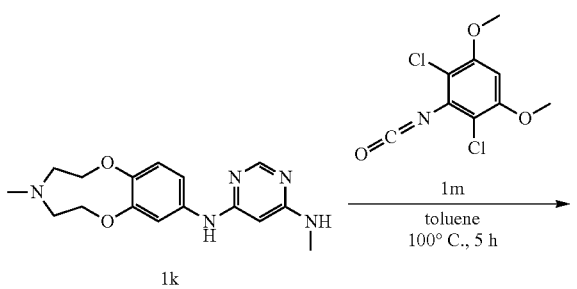

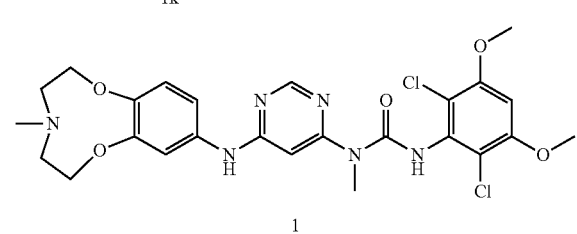

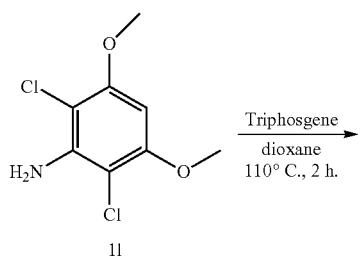

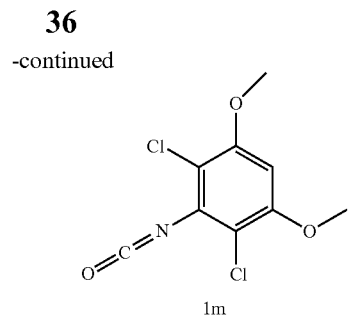

Compound 1a (5.00 g, 47.6 mmol) and triethylamine (24.1 g, 239 mmol) were dissolved in 200 mL of dichloromethane, and a solution of compound 1b (32.0 g, 144 mmol, dissolved in 100 mL of dichloromethane) was added dropwise with stirring at room temperature. After stirring at room temperature for 5 hours, TLC monitored the completion of the reaction, followed by the addition of 100 mL of water to quench the reaction. The organic phase was separated and the aqueous layer was extracted twice with dichloromethane. The combined organic phases were washed with water (100 mL) and brine (100 mL). The organic layer was dried over anhydrous sodium sulfate, then filtered, and the filtrate was concentrated under reduced pressure, the residue was purified via flash column chromatography (petroleum ether:ethyl acetate=1:1) to afford compound 1c as a yellow solid (15 g, yield 48%).

Compound 1d (1.0 g, 6.45 mmol), potassium carbonate (1.87 g, 13.6 mmol), and compound 1c (4.70 g, 7.11 mmol) were added to 20 mL, of acetone at room temperature under stirring, the resulting mixture was heated to reflux for 17 hours. After completion of the reaction, it was cooled to room temperature and filtered, and the filtrate was concentrated. The residue was purified via flash column chromatography (petroleum ether:ethyl acetate=1:1) to afford 1e (800 mg, yield 30%) as a light yellow liquid. MS 410.0 $[M+H]^+$, 431.9 $[M+Na]^+$.

At room temperature under stirring, compound 1e (100 mg, 0.24 mmol), potassium carbonate (101 mg, 0.73 mmol) and compound 1f (36 mg, 0.29 mmol) were added to 2 mL of N, N-dimethylformamide, the resulting mixture was stirred at room temperature for 17 hours. After the completion of the reaction, the mixture was concentrated under reduced pressure, then the residue was diluted with ethyl acetate (100 mL), washed with water (20 mL) and brine (20 mL) respectively, dried over anhydrous sodium sulfate, filtered. The filtrate was concentrated under reduced pressure to afford crude product. Crude product was purified via flash column chromatography (petroleum ether:ethyl acetate=1:1) to afford 1g (50 mg, yield 91%) as a light yellow liquid. MS 225.0 $(M+H)^+$.

Under an ice-bath cooling, sodium hydride (75 mg, 1.88 mmol, 60%) was slowly added to a solution of compound 1g (350 mg, 1.56 mmol) in N, N-dimethylformamide (5 mL), followed by addition of methyl iodide (244 mg, 1.72 mmol), the resulting mixture was stirred under such temperature for half an hour, then warmed to room temperature and stirred for 1.5 hour. The reaction was quenched by the addition of 20 mL of water, extracted with dichloromethane (100 mL). The organic layer was washed with water (20 mL) and brine (20 mL), dried over anhydrous sodium sulfate, filtered, the filtrate was concentrated under reduced pressure to afford compound 1h (280 mg, yield 75%) as a yellow solid. Crude product was used directly in next step reaction. MS 239.3 $(M+H)^+$.

Compound 1h (280 mg, 1.18 mmol) was dissolved in 20 mL of ethyl acetate at room temperature, then 100 mg of Raney nickel catalyst was added, and hydrogenation was carried out at room temperature under normal pressure for half an hour, and the reaction was monitored by TLC. The mixture was filtered through diatomite, and the filtrate was concentrated under reduced pressure to afford 1i (230 mg, yield 94%) as a brown liquid, the crude product was used directly in the next reaction. MS 209.0 $(M+H)^+$.

Compound 1i (180 mg, 0.864 mmol) and 1j (149 mg, 1.04 mmol) were dissolved in isopropanol (3 mL), then to the above solution was added concentrated HCl (0.2 mL). The mixture was placed in microwave reactor and heated to 150° C. for 2 hours, then cooled to room temperature, concentrated under reduced pressure to afford residue, which was purified via preparative HPLC to afford compound 1k (90 mg, yield 33%) as a white solid. $^1$H NMR (500 MHz, DMSO-$d_6$) δ 8.46 (br s, 1H), 7.99 (s, 1H), 6.86 (s, 1H), 6.78 (d, J=7.0 Hz, 1H), 6.72-6.59 (m, 2H), 5.56 (s, 1H), 4.17-4.06 (m, 2H), 3.57-3.45 (m, 2H), 3.42-3.28 (m, 4H), 3.26 (s, 3H), 2.69 (s, 3H); MS 316.3 $(M+H)^+$.

Compound 1l (221 mg, 1.0 mmol) and triphosgene (298 mg, 1.0 mmol) were added to 10 mL of anhydrous 1,4-dioxane at room temperature with stirring. The reaction mixture was heated to 110° C. for two hours. After the reaction was completed, it was cooled to room temperature and concentrated under reduced pressure to give compound 1m (230 mg, crude) as a pale yellow solid. The crude product was used in the next reaction without further purification.

Compound 1k (50 mg, 0.16 mmol) and 1m (197 mg, 0.79 mmol) were dissolved in anhydrous toluene (5 mL). The mixture was stirred and heated to 100° C. for 5 hours. The reaction was monitored by LC-MS and then cooled to room temperature after completion. The mixture was concentrated under reduced pressure and the residue was purified via preparative HPLC to afford compound 1 (26 mg, yield 29%) as a white solid. $^1$H NMR (400 MHz, CDCl$_3$) δ 12.67 (s, 1H), 8.34 (s, 1H), 6.79-6.73 (m, 2H), 6.72-6.63 (m, 2H), 6.53 (s, 1H), 6.11 (s, 1H), 4.27-4.23 (m, 2H), 3.93 (s, 6H), 3.64-3.58 (m, 2H), 3.52-3.43 (m, 4H), 3.38 (s, 3H), 3.32 (s, 3H); MS 562.6 $(M+H)^+$.

Example 2 Preparation of Compound 2

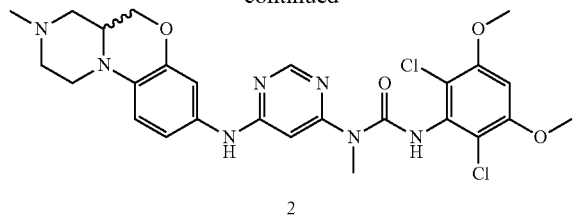

2

Compound 2a (37 mg, 0.17 mmol) and 1j (25 mg, 0.17 mmol) were dissolved in a 1:2 trifluoroacetic acid/water mixed solvent (2 mL). The reaction mixture was heated to 100° C. The reaction was monitored by LC-MS and the reaction was cooled to room temperature upon completion. The mixture was concentrated under reduced pressure, the residue was purified via preparative TLC (DCM:MeOH=20:1) to afford compound 2b (13 mg, yield 23%) as a pale solid. $^1$H NMR (400 MHz, CD$_3$OD) δ 7.96 (s, 1H), 6.89-6.72 (m, 3H), 5.62 (s, 1H), 4.27-4.20 (m, 1H), 4.00-3.91 (m, 1H), 3.79-3.71 (m, 1H), 3.16-3.05 (m, 1H), 3.03-2.95 (m, 1H), 2.93-2.85 (m, 11H), 2.78 (s, 3H), 2.79-2.68 (m, 1H), 2.36 (s, 3H), 2.36-2.25 (m, 1H), 1.97-1.84 (m, 1H); MS 327.2 $[M+H]^+$.

Compound 2b (13 mg, 0.04 mmol) and 1m (10 mg, 0.04 mmol) were dissolved in anhydrous toluene (1 mL). The reaction mixture was stirred and heated to 100° C. The reaction was monitored by LC-MS. After the reaction was complete, it was cooled to room temperature. It was concentrated under reduced pressure to give the residue. The residue was purified via preparative TLC (DCM:MeOH=20:1) to afford compound 2 (5.3 mg, yield 23%) as a light yellow solid. $^1$H NMR (400 MHz, CD$_3$OD) δ 8.34 (s, 1H), 6.99-6.83 (m, 3H), 6.80 (s, 1H), 6.35 (s, 1H), 4.28-4.20 (m, 1H), 4.02-3.93 (m, 1H), 3.95 (s, 6H), 3.80-3.71 (m, 1H), 3.35 (s, 3H), 3.16-3.04 (m, 1H), 3.05-2.88 (m, 1H), 2.93-2.85 (m, 1H), 2.79-2.69 (m, 1H), 2.38 (s, 3H), 2.35-2.25 (m, 1H), 1.98-1.84 (m, 1H); MS 574.2 $[M+H]^+$.

Example 3 Preparation of Compound 2S

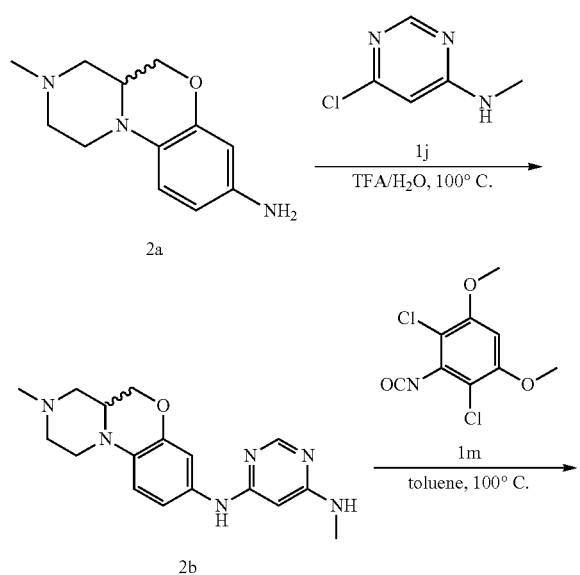

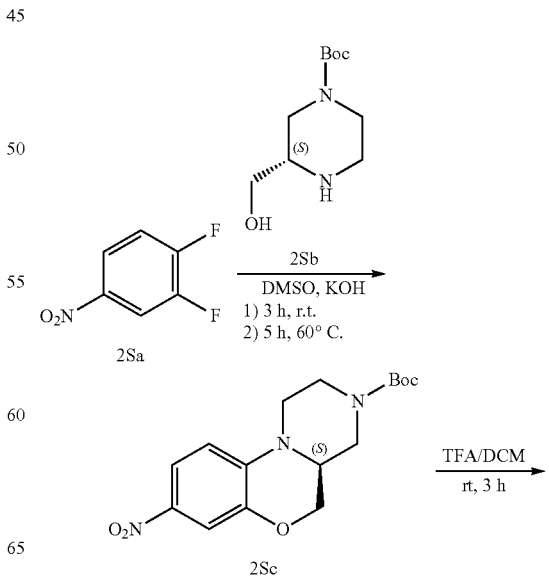

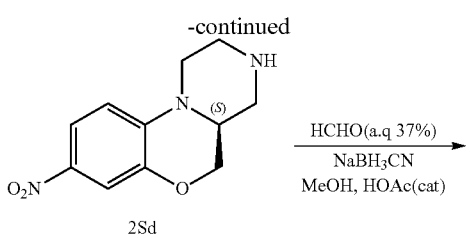

2Sd

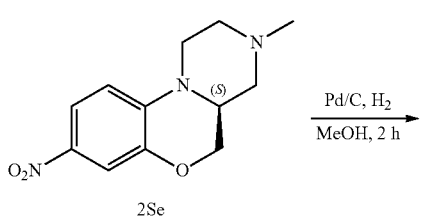

2Se

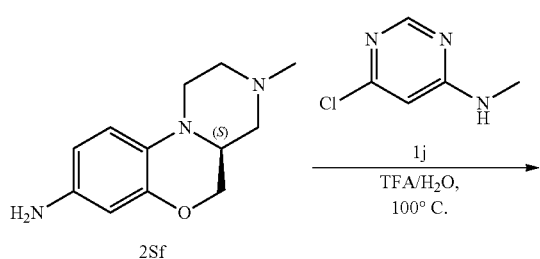

2Sf

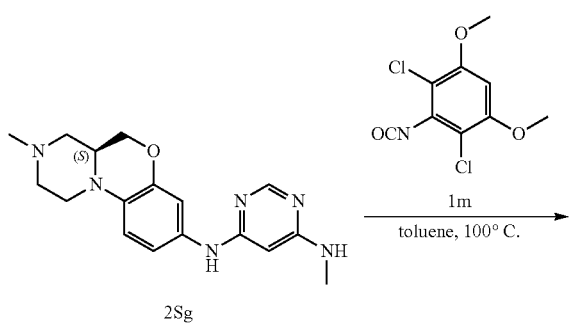

2Sg

2S

Compound 2Sa (3.0 g, 18.8 mmol), compound 2Sb (3.0 g, 13.8 mmol, 100% ee) and potassium hydroxide (2.4 g, 42.8 mmol) were added sequentially to 30 mL DMSO while stirring. The reaction mixture was heated to 30° C. for 3 hours and then warmed to 60° C. for 5 hours. After completion of the reaction, the system was cooled to room temperature, 300 mL of water was added, precipitation formed, and stirring was continued at room temperature overnight. Solid was collected via filtering, and was added to 25 mL of a mixed solvent consisting of 5:1 petroleum ether:ethyl acetate, and stirred at room temperature for half an hour. The solid was collected via filtering, and was dried to give compound 2Sc (3.0 g, yield 64%) as a yellow solid. MS 336.2 [M+H]$^+$.

Compound 2Sc (2.0 g, 6.0 mmol) was dissolved in 20 mL, dichloromethane, 5 mL trifluoroacetic acid was added at room temperature while stirring. After stirring at room temperature for 1 hour, TLC showed the reaction was complete. The reaction mixture was concentrated under reduced pressure to remove trifluoroacetic acid, and the residue was dissolved in 30 mL of dichloromethane, and pH was adjusted to 9-10 by using 1 M Na$_2$CO$_3$ aqueous solution. The organic layer was separated, the aqueous layer was extracted twice with dichloromethane, and the combined organic phases were washed with brine (30 mL) one time. The organic phase was dried over anhydrous sodium sulfate, filtered, and the filtrate was concentrated under reduced pressure to afford compound 2Sd (1.2 g, yield 86%) as a yellow solid. MS 236.1 [M+H]$^+$.

The compound 2Sd (1.2 g, 5.1 mmol) was dissolved in 20 mL of methanol, 37% aqueous formaldehyde (6 mL) was added, followed by 2 drops of acetic acid, and stirred at room temperature for 30 minutes. Sodium cyanoborohydride (0.8 g, 12.7 mmol) was added, and the mixture was stirred at room temperature for 3 hours, TLC showed the reaction was complete. The reaction mixture was concentrated under reduced pressure to afford crude product, which was purified via silica gel column chromatography (DCM MeOH=60:1) to afford 2Se (1.0 g, yield 79%) as a yellow solid. MS 250.2 [M+H]$^+$.

Compound 2Se (145 mg, 0.58 mmol) and 15 mg of Pd/C catalyst were added to 3 mL of methanol at room temperature. The reaction mixture was hydrogenated at room temperature under normal pressure for 1 hour, and the reaction was monitored by TLC till completion. The reaction mixture was filtered through celite, and the filtrate was concentrated under reduced pressure to afford compound 2Sf (100 mg, yield 79%) as a brown solid. Crude product was used directly in the next reaction. MS 220.2 [M+H]$^+$.

Compound 2Sf (70 mg, 0.32 mmol) and 1j (60 mg, 0.42 mmol) were dissolved in a 3:1 acetic acid/water mixture (1 mL), and the mixture was heated to 100° C. overnight. Upon completion indicated by LC-MS, the reaction mixture was cooled to room temperature, and concentrated under reduced pressure to afford residue, which was purified via preparative TLC (DCM:MeOH=40:1) to afford compound 2Sg (35 mg, yield 34%) as a light yellow solid. MS 327.3 [M+H]$^+$.

Compound 2Sg (35 mg, 0.11 mmol) and 1m (89 mg, 0.36 mmol) were dissolved in anhydrous toluene (1 mL), and the mixture was heated to reflux for 3 hours, the reaction was monitored by LC-MS till completion, then was cooled to room temperature, concentrated under reduced pressure to afford residue, which was purified via preparative TLC (DCM:MeOH=20:1, 0.5% ammonia) to afford compound 2S (15 mg, yield 24%) as a white solid. $^1$H NMR (CDCl$_3$, 400 Hz): δ 12.64 (s, 1H), 8.34 (s, 1H), 7.01 (s, 1H), 6.79-6.77 (m, 3H), 6.52 (s, 1H), 6.14 (s, 1H), 4.20 (dd, J=10.8 Hz, 2.8 Hz, 1H), 4.04-3.99 (m, 1H), 3.91 (s, 6H), 3.69-3.63 (m, 1H), 3.32 (s, 3H), 3.28-3.20 (m, 1H), 3.01-2.92 (m, 1H), 2.91-2.78 (m, 2H), 2.36 (s, 3H), 2.32-2.21 (m, 1H), 1.87-1.81 (m, 1H); MS 574.2 [M+H]$^+$; 100% ee.

Example 4 Preparation of Compound 2R

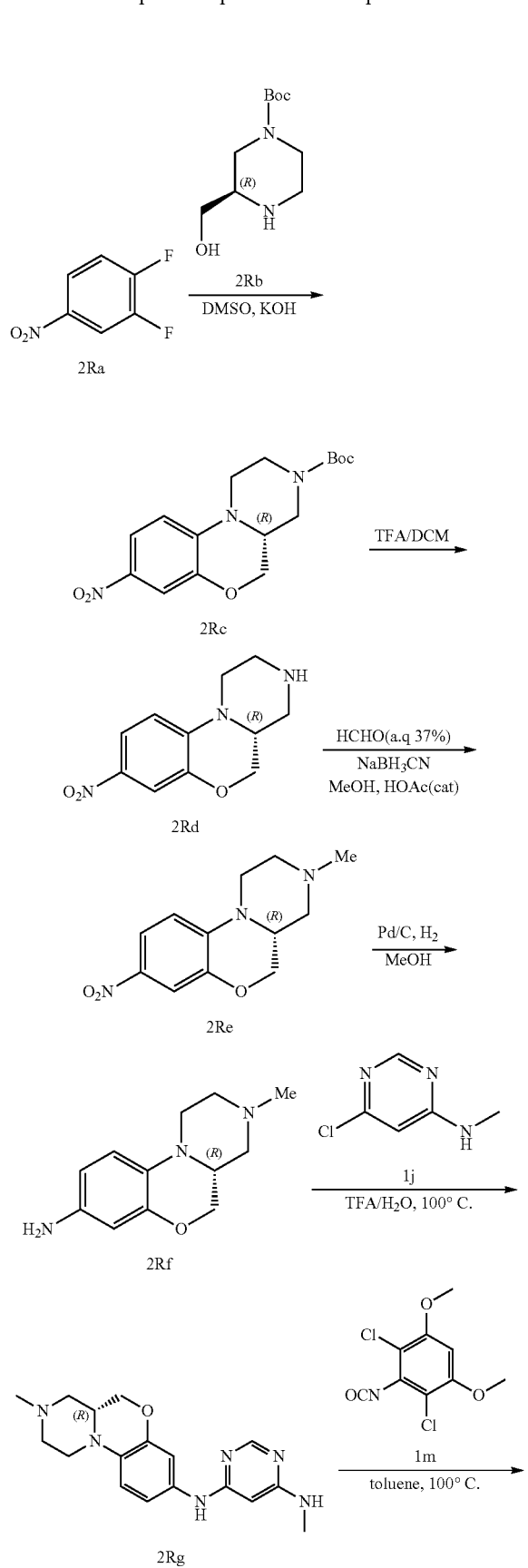

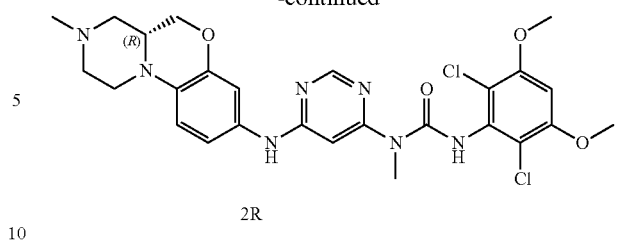

Referring to the preparation method of the intermediate 2Sf in Example 3, 2Rb (100% ee) was used as starting material to prepare intermediate 2Rf.

Compound 2Rf (100 mg, 0.46 mmol) and 1j (85 mg, 0.59 mmol) were dissolved in a 3:1 acetic acid/water mixture (2.0 mL), and the mixture was heated to 100° C. overnight while stirring. The reaction was monitored by LC-MS till completion, then was cooled to room temperature, concentrated under reduced pressure to afford residue, which was purified via preparative TLC (DCM:MeOH=40:1) to afford compound 2Rg (50 mg, yield 33%) as a light yellow solid. MS 327.2 [M+H]$^+$.

Compound 2Rg (50 mg, 0.15 mmol) and 1m (89 mg, 0.36 mmol) were dissolved in anhydrous toluene (1.0 mL), the reaction mixture was heated to reflux for 3 hours. Upon completion indicated by LC-MS, the reaction mixture was cooled to room temperature, concentrated under reduced pressure to afford residue, which was purified via preparative TLC (DCM:MeOH=1:20, 0.5% ammonia) to afford compound 2R(8 mg, yield 9%) as a white solid. $^1$H NMR (CDCl$_3$, 400 Hz): δ 12.64 (s, 1H), 8.34 (s, 1H), 6.90 (s, 1H), 6.79-6.76 (m, 3H), 6.52 (s, 1H), 6.14 (s, 1H), 4.20 (dd, J=10.8 Hz, 2.8 Hz, 1H), 4.04-3.99 (m, 1H), 3.91 (s, 6H), 3.69-3.63 (m, 1H), 3.32 (s, 3H), 3.28-3.19 (m, 1H), 3.01-2.91 (m, 1H), 2.91-2.78 (m, 2H), 2.36 (s, 3H), 2.32-2.21 (m, 1H), 1.87-1.81 (m, 1H); MS 574.2 [M+H]$^+$; 100% ee.

Example 5 Preparation of Compound 3

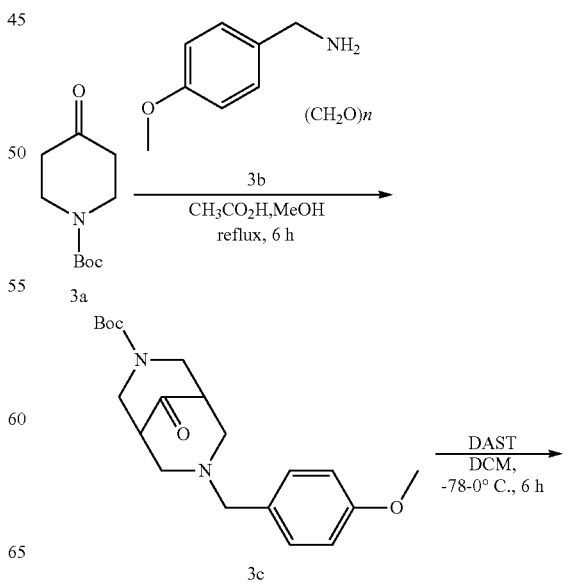

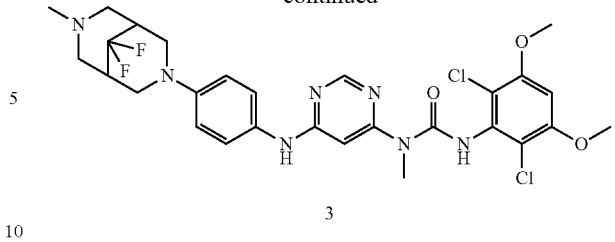

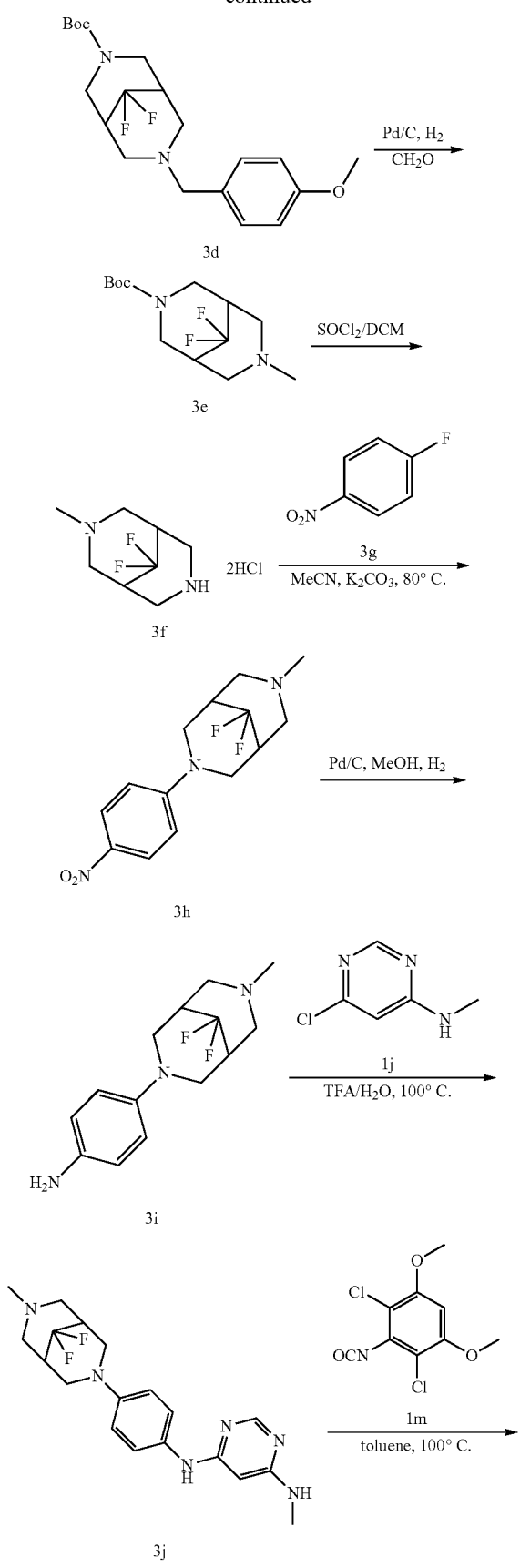

Compound 3a (10.0 g, 50.2 mmol), compound 3b (6.9 g, 50.2 mmol) and acetic acid (2.9 mL, 50.9 mmol) were added sequentially with stirring in 40 mL of methanol. Then, the above solution was added dropwise to a stirred solution of 3.3 g of paraformaldehyde in 10 mL of methanol, and the reaction mixture was heated under reflux for 1 hour, then 3.3 g of paraformaldehyde was further added, and reflux was continued for 5 hours. After completion of the reaction, the system was cooled to room temperature, 150 mL of diethyl ether was added, the organic phase was washed twice with 1M aqueous potassium hydroxide solution (80 mL×2), and the aqueous phase was extracted three times with diethyl ether (50 mL×3). The combined organic layer was dried over anhydrous magnesium sulfate, filtered, and then concentrated under reduced pressure to afford crude product, which was purified via silica gel column chromatography (3:1 petroleum ether ethyl acetate) to afford compound 3c (3.0 g, yield 72%) as a white solid. MS 361.4 [M+H]$^+$.

Compound 3c (5.0 g, 13.9 mmol) was dissolved in 50 mL of dichloromethane, cooled to −78° C. with dry ice-acetone solution system, and triethylamine trifluorosulfide (5.6 g, 34.75 mmol) was added dropwise over 30 minutes with stirring. The reaction mixture was stirred at −78° C. for half an hour, and then warmed to zero temperature for 6 hours, and the reaction was completed as shown by TLC. The reaction was quenched by the addition of aqueous ammonium chloride solution and extracted three times with dichloromethane (80 mL×3). The combined organic phase was washed once with saturated brine (30 mL), dried over anhydrous sodium sulfate, filtered, and concentrated under reduced pressure. The residue was purified via silica gel column chromatography (10:1 petroleum ether:ethyl acetate) to afford compound 3d (400 mg, yield 8.0%) as a colorless liquid. MS 383.3 [M+H]$^+$.

Compound 3d (400 mg, 1.1 mmol) and 10 mg of palladium on carbon catalyst were added to 5 mL of methanol at room temperature. The reaction mixture was hydrogenated at room temperature under normal pressure for 24 hours, then 3 mL of 37% aqueous formaldehyde solution was added, and the hydrogenation reaction was continued at room temperature for 24 hours. The reaction mixture was filtered through a pad of celite, and the filtrate was concentrated under reduced pressure, the residue was purified via silica gel column chromatography (20:1 petroleum:ethyl acetate) to afford compound 3e (100 mg, yield 35%) as a colorless oil. MS 277.4 [M+H]$^+$.

Compound 3e (100 mg, 0.4 mmol) was dissolved in 5 mL of ice-bath cooled dichloromethane, 0.3 mL, of thionyl chloride was then added with stirring. It was stirred at room temperature for 4 hours, the white solid formation was collected by filtering, the solid cake was rinsed with diethyl ether, dried under vacuum to afford compound 3f (55 mg, yield 78%). MS 236.1 [M+H]$^+$.

Compound 3f (150 mg, 0.4 mmol) and compound 3g (100 mg, 0.7 mmol) were dissolved in 10 mL of acetonitrile, and potassium carbonate (165 mg, 1.2 mmol) was added, then the mixture was heated to 80° C. with stirring, and the reaction was monitored by TLC till completion. The reaction mixture was concentrated under reduced pressure to yield crude product, which was purified via preparative TLC (2:1 petroleum:ethyl acetate) to afford compound 3h (120 mg, yield 67%) as a yellow solid. $^1$H NMR (400 MHz, CDCl$_3$) δ 8.15 (d, J=9.6 Hz, 2H), 6.70 (d, J=9.6 Hz, 2H), 3.95-3.85 (m, 2H), 3.64-3.55 (m, 2H), 2.90 (d, J=11.6 Hz, 2H), 2.57 (d, J=11.6 Hz, 2H), 2.44-2.34 (m, 2H), 2.18 (s, 3H); MS 298.2 [M+H]$^+$.

The compound 3h (120 mg, 0.40 mmol) and 10 mg of palladium carbon catalyst were added in 3 mL of methanol at room temperature. The reaction mixture was hydrogenated at 30° C. for 4 hours under normal pressure, and the reaction was completed by TLC. The reaction mixture was filtered through a pad of celite, the filtrate was concentrated under reduced pressure to afford compound 3i (95 mg, yield 89%) as a brown solid, which was used in the next reaction directly. MS 268.2 [M+H]$^+$.

Compound 3i (30 mg, 0.11 mmol) and 1j (35 mg, 0.24 mmol) were dissolved in a 1:2 trifluoroacetic acid/water mixture (2 mL), and the mixture was heated to 100° C., and the reaction was monitored by LC-MS. After completion, the reaction mixture was cooled to room temperature, concentrated under reduced pressure to yield residue, which was purified via preparative TLC (DCM:MeOH=1:20) to afford compound 3j (15 mg, yield 36%) as a white solid.

Compound 3j (15 mg, 0.04 mmol) and 1m (10 mg, 0.04 mmol) were dissolved in anhydrous toluene (I mL), and the mixture was heated to 100° C. with stirring, and the reaction was monitored by LC-MS. After completion, the reaction mixture was cooled to room temperature, concentrated under reduced pressure to yield residue, which was purified via preparative TLC (DCM:MeOH=1:20) to afford compound 3 (3.9 mg, yield 15%) as a white solid. $^1$H NMR (400 MHz, CDCl$_3$) δ 12.67 (s, 1H), 8.34 (s, 1H), 7.18 (d, J=8.8 Hz, 2H), 6.81 (d, J=8.8 Hz, 21H), 6.72 (s, 1H), 6.53 (s, 1H), 6.06 (s, 14), 3.93 (s, 6H), 3.84 (d, J=10.8 Hz, 2H), 3.49-3.40 (m, 2H), 3.30 (s, 3H), 3.00-2.93 (m, 2H), 2.63-2.55 (m, 2H), 2.41-2.33 (m, 2H), 2.22 (s, 3H); MS 622.3 [M+H]$^+$.

Example 6 Preparation of Compound 4S

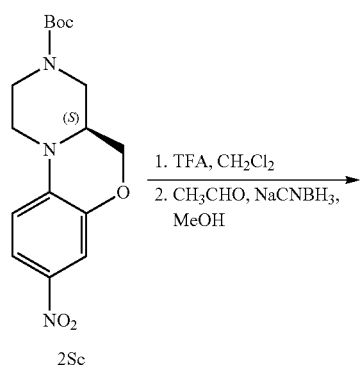

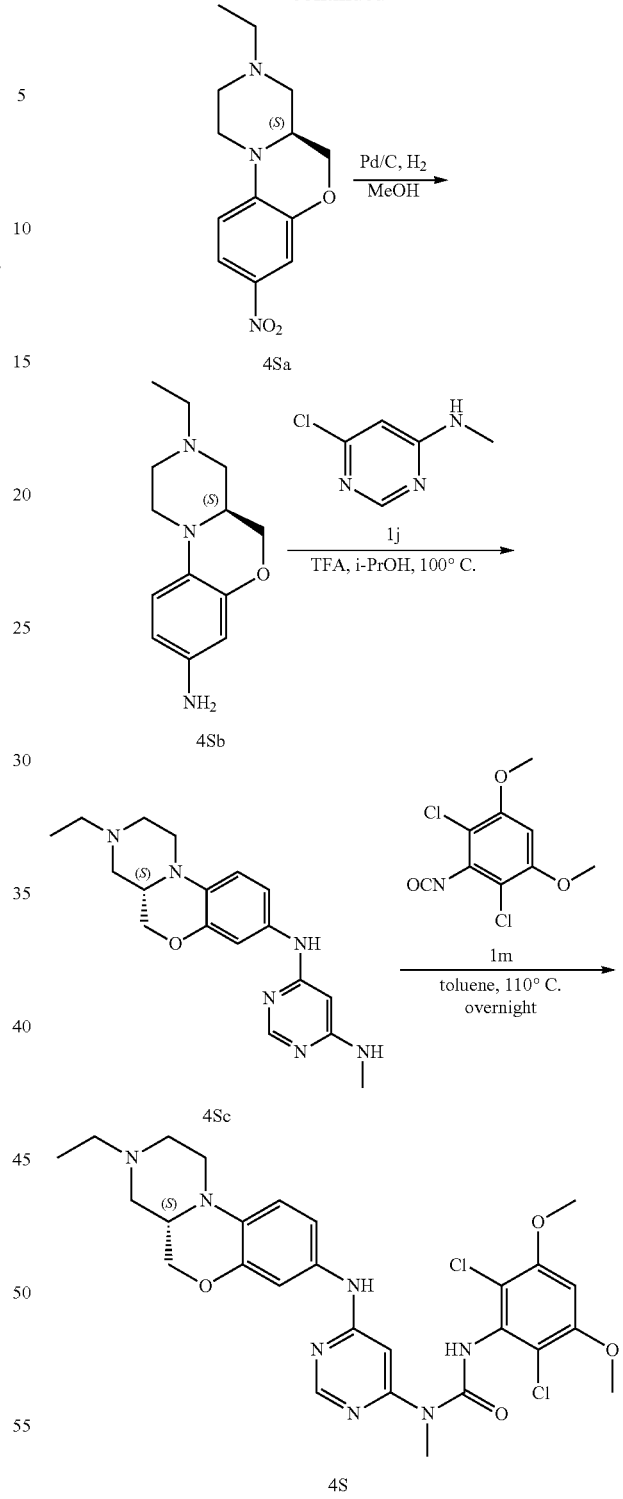

Compound 2Sc (150 mg, 0.448 mmol) was dissolved in dry dichloromethane (3 mL), trifluoroacetic acid (3 mL) was added with stirring. The reaction system was stirred at room temperature for 3 hours, and then the solvent and trifluoroacetic acid were removed under reduced pressure at 35° C. The resulting solid was dissolved in MeOH (6 mL), then acetaldehyde (99 mg, 2.247 mmol) and sodium cyanoborohydride (84 mg, 1.337 mmol) were added sequentially. The resulting mixture was stirred at room temperature for 1 hour.

TLC showed that the reaction was completed, the solvent was removed under reduced pressure at 35° C., and the obtained residue was dissolved in saturated sodium carbonate solution and extracted three times with ethyl acetate. The organic layers were combined and washed with brine, then dried over anhydrous sodium sulfate, and concentrated to yield the crude product, which was purified by silica gel column chromatography (dichloromethane/methanol=50/1 as eluting solvent) to afford compound 4Sa (110 mg, yield: 93%) as a yellow solid. $^1$H NMR (400 MHz, DMSO-$d_6$): δ 7.75 (dd, J=9.0 Hz, 2.6 Hz, 1H), 7.49 (d, J=2.8 Hz, 1H), 7.02 (d, J=9.2 Hz, 1H), 4.36 (dd, J=11.0 Hz, 3.0 Hz, 1H), 3.96-3.91 (m, 2H), 3.38-3.34 (m, 1H), 3.02-2.85 (m, 3H), 2.42-2.33 (m, 2H), 2.07-1.98 (m, 1H), 1.69 (dd, J=11.2 Hz, 10.8 Hz, 1H), 1.03 (t, J=7.2 Hz, 1H); MS 264.3 [M+H]$^+$.

Compound 4Sa (110 mg, 0.418 mmol) was placed in a 50 mL single-necked flask, dissolved in methanol (6 mL), then Pd/C (10%, 20 mg) was added. After replacing air with hydrogen gas, the reaction system was stirred at room temperature for 1 hour under a hydrogen atmosphere. TLC showed the completion of the reaction. The reaction mixture was filtered, and the filtrate was concentrated to afford compound 4Sb (95 mg) as a brown solid.

Compound 4Sb (95 mg, 0.407 mmol) and 1j (58 mg, 0.407 mmol) were dissolved in dry isopropanol (3 mL), trifluoroacetic acid (93 mg, 0.816 mmol) was added and the reaction system was heated to 100° C. and stirred overnight. The reaction solution was cooled to room temperature, then poured into a saturated aqueous solution of sodium bicarbonate and extracted with ethyl acetate three times. The combined organic layers were washed with brine, then dried over anhydrous sodium sulfate, concentrated to yield crude product, which was purified via preparative TLC (dichloromethane/methanol=15/1) to afford compound 4Sc (90 mg, yield: 65%) as a yellow solid. MS 341.2 [M+H]$^+$.

Compound 4Sc (68 mg, 0.200 mmol) and compound 1m (75 mg, 0.302 mmol) were dissolved in dry toluene (3 mL), and then the mixture was heated to 110° C. and stirred overnight. After completion, the reaction mixture was concentrated, the crude product was dissolved in small amount of dichloromethane-methanol mixture solvent, and purified via preparative TLC (dichloromethane/methanol=25/1) to afford compound 4S (46 mg, yield: 39%) as a white solid. $^1$H-NMR (400 MHz, DMSO-$d_6$): δ 12.03 (s, 1H), 9.41 (s, 1H), 8.39 (s, 1H), 7.05 (brs, 1H), 6.96 (dd, J=8.8 Hz, 2.4 Hz, 1H), 6.90 (s, 1H), 6.82 (d, J=8.8 Hz, 1H), 6.41 (s, 1H), 4.23 (dd, J=10.4 Hz, 2.8 Hz, 1H), 3.94 (s, 6H), 3.92-3.83 (m, 1H), 3.65-3.69 (m, 1H), 3.30 (s, 3H), 3.00-2.88 (m, 3H), 2.61-2.54 (m, 1H), 2.40-2.32 (m, 2H), 2.11-2.04 (m, 1H), 1.66 (dd, J=10.8 Hz, 10.4 Hz, 1H), 1.03 (t, J=7.2 Hz, 3H); MS 588.3 [M+H]$^+$.

Example 7 Preparation of Compound 4R

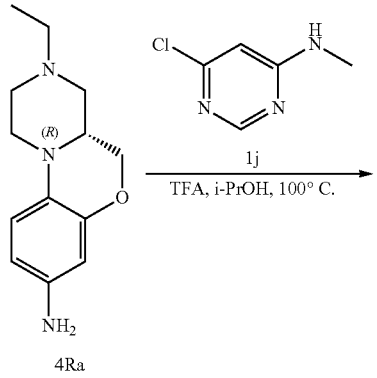

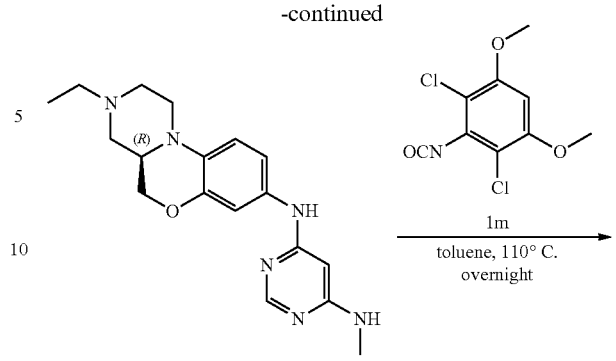

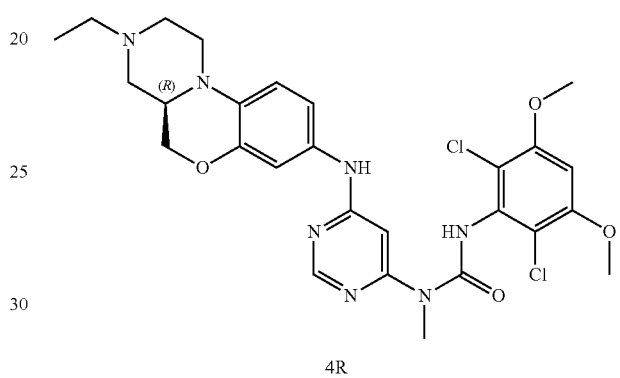

Compound 4Ra (60 mg, 0.258 mmol) and 1j (41 mg, 0.283 mmol) were dissolved in dry isopropanol (3 mL), then trifluoroacetic acid (32 mg, 0.283 mmol) was added. The mixture was placed in a sealed tube and heated to 100° C. under stirring overnight. The reaction mixture was cooled to room temperature, and then poured into a saturated aqueous solution of sodium bicarbonate, and the mixture was extracted three times with ethyl acetate. The combined organic layers were washed with brine, then dried over anhydrous sodium sulfate, and filtered. The filtrate was concentrated under reduced pressure to yield crude product, which was purified via preparative TLC (dichloromethane/methanol=15/1) to afford compound 4Rb (40 mg, yield: 46%) as a light brown solid. MS 341.2 [M+H]$^+$.

Compound 4Rb (40 mg, 0.118 mmol) and compound 1m (60 mg, 0.242 mmol) were dissolved in dry toluene (2 mL), then the mixture was stirred and heated to 110° C. overnight. TLC showed the completion of the reaction, the mixture was concentrated directly, crude product was dissolved in small amount of dichloromethane and methanol mixture, and purified via preparative TLC (dichloromethane/methanol=20/1) to afford compound 4R (10.1 mg, yield: 15%) as a white solid. $^1$H NMR (400 MHz, DMSO-$d_6$): δ 12.04 (s, 1H), 9.41 (s, 1H), 8.39 (s, 1H), 7.05 (s, 1H), 6.96 (dd, J=8.4 Hz, 1.6 Hz, 1H), 6.90 (s, 1H), 6.82 (d, J=8.8 Hz, 1H), 6.41 (s, 1H), 4.23 (dd, J=10.4 Hz, J=2.4 Hz, 1H), 3.94 (s, 6H), 3.94-3.84 (m, 1H), 3.67 (d, J=11.2 Hz, 1H), 3.30 (s, 3H), 3.02-2.86 (m, 3H), 2.63-2.54 (m, 1H), 2.41-2.30 (m, 2H), 2.12-2.02 (m, 1H), 1.66 (dd, J=10.8 Hz, 10.4 Hz, 1H), 1.03 (t, J=6.8 Hz, 3H); MS 588.2 [M+H]$^+$.

Example 8 Preparation of Compound 5S

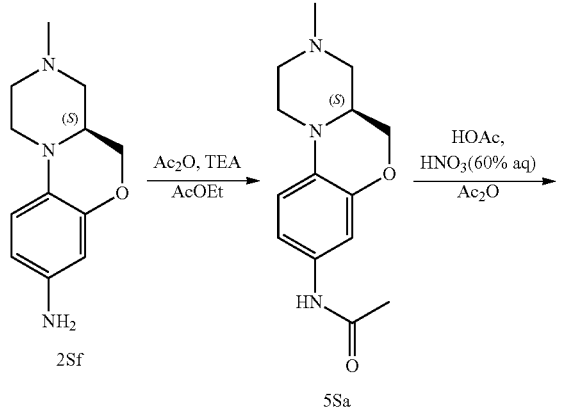

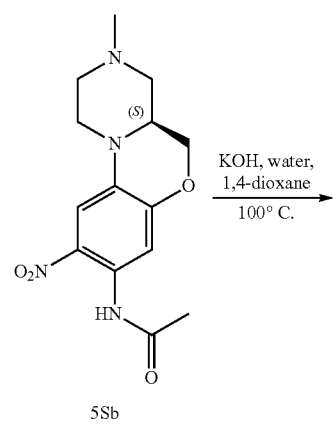

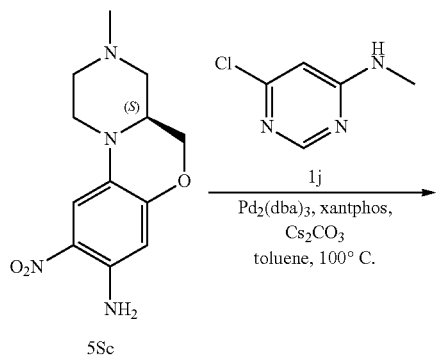

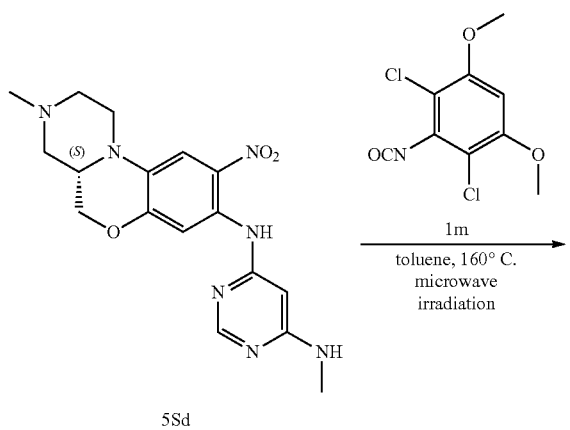

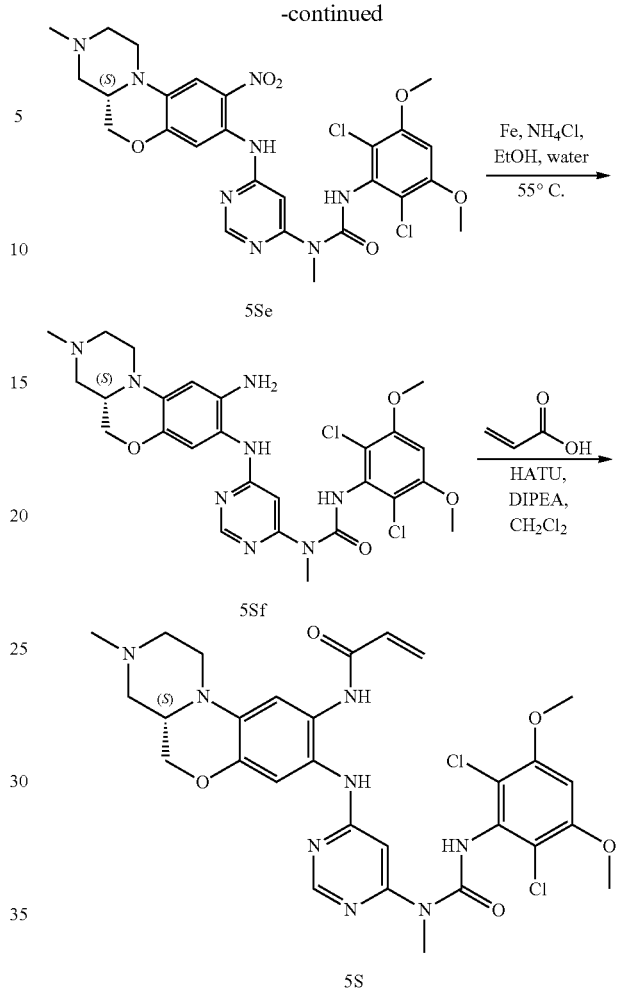

Compound 2Sf (200 mg, 0.913 mmol) and triethylamine (553 mg, 5.478 mmol) were dissolved in ethyl acetate (10 mL), and acetic anhydride (465 mg, 4.566 mmol) was added dropwise with stirring. The mixture was stirred at room temperature for 2 hours. The reaction was monitored by TLC till completion, and an appropriate amount of water was added to the reaction mixture, and the resulting mixture was stirred and the organic layer and aqueous layer were separated. The aqueous layer was extracted with ethyl acetate twice. The combined organic layers were washed with brine, separated, dried over anhydrous sodium sulfate, filtered, and concentrated to yield crude product, which was purified via preparative TLC (dichloromethane/methanol=20/1), to afford compound 5Sa (220 mg, yield: 92%). MS 262.2 $[M+H]^+$.

Compound 5Sa (210 mg, 0.805 mmol) was dissolved in acetic acid (7 mL), and then a mixed solution of 60% concentrated nitric acid and acetic anhydride (1/4) (obtained by this operation: 60% concentrated nitric acid was slowly added into an ice bath-cooled acetic anhydride, and the mixture was stirred for 10 minutes after completion) was slowly added at room temperature with stirring until the reaction liquid appeared yellow. The reaction was monitored by TLC until the starting material disappeared, then the reaction mixture was added dropwise to a solution of saturated sodium bicarbonate, extracted with ethyl acetate three times. The combined organic layers were washed with brine, separated, dried over anhydrous sodium sulfate, filtered, and concentrated to yield crude product, which was purified via preparative TLC (dichloromethane/methanol=60/1) to afford compound 5Sb (106 mg, yield: 43%) as a yellow solid. $^1$H-NMR (400 MHz, DMSO-d$_6$): δ 10.00 (brs, 1H), 7.43 (s, 1H), 7.20 (s, 1H), 4.37 (dd, J=10.8 Hz, 2.8 Hz, 1H), 4.01 (dd, J=10.8 Hz, 9.2 Hz, 1H), 3.73-3.69 (m, 1H), 3.15-3.06 (m, 1H), 2.90-2.81 (m, 2H), 2.73-2.66 (m, 1H), 2.22 (s, 3H), 2.11-1.98 (m, 1H), 2.05 (s, 3H), 1.68 (dd, J=10.8 Hz, 10.4 Hz, 1H).

Compound 5Sb (90 mg, 0.294 mmol) was dissolved in 1,4-dioxane (2 mL), then a solution of potassium hydroxide (105 mg, 1.875 mmol) in water (1.5 mL) was added dropwise). The reaction mixture was stirred at 100° C. for 4 hours. The TLC was used to monitor the disappearance of the starting material. The reaction mixture was adjusted to pH=7 with 2 M diluted hydrochloric acid, and then extracted three times with an appropriate amount of ethyl acetate. The combined organic phases were washed with brine, separate, dried over anhydrous sodium sulfate, filtered, and concentrated to yield crude product, which was further purified via preparative TLC (dichloromethane/methanol=20/1) to afford compound 5Sc as a orange solid (44 mg, yield: 57%). MS 265.2 [M+H]$^+$.

Compound 5Sc (50 mg, 0.189 mmol) was dissolved in dry toluene (5 mL), then 6-chloro-4-methylaminopyrimidine (1j, 32 mg, 0.227 mmol), cesium carbonate (123 mg, 0.379 mmol), Pd$_2$(dba)$_3$ (40 mg, 0.044 mmol) and xantphos (40 mg, 0.069 mmol) were added sequentially. After the reaction system was replaced with argon gas, it was stirred at 100° C. overnight. After the reaction is completed, it is filtered, concentrated, and the crude product purified via preparative TLC (dichloromethane/methanol=20/1) to afford compound 5Sd (45 mg, yield: 64%) as an orange solid. $^1$H NMR (400 MHz, DMSO-d$_6$): δ 9.42 (brs, 1H), 8.09 (s, 1H), 7.62 (brs, 1H), 7.48 (s, 1H), 7.01-6.99 (m, 1H), 5.90 (s, 1H), 4.38 (dd, J=10.6 Hz, 2.6 Hz, 1H), 4.03 (dd, J=10.4 Hz, 9.6 Hz, 1H), 3.70-3.67 (m, 1H), 3.12-3.05 (m, 1H), 2.92-2.81 (m, 2H), 2.74 (d, J=4.4 Hz, 3H), 2.72-2.65 (m, 1H), 2.23 (s, 3H), 2.13-2.06 (m, 1H), 1.69 (dd, J=10.8 Hz, 10.8 Hz, 1H); MS 372.2 [M+H]$^+$.

Compound 5Sd (21.5 mg, 0.058 mmol) and compound 1m (29 mg, 0.116 mmol) were dissolved in dry toluene (4 mL), then the reaction mixture was heated to 160° C. under microwave irradiation for 2 hours. After the reaction is completed, the reaction mixture was directly concentrated, and the crude product was dissolved in a small amount of a mixed solvent of dichloromethane and methanol, and then purified by preparative TLC (dichloromethane/methanol=50/1) to afford compound 5Se (4 mg, yield: 11%) as an orange solid. MS 619.3 [M+H]$^+$.

Compound 5Se (6 mg, 0.010 mmol) was dissolved in a mixed solution of ethanol and water (5/1) (2 mL), then iron powder (3 mg, 0.053 mmol) and ammonium chloride were added while stirring (3 mg, 0.056 mmol). The reaction solution was heated to 55° C. and stirred for 1.5 hours. After the reaction was completed, the reaction solution was filtered, concentrated, and the crude product was purified via preparative TLC (dichloromethane/methanol=20/1) to afford compound 5Sf (6 mg) as a light yellow solid. MS 589.3 [M+H]$^+$.

Acrylic acid (1 mg, 0.014 mmol) was dissolved in dry dichloromethane (1 mL), then HATU (5 mg, 0.013 mmol) and N,N-diisopropylethylamine (2 mg, 0.016 mmol) was added. The resulting mixture was stirred at room temperature for 10 min, a solution of compound 5Sf (6 mg, 0.010 mmol) in dichloromethane (0.5 mL) was added. The reaction mixture was stirred at room temperature for 1.5 hours. The reaction was monitored by TLC till completion, a few drops of methanol and water are added dropwise to the reaction solution, and the mixture was purified via preparative TLC (using dichloromethane/methanol=20/1 and ethyl acetate/methanol=6/1 as eluting solvent respectively) to afford compound 5S (1.9 mg, yield for two steps: 30%) as a white solid. $^1$H NMR (400 MHz, DMSO-d$_6$): δ 12.55 (s, 1H), 8.39 (s, 1H), 7.48 (d, J=8.8 Hz, 2H), 6.78 (brs, 1H), 6.69 (brs, 1H), 6.53 (s, 1H), 6.40 (d, J=16.8 Hz, 1H), 6.18 (dd, J=10.0 Hz, 16.8 Hz, 1H), 5.90 (brs, 1H), 5.76 (d, J=10.8 Hz, 1H), 4.20 (dd, J=10.8 Hz, 2.8 Hz, 1H), 4.01 (dd, J=10.8 Hz, 8.8 Hz, 1H), 3.93 (s, 6H), 3.71-3.67 (m, 1H), 3.31 (s, 3H), 3.26-3.23 (m, 1H), 2.96-2.86 (m, 2H), 2.83-2.80 (m, 1H), 2.35 (s, 3H), 2.26-2.20 (m, 1H), 1.82 (dd, J=10.8 Hz, 10.4 Hz, 1H); MS 643.2 [M+H]$^+$.

Example 9 Preparation of Compound 6R

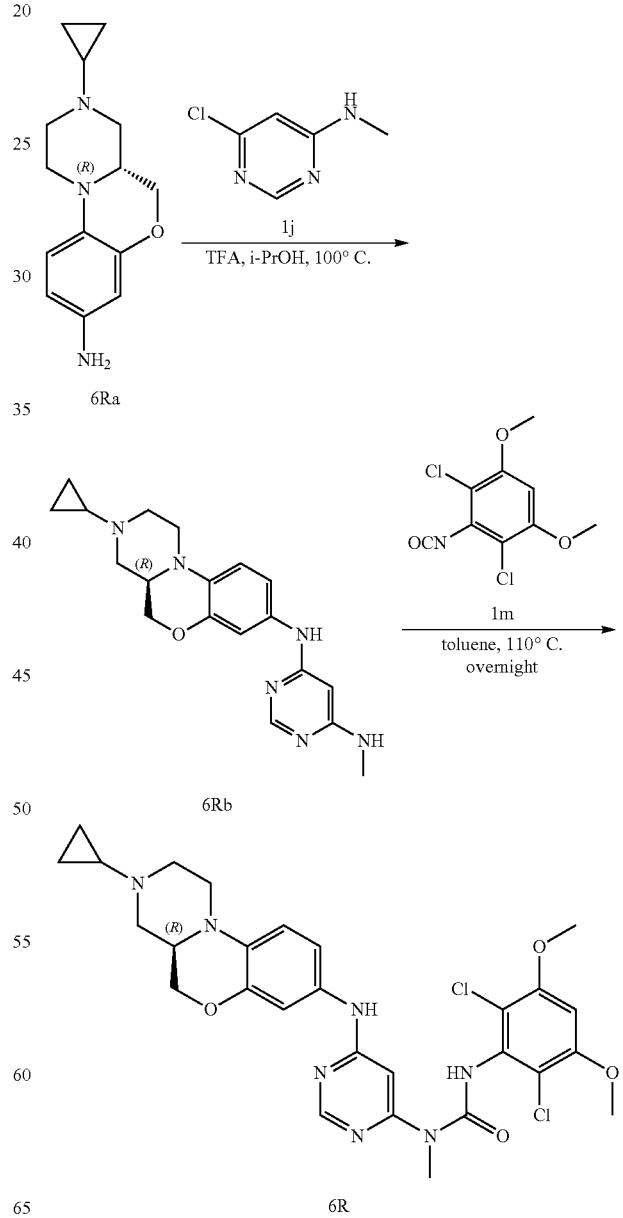

Compound 6Ra (100 mg, 0.41 mmol) and 1j (88 mg, 0.61 mmol) were dissolved in dry isopropyl alcohol (4 mL), then trifluoroacetic acid (139 mg, 1.22 mmol) was added, and the mixture was placed into a sealed tube and heated to 100° C. overnight with stirring. The reaction solution was cooled to room temperature, and then poured into a saturated aqueous solution of sodium bicarbonate, and the mixture was extracted three times with ethyl acetate. The organic layer was washed with brine, dried over anhydrous sodium sulfate and filtered. The crude product obtained by concentration of the filtrate under reduced pressure was separated by preparative TLC (dichloromethane/methanol=25/1) to afford compound 6Rb (70 mg, yield: 54%) as a light yellow solid. MS 353.3 [M+H]+.

Compound 6Rb (50 mg, 0.14 mmol) and compound 1m (70 mg, 0.28 mmol) were dissolved in dry toluene (2 mL), then the mixture was heated to 110° C. and stirred overnight. The reaction was monitored by TLC to completion, the reaction solution was directly concentrated under reduced pressure, and the crude product was dissolved in a small mixture of dichloromethane and methanol, and purified via preparative TLC (dichloromethane/methanol=20/1) to afford compound 6R (21 ng, yield: 25%) as a pale solid. $^1$H NMR (400 MHz, DMSO-d$_6$): δ 12.02 (s, 1H), 9.40 (s, 1H), 8.39 (s, 1H), 7.05 (s, 1H), 6.96 (d, J=8.8 Hz, 1H), 6.90 (s, 1H), 6.81 (d, J=8.8 Hz, 1H), 6.41 (s, 1H), 4.26-4.22 (m, 1H), 3.94 (s, 6H), 3.94-3.87 (m, 1H), 3.67 (d, J=12.0 Hz, 1H), 3.30 (s, 3H), 3.02-2.86 (m, 3H), 2.42-2.32 (m, 1H), 2.08 (s, 1H), 1.98 (dd, J=10.4 Hz, 10.0 Hz, 11), 1.70-1.62 (m, 1H), 0.48-0.41 (m, 2H), 0.40-0.31 (m, 2H); MS 600.2 [M+H]+.

Example 10 Preparation of Compound 7R

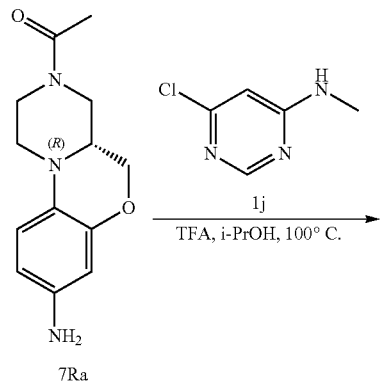

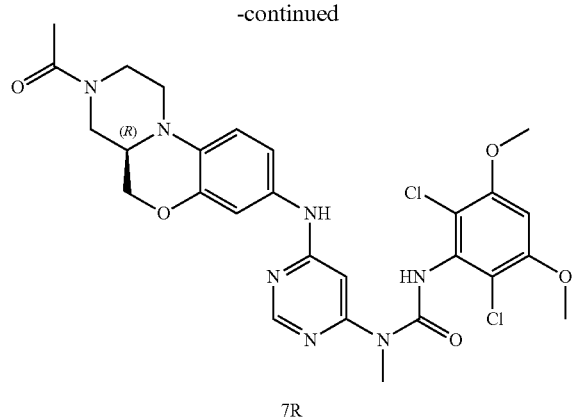

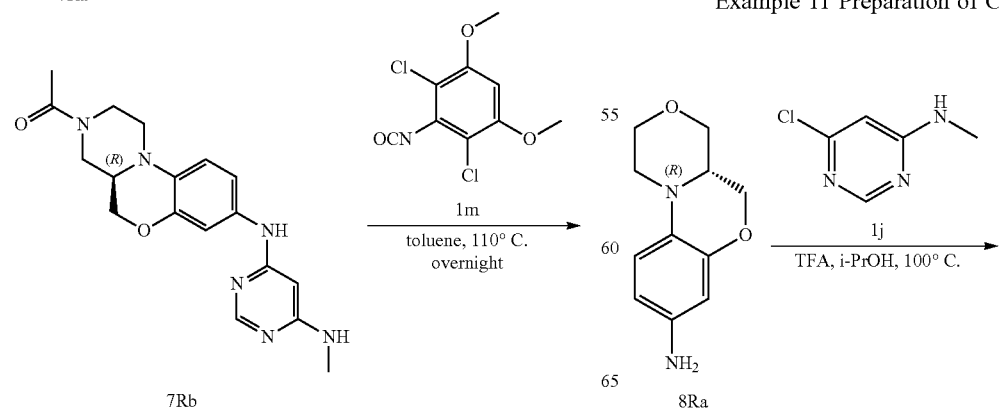

Compound 7Ra (120 mg, 0.48 mmol) and 1j (70 mg, 0.49 mmol) were dissolved in dry isopropyl alcohol (3 mL), then trifluoroacetic acid (84 mg, 0.74 mmol) was added, the mixture was placed in a sealed tube and heated to 100° C. overnight while stirring. The reaction solution was cooled to room temperature, and then poured into a saturated aqueous sodium bicarbonate solution, and the mixture was extracted three times with ethyl acetate. The combined organic layers were washed with brine, dried over anhydrous sodium sulfate, and filtered. The filtrate was concentrated under reduced pressure to obtain crude product, which was purified via preparative TLC (dichloromethane/methanol=20/1) to afford compound 7Rb (135 mg, yield: 78%) as a brown solid. MS 355.2 [M+H]+.

Compound 7Ra (53 mg, 0.150 mmol) and compound m (45 mg, 0.181 mmol) were dissolved in dry toluene (2 mL) and then the mixture was heated to 100° C. overnight while stirring. The reaction was monitored by TLC to completion, the reaction solution was directly concentrated under reduced pressure, and the crude product was dissolved in a small mixture of dichloromethane and methanol, and purified via preparative TLC (dichloromethane/methanol=20/1) to afford compound 7 (12.8 mg, yield: 14%) as a light yellow solid. $^1$H NMR (400 MHz, DMSO-d): δ 12.01 (s, 1H), 9.44 (s, 1H), 8.40 (s, 1H), 7.0 (d, J=9.6 Hz, 1H), 7.03-6.94 (m, 1H), 6.91-6.84 (m, 2H), 6.42 (s, 1H), 4.51-4.37 (m, 1H), 4.32 (dd, J=10.8 Hz, 2.4 Hz, 1H), 3.94 (s, 6H), 3.94-3.86 (m, 2H), 3.77 (d, J=12.0 Hz, 1H), 3.31 (s, 3H), 3.25-3.20 and 3.05-2.95 (two m, 1H), 2.92-2.81 (m, 1H), 2.79-2.55 (m, 1H), 2.47-2.30 (m, 1H), 2.06 and 2.05 (two s, 3H); MS 602.2 [M+H]+.

Example 11 Preparation of Compound 8R

Example 12 Preparation of Compound 9R

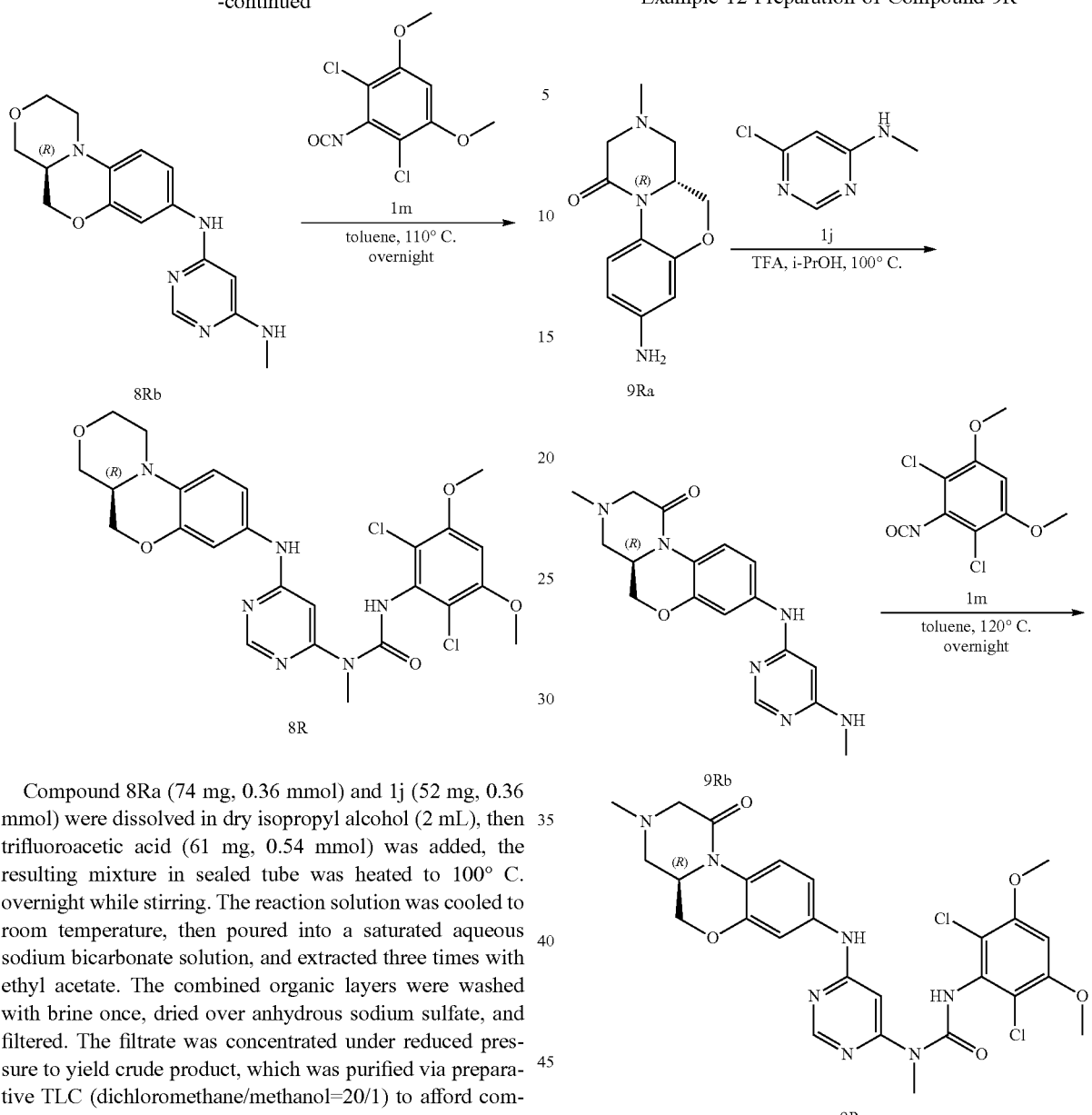

Compound 8Ra (74 mg, 0.36 mmol) and 1j (52 mg, 0.36 mmol) were dissolved in dry isopropyl alcohol (2 mL), then trifluoroacetic acid (61 mg, 0.54 mmol) was added, the resulting mixture in sealed tube was heated to 100° C. overnight while stirring. The reaction solution was cooled to room temperature, then poured into a saturated aqueous sodium bicarbonate solution, and extracted three times with ethyl acetate. The combined organic layers were washed with brine once, dried over anhydrous sodium sulfate, and filtered. The filtrate was concentrated under reduced pressure to yield crude product, which was purified via preparative TLC (dichloromethane/methanol=20/1) to afford compound 8Rb (75 mg, yield: 67%) as a brown solid. MS 314.2 [M+H]$^+$. Compound 8Rb (48 mg, 0.153 mmol) and compound 1m (45 mg, 0.181 mmol) were dissolved in dry toluene (2 mL), then the mixture was placed in a sealed tube and heated to 110° C. overnight while stirring. The reaction was monitored by TLC till completion, the mixture was concentrated directly under reduced pressure, the crude product was dissolved in a small amount of dichloromethane and methanol mix solvent, and purified via preparative TLC (dichloromethane/methanol=20/1) to afford compound 8R (6.74 mg, yield: 8%) as a light yellow solid. $^1$H NMR (400 MHz, DMSO-d$_6$): δ 12.02 (s, 1H), 9.43 (s, 11H), 8.40 (s, 1H), 7.08 (brs, 1H), 6.98 (dd, J=9.2 Hz, 2.4 Hz, 1H), 6.90 (s, 1H), 6.82 (d, J=9.2 Hz, 1H), 6.42 (s, 1H), 4.20 (dd, J=10.8 Hz, 2.4 Hz, 1H), 4.00-3.91 (m, 1H), 3.94 (s, 6H), 3.90-3.78 (m, 2H), 3.65-3.52 (m, 2H), 3.31 (s, 3H), 3.17 (dd, J=10.8 Hz, 10.4 Hz, 1H), 3.09-2.99 (m, 1H), 2.71-2.59 (m, 1H); MS 561.2 [M+H]$^+$.

Compound 9Ra (18 mg, 0.077 mmol) and 1j (13 mg, 0.091 mmol) were dissolved in dry isopropanol (1 mL), then trifluoroacetic acid (13 mg, 0.114 mmol) was added, the resulting mixture was placed in a sealed tube and heated to 100° C. overnight while stirring. The reaction mixture was cooled to room temperature, then poured into a saturated aqueous sodium bicarbonate solution, and extracted three times with ethyl acetate. The combined organic layers were washed with brine once, dried over sodium sulfate, and filtered. The filtrate was concentrated under reduced pressure, and the residue was purified via preparative TLC (dichloromethane/methanol=20/1) to afford compound 9Rb (10 mg, yield: 38%) as a yellow solid. MS 341.2 [M+H]$^+$.

Compound 9Rb (9 mg, 0.026 mmol) and compound 1m (60 mg, 0.242 mmol) were dissolved in dry toluene (1 mL), the resulting mixture was heated to 120° C. overnight while stirring. The reaction mixture was monitored by TLC till completion, then directly concentrated under reduced pressure to yield crude product, which was dissolved in a small amount of dichloromethane and methanol mixed solvent, and purified via preparative TLC (dichloromethane/methanol=20/1) to afford compound 9R (3.24 mg, yield: 21%) as a pale solid. $^1$H NMR (400 MHz, DMSO-d$_6$): δ 11.91 (s, 1H), 9.69 (s, 1H), 8.48 (s, 1H), 8.09 (d, J=9.2 Hz, 1H), 7.41 (d, J=2.0 Hz, 1H), 7.03 (dd, J=9.2 Hz, 2.4 Hz, 1H), 6.91 (s, 1H), 6.54 (s, 1H), 4.38 (dd, J=10.4 Hz, 1.6 Hz, 1H), 4.00 (dd, J=10.4 Hz, 10.0 Hz, 1H), 3.94 (s, 6H), 3.92-3.85 (m, 1H), 3.39-3.32 (m, 1H), 3.34 (s, 3H), 3.03-2.97 (m, 1H), 2.93 (d, J=16.4 Hz, 1H), 2.33 (dd, J=11.6 1-z, 8.4 Hz, 1H), 2.25 (s, 3H); MS 588.2 [M+H]$^+$.

Example 13 Preparation of Compound 10R

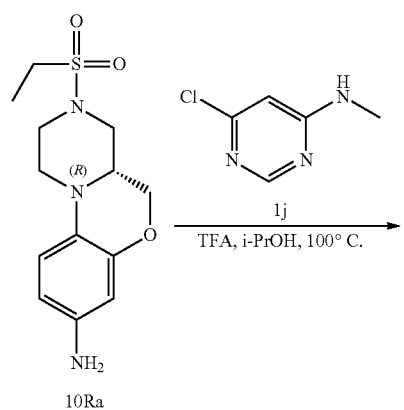

10Ra

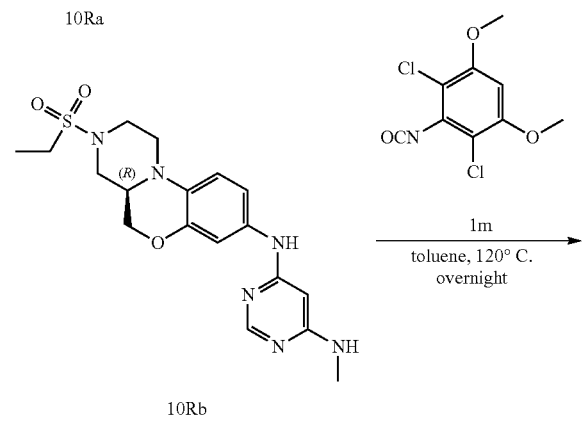

10Rb

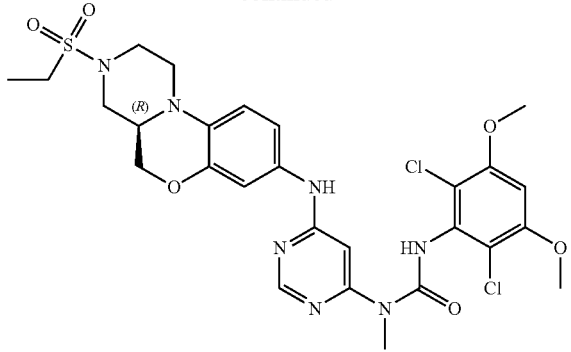

10R

Compound 10Ra (56 mg, 0.189 mmol) and 1j (30 mg, 0.207 mmol) were dissolved in dry isopropyl alcohol (3 mL), then trifluoroacetic acid (24 mg, 0.207 mmol) was added, the resulting mixture was placed in a sealed tube and heated to 100° C. overnight while stirring. The reaction mixture was cooled to room temperature, then poured into a saturated aqueous sodium bicarbonate solution, and extracted three times with ethyl acetate. The combined organic layers were washed with brine once, dried over sodium sulfate, and filtered. The filtrate was concentrated under reduced pressure, and the residue was purified via preparative TLC (dichloromethane/methanol=25/1) to afford compound 10Rb (48 mg, yield: 63%) as a light brown solid. MS 405.2 [M+H]$^+$.

Compound 10Rb (30 mg, 0.074 mmol) and compound 1m (60 mg, 0.242 mmol) were dissolved in dry toluene (2 mL), and the mixture was placed in a sealed tube and heated to 120° C. overnight while stirring. The reaction was monitored by TLC till completion, the mixture was concentrated directly under reduced pressure, the crude product was dissolved in a small amount of dichloromethane and methanol mixed solvent, and purified via preparative TLC (dichloromethane/methanol=20/1) to afford compound 10R (10.7 mg, yield: 22%) as a pale solid. $^1$H NMR (400 MHz, DMSO-d$_6$): δ 12.00 (s, 1H), 9.45 (s, 1H), 8.40 (s, 1H), 7.10 (brs, 1H), 7.00 (dd, J=8.8 Hz, 2.4 Hz, 1H), 6.93-6.84 (m, 2H), 6.43 (s, 1H), 4.33 (dd, J=10.8 Hz, 2.4 Hz, 1H), 3.94 (s, 6H), 3.94-3.81 (m, 2H), 3.68-3.61 (m, 2H), 3.31 (s, 3H), 3.14 (q, J=7.2 Hz, 2H), 3.09-2.96 (m, 2H), 2.71-2.60 (m, 2H), 1.23 (t, J=7.2 Hz, 3H); MS 652.2 [M+H]$^+$.

Example 14 Preparation of Compound 11S

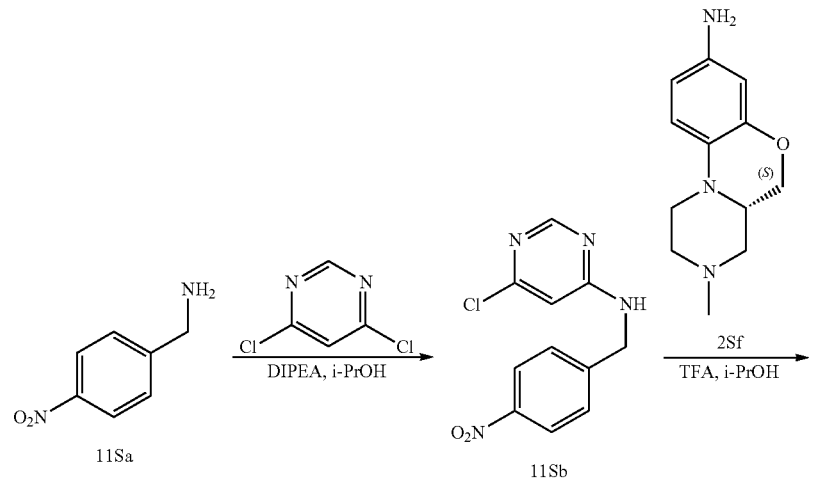

11Sa                11Sb

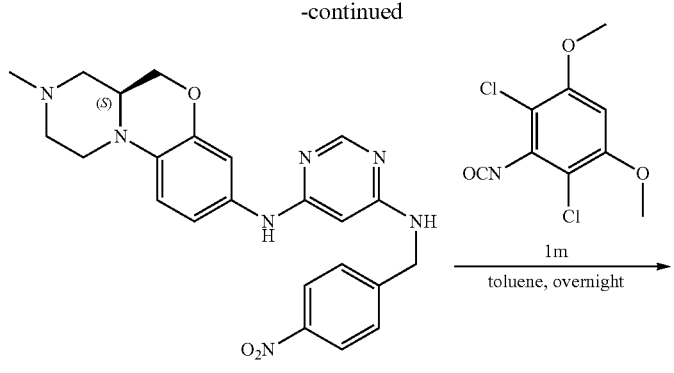
11Sc
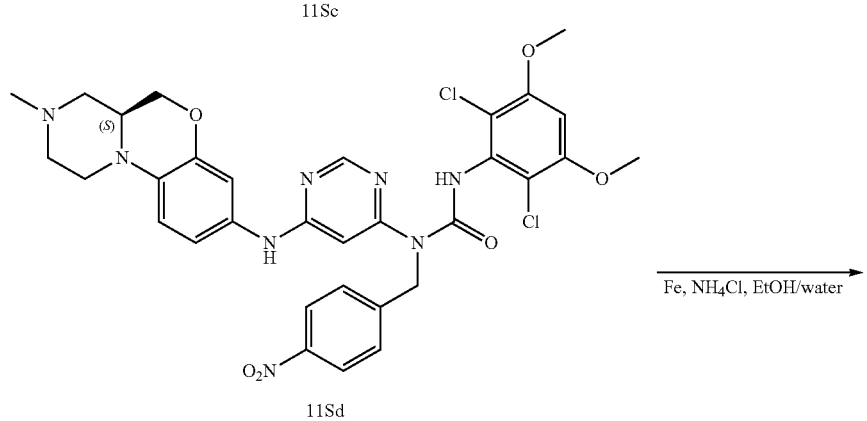
11Sd
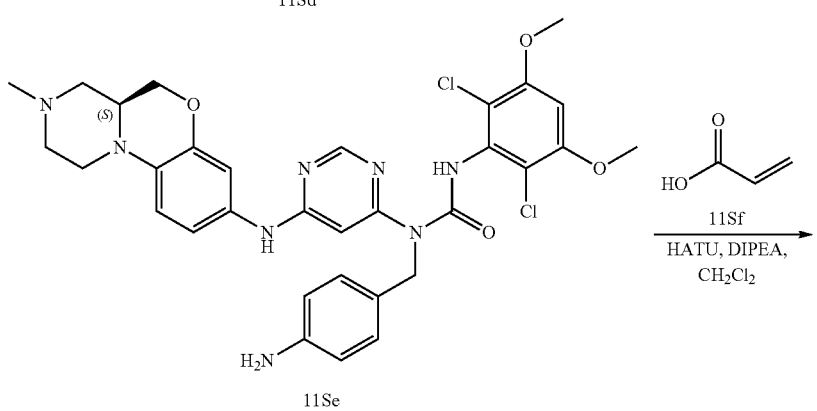
11Se
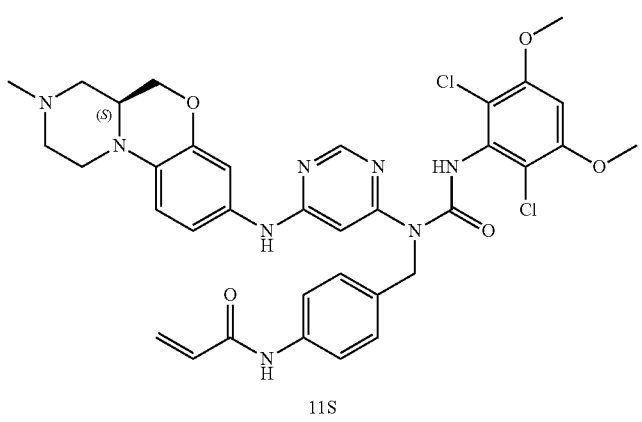
11S
4,6-Dichloropyrimidine (45 mg, 0.304 mmol), 4-nitrobenzylamine (46 mg, 0.304 mmol) and diisopropylethylamine (118 mg, 0.912 mmol) were added to isopropanol (5 mL). The mixture was heated to 60° C. overnight while stirring. The reaction was monitored by LCMS till completion, and the mixture was concentrated directly, the resulting residue was purified via preparative TLC (dichloromethane/methanol=30/1) to afford compound 11Sb (50 mg, yield: 62%) as a white solid. MS 265.2 [M+H]$^+$.

Compound 11Sb (50 mg, 0.189 mmol), 2Sf (50 mg, 0.227 mmol) and trifluoroacetic acid (32 mg, 0.284 mmol) were dissolved in isopropyl alcohol (2 mL), the resulting mixture was heated to 100° C. in a sealed tube and stirred overnight. The reaction was monitored by LCMS till completion, and was poured into 10 mL of saturated aqueous sodium bicarbonate solution while stirring, then extracted with ethyl acetate three times (10 mL×3), the combined organic layers were washed with brine (15 mL) once. The organic layer was dried over anhydrous sodium sulfate, and filtered. The filtrate was concentrated under reduced pressure to yield crude product, which was purified via preparative TLC (dichloromethane/methanol=20/1) to afford compound 11Sc (50 mg, yield: 59%) as a yellow solid. MS 448.2 [M+H]$^+$.

Compound 11Sc (40 mg, 0.089 mmol) and compound 1m (66 mg, 0.268 mmol) were dissolved in dry toluene (2 mL), then the reaction mixture was heated to 110° C. under microwave irradiation for 1 hour. The reaction was monitored by TLC till completion, and was concentrated directly, the resulting residue was dissolved in a small amount of dichloromethane and methanol mixed solvent, and purified via preparative TLC (dichloromethane/methanol=20/1) to afford compound 11Sd (28 mg, yield: 45%) as a light yellow solid. MS 695.2 [M+H]$^+$.

Compound 11Sd (28 mg, 0.040 mmol) was dissolved in a mixed solvent of ethanol and water (5/1, 2 mL), then iron powder (14 mg, 0.242 mmol) and ammonium chloride (13 mg, 0.242 mmol) were added while stirring. The reaction mixture was heated to 70° C. and stirred for 2 hours. The reaction was monitored by TLC till completion, and the mixture was filtered, and the filtrate was concentrated under reduced pressure, the residue was purified via preparative TLC (dichloromethane/methanol=20/1) to afford 11Se (23 mg, yield: 86%) as a light yellow solid. MS 665.2 [M+H]$^+$. Acrylic acid (7 mg, 0.104 mmol) was dissolved in dry dichloromethane (2 mL), then HATU (39 mg, 0.104 mmol) and N,N-diisopropylethylamine were added while stirring.

After stirred at room temperature for 10 min, a solution of compound 11Se (23 mg, 0.035 mmol) in dichloromethane (1 mL) was added. The reaction mixture was stirred at room temperature for 2 hours. The reaction was monitored by TLC till completion, and a few drops of methanol and water were added, the mixture was purified via preparative TLC (first eluted with dichloromethane/methanol=18/1, then with ethyl acetate/methanol=6/1) to afford compound 11S (2.2 mg, yield: 9%) as a pale solid. $^1$H NMR (400 MHz, CDCl$_3$): δ 12.84 (s, 1H), 8.34 (s, 1H), 7.57-7.49 (m, 2H), 7.45 (s, 1H), 7.18 (d, J=8.4 Hz, 2H), 6.73 (d, J=8.4 Hz, 1H), 6.64 (s, 1H), 6.56-6.52 (m, 2H), 6.45-6.36 (m, 2H), 6.27-6.17 (m, 1H), 6.08 (s, 1H), 5.75 (dd, J=10.0 Hz, J=1.6 Hz, 1H), 5.07 (s, 21:1), 4.24 (dd, J=10.4 Hz, 2.8 Hz, 1H), 4.04 (dd, J=10.4 Hz, 9.2 Hz, 1H), 3.93 (s, 6H), 3.78-3.70 (m, 1H), 3.27-3.18 (m, 1H), 2.99 (d, J=11.6 Hz, 1H), 2.90-2.80 (m, 2H), 2.38 (s, 3H), 2.34-2.24 (m, 1H), 1.87 (dd, J=11.2 Hz, 10.8 Hz, 1H); MS 719.2 [M+H]$^+$.

Example 15 Preparation of Compound 12R

Referring to the preparation method of compound 2R in Example 4, using 2Rc as an intermediate, compound 12R was obtained. MS 559.2 [M+H]$^+$.

Example 16

1. FGFR1, FGFR2, FGFR3, and FGFR4 Kinase Activity Inhibition Experiments

The FGFR1, FGFR2, FGFR3, and FGFR4 protein kinase activities were measured using the Caliper mobility shift assay. Compounds were solubilized in DMSO and diluted in kinase buffer. 5 L of compound at 5 times final concentration (10% DMSO) was added to a 384-well plate. 10 μL of a 2.5-fold enzyme (FGFR1, FGFR2, FGFR3, and FGFR4, respectively) solution was added and incubated at room temperature for 10 minutes, followed by the addition of 10 ML of a 2.5-fold substrate (FAM-labeled peptide and ATP) solution. The reaction was incubated for 30-60 minutes at 28° C., then stopped by adding 25 μL of stop solution (pH 7.5 100 mM HEPES, 0.015% Brij-35, 0.2% Coating Reagent #3, 50 mM EDTA). Conversion data was read on the Caliper EZ Reader II (Caliper Life Sciences). The conversion rate was converted into inhibition rate (% inhibition rate=(max−sample conversion rate)/(max−min)*100). Where max refers to the conversion of the DMSO control and min refers to the conversion of the non-enzymatic live control. With the compound concentration and inhibition rate plotted on the abscissa and the vertical axis, the curve was fitted using XLFit excel add-in version 4.3.1 software and the IC$_{50}$ was calculated.

The results showed that most of the tested compounds of formula I of the present invention exhibited inhibition of FGFR1, FGFR2 and FGFR3 kinase activity at IC$_{50}$ below 20 nM, and inhibition of FGFR4 kinase activity at IC$_{50}$ below 200 nM, and the activity of some representative compounds is shown in Table 1.

TABLE 1

| FGFR kinase activity inhibition (IC$_{50}$, nM) | | | | |
|---|---|---|---|---|
| | FGFR1 | FGFR2 | FGFR3 | FGFR4 |
| Compound 1 | <20 | | <20 | |
| Compound 2 | <10 | | <10 | |
| Compound 2S | <10 | <10 | <10 | <200 |
| Compound 2R | <10 | <10 | <10 | <200 |
| Compound 3 | <10 | | <10 | |
| Compound 4S | <10 | <10 | <10 | <200 |
| Compound 4R | <10 | <10 | | |
| Compound 5S | >1000 | >1000 | >1000 | <20 |
| Compound 6R | <20 | <50 | | |
| Compound 7R | <10 | <10 | | |
| Compound 8R | <20 | <20 | | |
| Compound 9R | <10 | <10 | | |
| Compound 10R | <50 | <50 | | |
| Compound 11S | <50 | | | <200 |

2. Compounds' Inhibition Test Against SNU-16 Tumor Cell Proliferation

SNU-16 cell suspension was adjusted to 5.56×10e4/mL with RPMI 1640 medium. Add 90 μL of cell suspension to 96-well cell culture plates per well for a final cell concentration of 5000 cells/well. The test compound was dissolved in DMSO as a 10 mM stock solution. The 3× series of serial dilutions were prepared with stock and DMSO and then diluted 100-fold with media. Finally, 10 μL of the corresponding 10× solution was added to each well of each cell, and each drug concentration was 2 replicates. The final concentration of each compound was 1000 nM, 333.3 nM, 111.1 nM, 37.04 nM, 12.35 nM, 4.115 nM, 1.372 nM, 0.457 nM, 0.152 nM, the final concentration of DMSO per well is 0.1%. Place in a 37° C., 5% CO$_2$ incubator for 72 hours. After 72 hours of drug treatment, add 50 μL (1/2 culture volume) of CTG solution that has been previously thawed and equilibrated to room temperature per well according to CTG instructions, mix for 2 minutes using a microplate shaker, and allow to stand at room temperature for 10 minutes. The Envision 2104 reader was used to determine the fluorescence signal value. Cell viability formula: $V_{sample}/V_{vehicle\ control} \times 100\%$ for calculation. Wherein $V_{sample}$ is the reading of the drug treatment group and, $V_{vehicle\ control}$ is the average of the solvent control group. Using the GraphPad Prism 5.0 software, a sigmoidal dose-survival curve was plotted using a non-linear regression model and $IC_{50}$ values were calculated. The activity of some representative compounds is shown in Table 2.

TABLE 2

Inhibits of SNU-16 tumor cells proliferation ($IC_{50}$, nM)

| | SNU-16 |
|---|---|
| Compound 2S | <10 |
| Compound 2R | <10 |
| Compound 3 | <10 |
| Compound 4S | <10 |

All references mentioned in this application are incorporated by reference in this application, as if each were incorporated by reference individually. In addition, it should be understood that after reading the above description of the present invention, those skilled in the art can make various changes or modifications to the present invention, and these equivalent forms also fall within the scope defined by the appended claims of the present application.

The invention claimed is:

1. A compound of formula (I), or a pharmaceutically acceptable salt, hydrate, or solvate thereof:

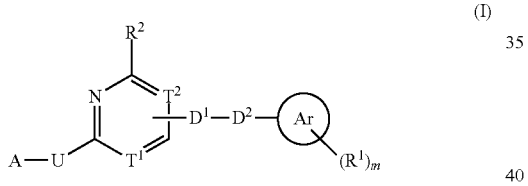

(I)

wherein:
$T^1$ is N or $CR^{13}$;
$T^2$ is N, $CR^{13}$, or C connected to $D^1$;
wherein each $R^{13}$ is independently selected from the group consisting of hydrogen, halogen, $C_{1-4}$ alkyl, CN, $OR^5$, or $NR^5R^6$;
$D^1$ is $NR^3$, O, S, $CHR^4$; wherein $R^3$ is hydrogen, $C_{1-4}$ alkyl, or $(CH_2)_p$—V—$(CH_2)_qN(R^6)C(O)R^5$; $R^4$ is hydrogen or $C_{1-4}$ alkyl;
$D^2$ is $C(O)NR^4$, $C(O)O$, $CHR^4$, $NR^4$, O, or S;
Ar is aryl or heteroaryl;
each $R^1$ is independently selected from the group consisting of hydrogen, halogen, $C_{1-4}$ alkyl, $C_{2-4}$ alkenyl, $C_{2-4}$ alkynyl, halogenated $C_{1-4}$ alkyl, CN, $OR^5$, $SR^5$, $NO_2$, $NR^5R^6$, $OCOR^5$, $C(O)R^5$, $C(O)OR^5$, $C(O)NR^5R^6$, $N(R^6)C(O)NR^5R^6$, $N(R^6)C(O)R^5$, $S(O)_2NHR^5$, $S(O)_2R^5$, or $NHS(O)_2R^5$;
m is 0, 1, 2, 3, 4 or 5;
$R^2$ is hydrogen, halogen, $C_1$-4 alkyl, CN, $OR^5$, or $NR^5R^6$;
U is $NR^7$ or O; wherein $R^7$ is hydrogen or $C_{1-4}$ alkyl;
each p and q is independently 0, 1, 2, 3, or 4;
V is a divalent group, when V is $CHR^5$, $C_{3-8}$ cycloalkyl, 3- to 8-membered heterocyclic, aryl, or heteroaryl, p is 0-4, q is 0-4; when V is CH=CH or C≡C, p is 1-4, q is 1-4; when V is O or $NR^{15}$, p is 2-4, q is 2-4; wherein $R^{15}$ is hydrogen, $C_{1-4}$ alkyl, $C(O)R^5$, or $S(O)_2R^5$;

each of $R^5$ and $R^6$ is independently hydrogen, $C_{1-8}$ alkyl, $C_{2-8}$ alkenyl, $C_{2-8}$ alkynyl, $C_{3-8}$ cycloalkyl, 3- to 8-membered heterocyclic, aryl, or heteroaryl;
or $R^5$ and $R^6$ together with the nitrogen atom they attached form a 3- to 8-membered cyclic structure (saturated or partially saturated) which optionally containing 0-2 additional heteroatoms selected from N, O or S;
A is formula (II):

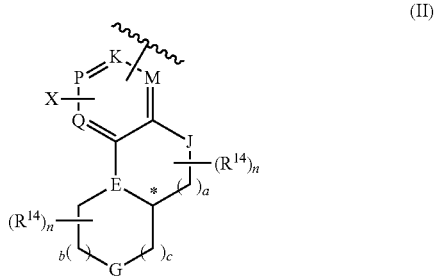

(II)

or A is a group selected from the group consisting of:

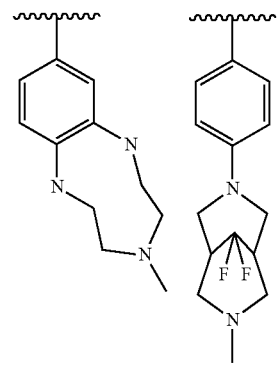

wherein:
"⁓" represents the attaching point of A to U in formula (I);
"*" indicates a chiral center;
each K, M, P and Q is independently N or $CR^8$;
X is hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;
each $R^{14}$ is independently hydrogen, halogen, $C_{1-4}$ alkyl, $C_{2-4}$ alkenyl, $C_{2-4}$ alkynyl, $C_{3-8}$ cycloalkyl, 3- to 8-membered heterocyclic, CN, $OR^5$, $SR^5$, $NR^5R^6$, $C(O)R^5$, $C(O)OR^5$, $C(O)NR^5R^6$, $OC(O)R^5$, $NR^6C(O)R^5$, $S(O)_2R^5$, =O, or =S;
n is 0, 1 or 2;
each a, b, and c is independently 0, 1, 2, or 3;
J is O, S, $CR^9R^{10}$, $NR^{12}$, or C(O);
E is N or $CR^{11}$;
G is $NR^{12}$, O, S, S(O), $S(O)_2$, or $CR^9R^{10}$;
wherein,
each $R^8$ is independently hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;
each $R^9$ or $R^{10}$ is independently hydrogen, halogen, or $C_{1-4}$ alkyl;
$R^{11}$ is hydrogen, $C_{1-4}$ alkyl, or $OR^5$;

$R^{12}$ is hydrogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;

wherein each of the above-mentioned alkyl, alkenyl, alkynyl, cycloalkyl, heterocyclic group, aryl, heteroaryl is optionally and each independently substituted with 1-3 substituents, and the substituents are each independently selected from halogen, $C_{1-4}$ alkyl, $C_{2-4}$ alkenyl, $C_{2-4}$ alkynyl, $C_{3-8}$ cycloalkyl, 3- to 8-membered heterocyclic group, aryl, heteroaryl, CN, $NO_2$, $OR^5$, $SR^5$, $NR^5R^6$, $C(O)R^5$, $C(O)OR^5$, $C(O)NR^5R^6$, $NC(O)NR^5R^6$, $N(R^6)C(O)R^5$, or $S(O)_2R^5$;

unless otherwise specified, the above aryl group is aryl group having 6 to 12 carbon atoms; and the heteroaryl group is 5- to 15-membered heteroaryl group.

2. The compound of claim 1, A is formula (II):

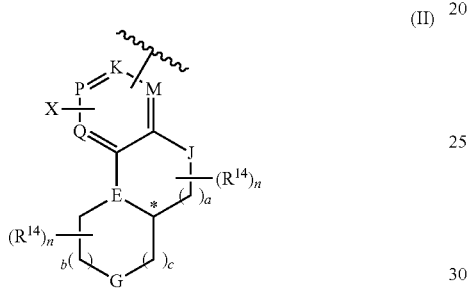

(II)

wherein:
each of K, M, P, and Q is independently N or $CR^8$; wherein, when any one of K, M, P, or Q is $CR^8$, the $R^8$ is X; and when any one of K, M, P, or Q is connected to U, it is C, i.e., $R^8$ does not exist;

X is hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;

while the remaining groups are defined as in claim 1.

3. The compound of claim 1, wherein P or K in formula (II) is C which is attached to U.

4. The compound according to claim 1, wherein $R^{14}$ is $R^{17}$ or $R^{18}$, and formula (II) is:

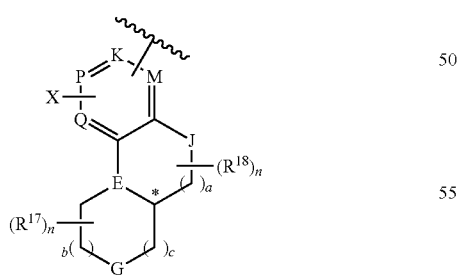

wherein:
$R^{17}$ is hydrogen, halogen, $C_{1-4}$ alkyl, $C_{3-8}$ cycloalkyl, $OR^5$, $NR^5R^6$, $C(O)R^5$, $C(O)OR^5$, $C(O)NR^5R^6$, $OC(O)R^5$, $NR^6C(O)R^5$, $S(O)_2R^5$ or =O;

$R^{18}$ is hydrogen, halogen, $C_{1-4}$ alkyl, $OR^5$ or =O.

5. The compound of claim 1, wherein the compound of formula (I) is a compound of Formula (III):

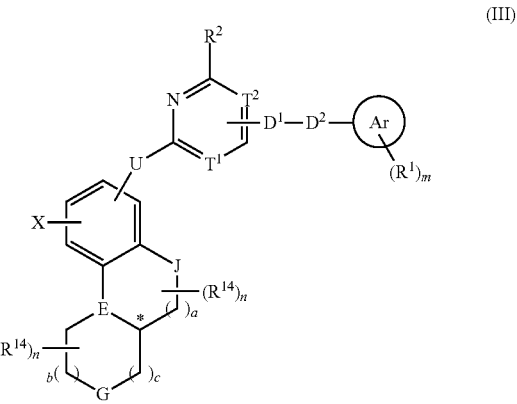

(III)

while the remaining groups are defined as in claim 1.

6. The compound of claim 1, wherein:
J is O, $CR^9R^{10}$, $NR^{12}$, or C(O);
E is N or $CR^{11}$;
G is $NR^{12}$ or O;
each $R^9$ or $R^{10}$ is independently hydrogen, halogen, or $C_{1-4}$ alkyl;
$R^{11}$ is hydrogen or $C_{1-4}$ alkyl;
$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;
while the other groups are defined as in claim 1.

7. The compound of claim 1, wherein the compound of formula (I) is a compound of Formula (VI):

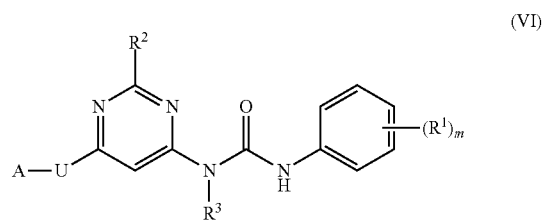

(VI)

A is a group selected from the group consisting of:

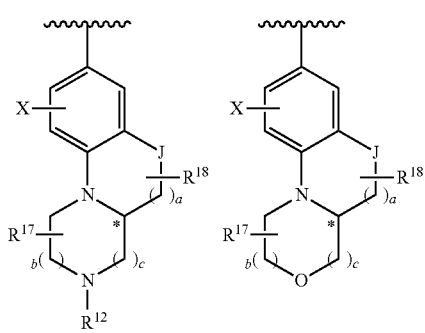

-continued wherein:
" 〰 " represents the attaching point of A to U in formula (I);
"*" indicates a chiral center;
X is hydrogen, halogen, $C_{1-4}$ alkyl, CN, $OR^5$, $NO_2$, $NR^5R^6$, $C(O)OR^5$, $C(O)NR^5R^6$, $N(R^6)C(O)R^5$ or $S(O)_2R^5$;
each of a, b and c is independently 1 or 2;
J is O, $CR^9R^{10}$, $NR^{12}$, or C(O);
wherein, each $R^9$ or $R^{10}$ is independently hydrogen, halogen, or $C_{1-4}$ alkyl;
$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;
$R^5$ and $R^6$ are respectively defined as in claim 1;
$R^{17}$ is hydrogen, $C_{1-4}$ alkyl, or =O;
$R^{18}$ is hydrogen, $C_{1-4}$ alkyl, or =O;
$R^1$, m, $R^2$, $R^3$, and U are respectively defined as in claim 1.

8. The compound of claim 1, wherein the A is selected from the group consisting of:

wherein:
" 〰 " represents the attaching point of A to U in formula (II);
"*" indicates a chiral center;
X is hydrogen, halogen, $C_{1-4}$ alkyl, $NO_2$, $NR^5R^6$, or $N(R^6)C(O)R^5$;
J is O, $CR^9R^{10}$, $NR^{12}$, or C(O); wherein each $R^9$ or $R^{10}$ is independently hydrogen, fluoro, or $C_{1-4}$ alkyl;
$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;

$R^{17}$ is hydrogen, $C_{1-4}$ alkyl, or =O;
while the remaining groups are defined as above.

9. The compound of claim 1, wherein the A is a group selected from the group consisting of:

wherein:
" 〰 " represents the attaching point of A to U in formula (II);
"*" indicates a chiral center;
X is hydrogen, halogen, $C_{1-4}$ alkyl, $NO_2$, $NR^5R^6$, or $N(R^6)C(O)R^5$;
$R^{12}$ is hydrogen, $C_{1-4}$ alkyl, $C_{1-4}$ haloalkyl, $C_{3-8}$ cycloalkyl, 3- to 8-heterocyclyl, aryl, heteroaryl, $C(O)R^5$, $C(O)OR^5$, $C(O)NR^5R^6$, or $S(O)_2R^5$;
while the other groups are defined as in claim 1.

10. The compound of claim 1, wherein,
U is $NR^7$, wherein $R^7$ is hydrogen or $C_{1-4}$ alkyl; and/or
$R^2$ is hydrogen or $C_{1-4}$ alkyl; and/or
$R^3$ is hydrogen, $C_{1-4}$ alkyl, or $(CH_2)_p$—V—$(CH_2)_p N(R^6)$ $C(O)R^5$; wherein V is $CHR^5$, $C_{3-8}$ cycloalkyl, 3- to 8-membered heterocyclic group, aryl, or heteroaryl; each p and q are each independently 0, 1, or 2; and/or
each $R^1$ is each independently selected from the group consisting of hydrogen, halogen, $C_{1-4}$ alkyl, $C_{1-4}$ haloalkyl, CN, $OR^5$, $NR^5R^6$, or $N(R^6)C(O)R^5$;
m is 0, 1, 2, 3, 4 or 5;
while the remaining groups are defined as above.

11. The compound of claim 1, wherein,
U is NH; and/or
$R^2$ is hydrogen; and/or
$R^3$ is $C_{1-4}$ alkyl, or $(CH_2)_p$—V—$(CH_2)_q N(R^6)C(O)R^5$; wherein V is phenyl; p is 0, 1, 2 or 3; q is 0; and/or
each $R^1$ is independently selected from the group consisting of hydrogen, halogen, $C_{1-4}$ alkyl, $C_{1-4}$ haloalkyl, CN, $C_{1-4}$ alkoxy;
m is 0, 1, 2, 3, or 4;
while the remaining groups are defined as above.

12. The compound of claim 1, wherein the compound of formula (I) is a compound of formula (V):

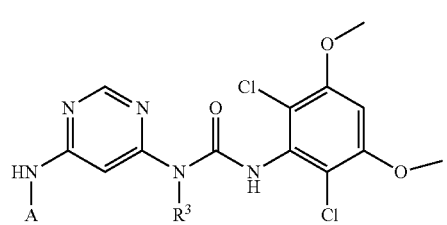
(V)

A is a group selected from the group consisting of:

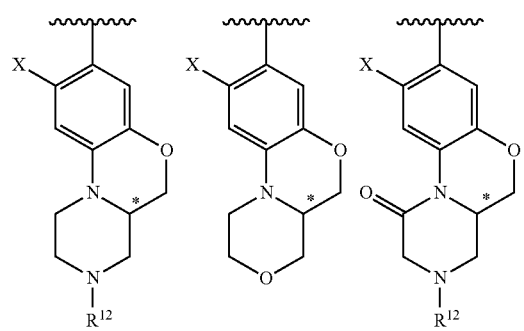

wherein,

" ︵︵︵ " represents the attach point of A to the rest of the molecule in formula (V);

X is hydrogen or NHC(O)CH=CH$_2$;

R$^{12}$ is hydrogen, C$_{1-4}$ alkyl, C$_{3-8}$ cycloalkyl, C(O)C$_{1-4}$ alkyl, or S(O)$_2$C$_{1-4}$ alkyl;

R$^3$ is methyl or formula (VI)

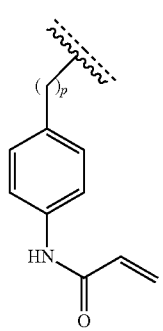
(VI)

p = 0, 1, 2, 3 wherein " ︵ " represents the attaching point of R$^3$ to the nitrogen atom in formula (V);

with the proviso that when X is NHC(O)CH=CH$_2$, R$^3$ is not formula (VI); when R$^3$ is formula (VI), X is not NHC(O)CH=CH$_2$.

13. The compound of claim 1, wherein the compound of formula (I) is a compound of Formula (V):

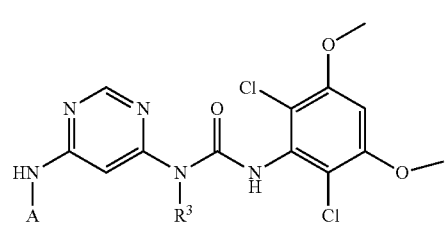
(V)

A is a group selected from the group consisting of:

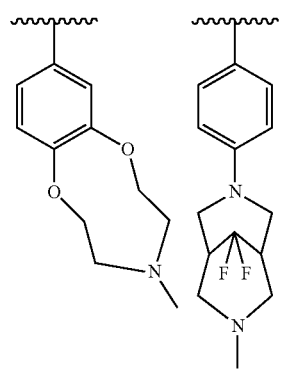

R$^3$ is methyl or formula (VI)

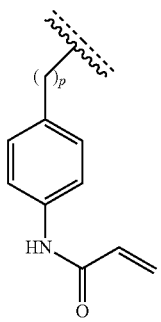
(VI)

p = 0, 1, 2, 3 wherein " ︵ " represents the attach point of R$^3$ to the nitrogen atom in formula (V).

14. The compound of claim 1, wherein compound is selected from the following group:

1

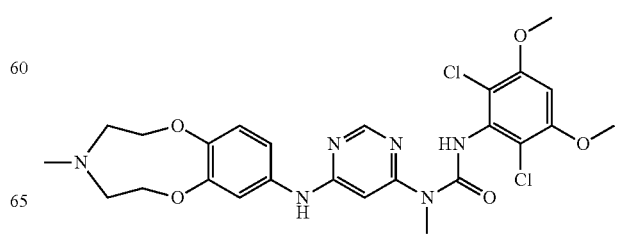

2
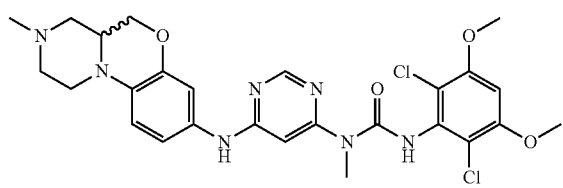
2S
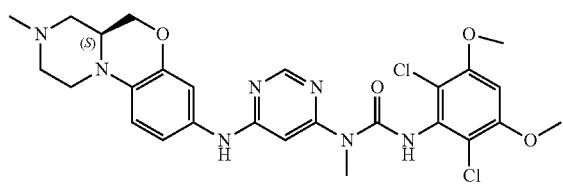
2R
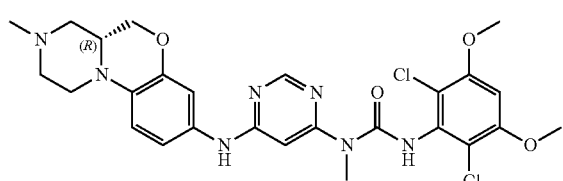
3
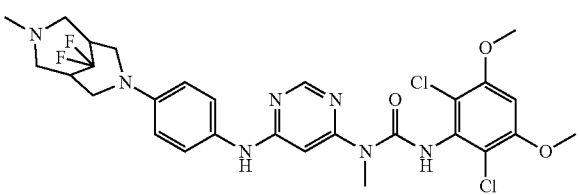
4S
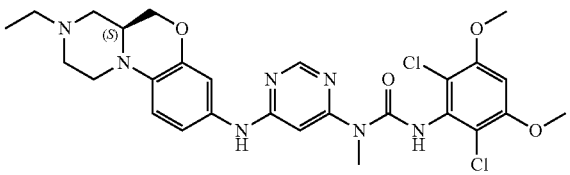
4R
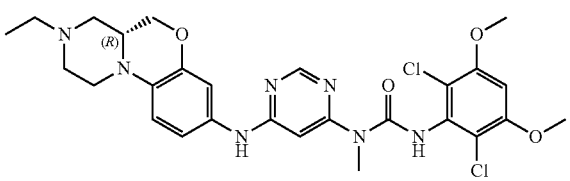
5S
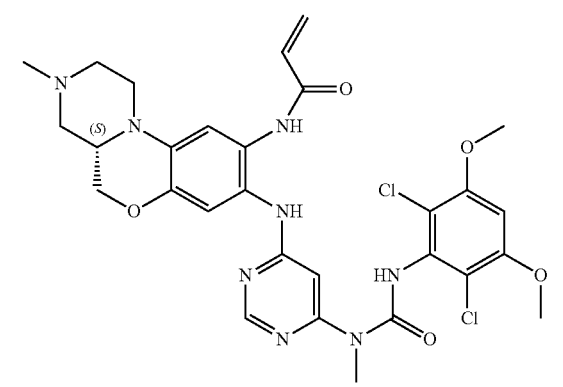
5R
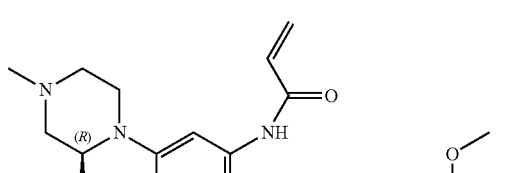
6S
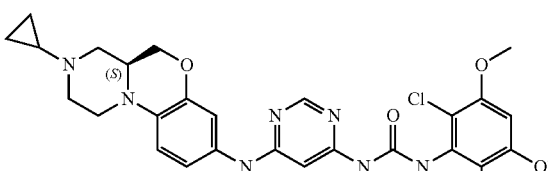
6R
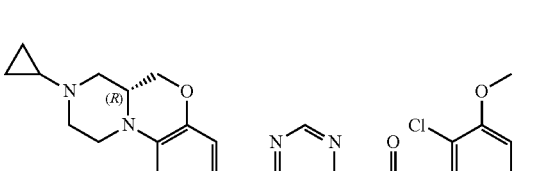
7S
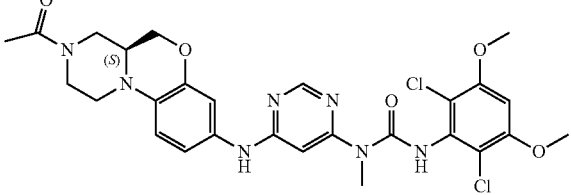
7R
8S
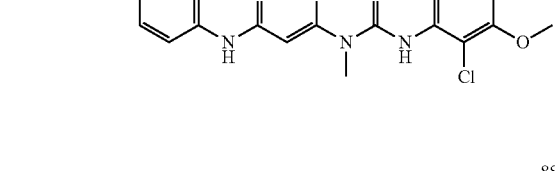
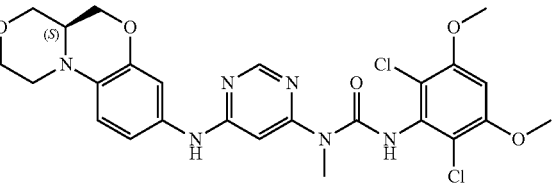

8R
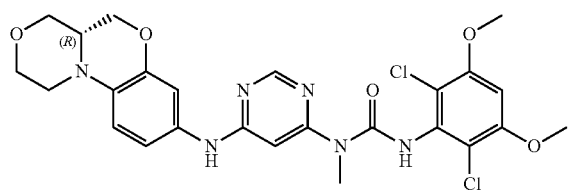
9S
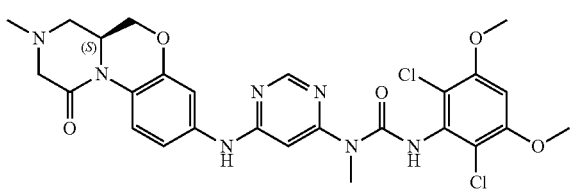
9R
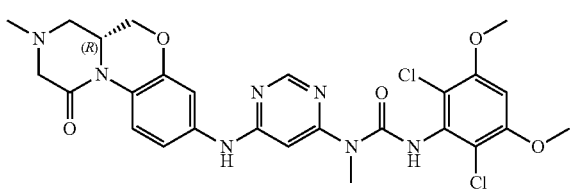
10S
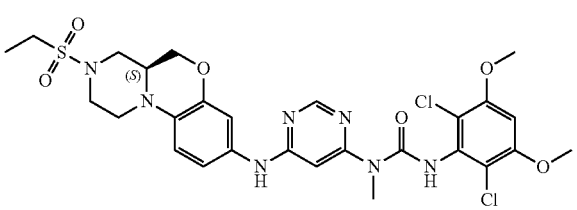
10R
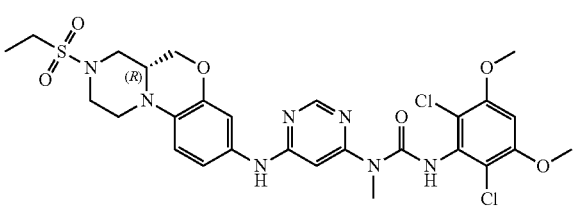
11S
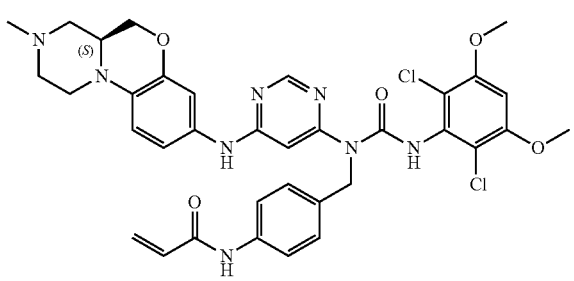
11R
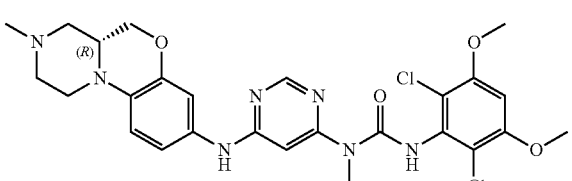
12S
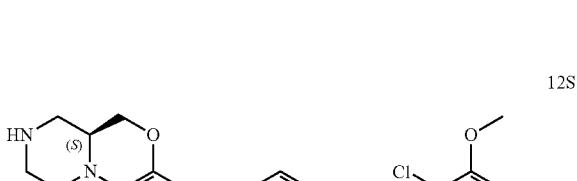
and
12R
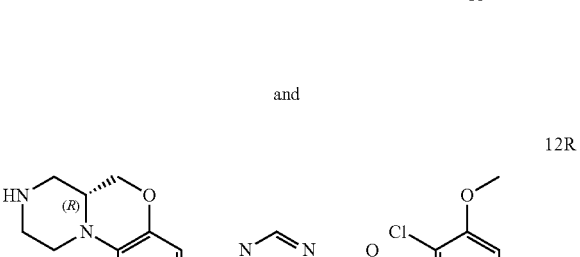
15. A pharmaceutical composition comprising: (i) a therapeutically effective amount of the compound of claim 1, or the pharmaceutically acceptable salt thereof, and (ii) a pharmaceutically acceptable carrier.
16. A method for the preparation of compound of claim 1, wherein the method comprises the following steps:
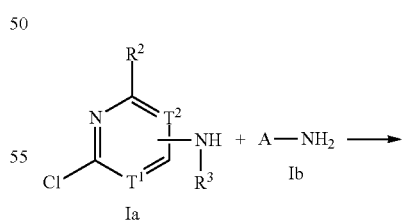

(1) in an inert solvent, reacting compound Ia with compound Ib, so as to provide compound Ic; and

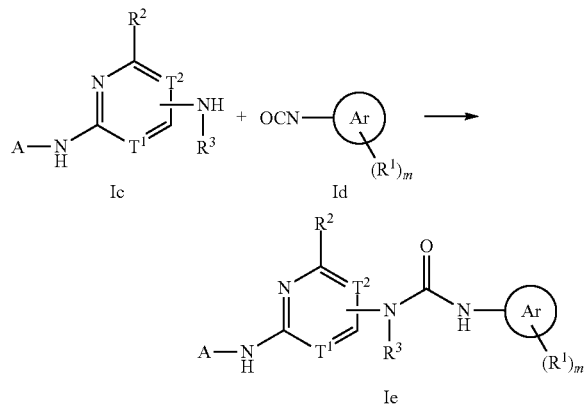

(2) in an inert solvent, reacting compound Ic with compound Id, so as to provide the target compound Ie; wherein the groups are defined as in claim 1.

17. A method of treating diseases associated with FGFR activity or expression, comprising administering an effective amount of compound of claim 1 or a pharmaceutically acceptable salt thereof to a subject in need thereof; and the disease is selected from the group consisting of bone-related diseases, T cell-mediated inflammations, autoimmune diseases, or tumors selected from the group consisting of lung cancer, bladder cancer, breast cancer, gastric cancer, liver cancer, salivary gland sarcoma, ovarian cancer, prostate cancer, cervical cancer, epithelial cell carcinoma, multiple myeloma, pancreatic cancer, Lymphoma, chronic myelogenous leukemia, lymphocytic leukemia, and cutaneous T-cell lymphoma.

18. A method of inhibiting FGFR activity, comprising administering an effective amount of compound of claim 1 or a pharmaceutically acceptable salt thereof to a subject in need thereof.

* * * * *